United States Patent
Wright et al.

(10) Patent No.: US 6,331,662 B1
(45) Date of Patent: Dec. 18, 2001

(54) PLANT RETROELEMENTS

(75) Inventors: David A. Wright, Boone; Daniel F. Voytas, Ames, both of IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/322,478

(22) Filed: May 28, 1999

Related U.S. Application Data

(60) Provisional application No. 60/087,125, filed on May 29, 1998.

(51) Int. Cl.[7] ............ C12N 15/33; C12N 15/82; A01H 5/00; A01H 5/10
(52) U.S. Cl. ............ 800/278; 435/468; 536/23.72; 800/298
(58) Field of Search ............ 536/23.72; 435/410, 435/419, 468; 800/278, 279, 280, 295, 298

(56) References Cited

PUBLICATIONS

Boeke et al., Pseudoviridae. In Virus Taxonomy: ICTV VIIth Report, edited by M.H.V. Van Regenmortel, et al. Springer Verlag, New York (1998).
Xiong and Eickbush, 9 *EMBO J.* 3353 (1990).
Voytas and Ausubel, 336 *Nature* 242 (1988).
Voytas et al., 126 *Genetics* 713 (1990).
Bennetzen, 4 *Trends Microbiol.* 347 (1996).
Chavanne et al., 37 *Plant Molecular Biol* 363 (1998).

*Primary Examiner*—Gary Benzion
*Assistant Examiner*—Ashwin Mehta
(74) *Attorney, Agent, or Firm*—Schwegman, Lundberg, Woessner & Kluth, P.A.

(57) ABSTRACT

The present invention provides plant retroelements useful as molecular tools. In one embodiment, the present invention provides nucleic acids encoding gag, pol and/or env genes of plant retroelements. The elements can be used, among other uses, as building blocks of other constructs, tools to find other nucleic acid sequences and tools to transfer nucleic acid into cells.

5 Claims, No Drawings

PLANT RETROELEMENTS

This application claims priority to U.S. Provisional patent application Ser. No. 60/087,125, filed May 29, 1998.

The present invention was funded, in part, by the United States Department of Agriculture, Contract Number IOW03120; the United States Government may have certain rights in the invention.

FIELD OF THE INVENTION

The present invention provides plant retroelements and methods related to plant retroelements. The invention involves techniques from the fields of: molecular biology, virology, genetics, bioinformatics, and, to a lesser extent, other related fields.

BACKGROUND OF THE INVENTION

The eukaryotic retrotransposons are divided into two distinct classes of elements based on their structure: the long terminal repeat (LTR) retrotransposons and the LINE-like or non LTR elements. Doolittle et al. (1989) Quart. Rev. Biol. 64: 1–30; Xiong and Eickbush (1990) EMBO J 9: 3353–3362. These element classes are related by the fact that each must undergo reverse transcription of an RNA intermediate to replicate, and each generally encodes its own reverse transcriptase. The LTR retrotransposons replicate by a mechanism which resembles that of the retroviruses. Boeke and Sandmeyer, (1991) Yeast transposable elements. In The Molecular and Cellular Biology of the Yeast Saccharomyces, edited by J. Broach, E. Jones and J. Pringle, pp. 193–261. Cold Spring Harbor Laboratory, Cold Spring Harbor, N.Y. They typically use a specific tRNA to prime reverse transcription, and a linear cDNA is synthesized through a series of template transfers that require redundant LTR sequences at each end of the element mRNA. This all occurs within a virus-like particle formed from proteins encoded by the retrotransposon mRNA. After reverse transcription, an integration complex is organized that directs the resulting cDNA to a new site in the genome of the host cell Phylogenetic analyses based on reverse transcriptase amino acid sequences resolve the LTR retrotransposons into two families: the Ty3/gypsy retrotransposons (Metaviridae), and the Ty1/copia elements (Pseudoviridae). Boeke et al., (1998) Metaviridae. In Virus Taxonomy: ICTV VIIth Report, edited by F. A. Murphy. Springer-Verlag, N.Y.; Boeke et al. (1998) Pseudoviridae. In Virus Taxonomy: ICTV VIIth Report, edited by F. A. Murphy. Springer Verlag, N.Y.; Xiong and Eickbush (1990) EMBO J. 9: 3353–3362. Although distinct, Ty3/gypsy elements are more closely related to the retroviruses than to the Ty1/copia elements. They also share a similar genetic organization with the retroviruses, principally in the order of integrase and reverse transcriptase in their pol genes. For the Ty3/gypsy elements, reverse transcriptase precedes integrase, and this order is reversed for the Ty1/copia elements. In addition, some Ty3/gypsy elements have an extra open reading frame (ORF) similar to retroviral envelope (env) proteins, which is required for viral infectivity. The Drosophila melanogaster gypsy retrotransposons encode an env-like ORF and can be transmitted between cells. Kim et al. (1994) Proc. Natl. Acad. Sci. USA 91: 1285–1289; Song et al. (1994) Genes & Dev. 8: 2046–2057. Thus there are two distinct lineages of infectious LTR retroelements, the retroviruses and those Ty3/gypsy retrotransposons that encode envelope-like proteins. The Ty3/gypsy elements have been divided into two genera, the metaviruses and the errantiviruses, the latter of which include all elements with env-like genes. Boeke et al., (1998) Metaviridae. In Virus Taxonomy: ICTV VIIth Report, edited by F. A. Murphy. Springer-Verlag, N.Y.

In plants, retrotransposons have been extremely successful. Bennetzen (1996) Trends Microbiol. 4: 347–353; Voytas (1996) Genetics 142: 569–578. The enormous size of many plant genomes demonstrates a great tolerance for repetitive DNA, a substantial proportion of which appears to be composed of retrotransposons. Because of their abundance, retrotransposons have undoubtedly influenced plant gene evolution. They can cause mutations in coding sequences (Grandbastien et al. (1989) Nature 337: 376–380; Hirochika et al. (1996) Proc. Natl. Acad. Sci. USA 93: 7783–7788; Purugganan and Wessler (1994) Proc. Natl. Acad. Sci. USA 91: 11674–11678), and the promoter regions of some plant genes contain relics of retrotransposon insertions that contribute transcriptional regulatory sequences. White et al. (1994) Proc. Natl. Acad. Sci. USA 91: 11792–11796. Retrotransposons also generate gene duplications: Repetitive retrotransposon sequences provide substrates for unequal crossing over, and such an event is thought to have caused a zein gene duplication in maize. White et al. (1994) Proc. Natl. Acad. Sci. USA 91: 11792–11796. Occasionally, cellular mRNAs are reverse transcribed and the resultant cDNA recombines into the genome giving rise to new genes, or more frequently, cDNA pseudogenes. Maestre et al. (1995) EMBO J. 14: 6333–6338. The transduction of gene sequences during reverse transcription, which produced the oncogenic retroviruses, has also been documented to occur for a plant retrotransposon (Bureau et al. (1994) Cell 77: 479–480.; Jin and Bennetzen (1994) Plant Cell 6: 1177 1186); a maize Bs1 insertion in Adh1 carries part of an ATPase gene and is the only known example of a retrotransposon-mediated gene transduction event.

Plant genomes encode representatives of the two major lineages of LTR retrotransposons that have been identified in other eukaryotes. Among these are numerous examples of Ty1/copia elements (e.g. Konieczny et al. (1991) Genetics 127: 801–809; Voytas and Ausubel (1988) Nature 336: 242–244; Voytas et al. (1990) Genetics 126: 713–721) Also prevalent are Ty3/gypsy elements, which are members of the genus Metaviridae (Smyth et al. 1989; Purugganan and Wessler 1994 Proc. Natl. Acad. Sci. USA 91: 11674–11678; Su and Brown 1997). As stated above, the metaviruses do not encode an envelope protein characteristic of the retroviruses. It has been suggested that some plant retrovirus-like elements may have lost, or not yet gained, genes such as the envelope gene required for cell-to-cell transmission (Bennetzen (1996) Trends Microbiol. 4: 347–353). As one group of researchers described the uncertainty, "[s]ince genes encoding ENV [envelope] functions are very heterogeneous at the sequence level and difficult to identify by homology even between retroviruses, the possibility cannot be completely excluded at the present time that the 3' ORF of Cyclops [the retrotransposon described in the paper] is, in fact, an env gene and, hence, Cyclops is a retrovirus or a descendant of one." Chavanne et al. (1998) Plant Molecular Biol 37: 363–375.

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

In general, the present invention provides materials, such as nucleic acids, vectors, cells, and plants (including plant parts, seeds, embryos, etc.), and methods to manipulate the materials. In particular, molecular tools are provided in the form of retroelements and retroelement-containing vectors, cells and plants. The particular methods include methods to introduce the retroelements into cells, especially wherein the retroelements carries at least one agronomically-significant characteristic. The best mode of the present invention is a particular method to transfer agronomically-significant characteristics to plants wherein a helper cell line which expresses gag, pol and env sequences is used to enable transfer of a secondary construct which carries an agronomically-significant characteristic and has retroelement sequences that allow for replication and integration.

In one embodiment, there are provided isolated nucleic acid molecules, wherein said nucleic acid molecules encode at least a portion of a plant retroelement and comprises a nucleic acid sequence selected from the group consisting of:

(a) a nucleic acid sequence which is a plant retroelement primer binding site and which has more than 95% identity to SEQ ID NO 2, wherein said identity can be defined using the DNAsis computer program and default parameters;

(b) a nucleic acid sequence which is at least a portion of a plant retroelement envelope sequence and which has more than 50% identity to SEQ ID NO 5, wherein said identity can be determined using the DNAsis computer program and default parameters;

(c) a nucleic acid sequence which is at least a portion of a plant retroelement gag sequence and which has more than 50% identity to SEQ ID NO 7, wherein said identity can be determined using the DNAsis computer program and default parameters;

(d) a nucleic acid sequence which is at least a portion of a plant retroelement integrase sequence and which has more than 70% identity to SEQ ID NO 9, wherein said identity can be determined using the DNAsis computer program and default parameters;

(e) a nucleic acid sequence which is at least a portion of a plant retroelement reverse transcriptase sequence and which has more than 70% identity to SEQ ID NO 11, wherein said identity can be determined using the DNAsis computer program and default parameters;

(f) a nucleic acid sequence which is at least a portion of a plant retroelement protease sequence and which has more than 50% identity to SEQ ID NO 13, wherein said identity can be determined using the DNAsis computer program and default parameters;

(g) a nucleic acid sequence which is at least a portion of a plant retroelement RNAseH sequence and which has more than 70% identity to SEQ ID NO 15, wherein said identity can be determined using the DNAsis computer program and default parameters;

(h) a nucleic acid sequence which is at least a portion of a plant retroelement sequence and which has more than 50% identity to SEQ ID NO 17, wherein said identity can be determined using the DNAsis computer program and default parameters;

(i) a nucleic acid sequence which is selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17.

(j) a nucleic acid sequence which encodes an amino acid sequence which is at least a portion of a plant retroelement envelope sequence and has more than 30% identity to SEQ ID NO 6, wherein said identity can be determined using the DNAsis computer program and default parameters;

(k) a nucleic acid sequence which encodes an amino acid sequence which is at least a portion of a plant retroelement gag sequence and has more than 30% identity to SEQ ID NO 8, wherein said identity can be determined using the DNAsis computer program and default parameters;

(l) a nucleic acid sequence which encodes an amino acid sequence which is at least a portion of a plant retroelement integrase sequence and has more than 75% identity to SEQ ID NO 10, wherein said identity can be determined using the DNAsis computer program and default parameters;

(m) a nucleic acid sequence which encodes an amino acid sequence which is at least a portion of a plant retroelement reverse transcriptase sequence and has more than 79% identity to SEQ ID NO 12, wherein said identity can be determined using the DNAsis computer program and default parameters;

(n) a nucleic acid sequence which encodes an amino acid sequence which is at least a portion of a plant retroelement protease sequence and has more than 55% identity to SEQ ID NO 14, wherein said identity can be determined using the DNAsis computer program and default parameters;

(o) a nucleic acid sequence which encodes an amino acid sequence which is at least a portion of a plant retroelement RNAseH sequence and has more than 90% identity to SEQ ID NO 16, wherein said identity can be determined using the DNAsis computer program and default parameters;

(p) a nucleic acid sequence which encodes an amino acid sequence which is at least a portion of a plant retroelement sequence and has more than 40% identity to SEQ ID NO 18, wherein said identity can be determined using the DNAsis computer program;

(q) a nucleic acid sequence which encodes an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18;

(r) a nucleic acid sequence which encodes an allelic variant of an amino acid sequence selected from the group consisting of: SEQ ID NO 4; SEQ ID NO 6; SEQ ID NO 8; SEQ ID NO 10, SEQ ID NO 12; SEQ ID NO 14; SEQ ID NO 16; and SEQ ID NO 18; and (s) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); a nucleic acid sequence of (e); a nucleic acid sequence of (f); a nucleic acid sequence of (g); a nucleic acid sequence of (h); a nucleic acid sequence of (i); a nucleic acid sequence of (j); a nucleic acid sequence of (k); a nucleic acid sequence of (l); a nucleic acid sequence of (m); a nucleic acid sequence of (n); a nucleic acid sequence of (o); a nucleic acid sequence of (p); a nucleic acid sequence of (q); and a nucleic acid sequence of (r).

Seeds and plants comprising a nucleic acid as above are particularly provided. Nucleic acid molecules as above which comprise gag, pol and env genes and which comprise adenine-thymidine-guanidine as the gag gene start codon are also particularly provided. Those which comprise gag, pol and env genes, the adenine-thymidine-guanidine as the gag gene start codon, and which further comprises SEQ ID NO 4 are also provided.

Plant envelope sequences and constructs which comprise the sequences are provided, as are cells, seeds, embryos and plants comprising them. Preferred are isolated nucleic acid molecules, wherein said nucleic acid molecules encode at least a portion of a plant envelope sequence and comprises a nucleic acid sequence selected from the group consisting of:
(a) a nucleic acid sequence which has more than 90% identity to SEQ ID NO 5, wherein said identity can be determined using the DNAsis computer program and default parameters;
(b) a nucleic acid sequence which encodes SEQ ID NO 5;
(c) a nucleic acid sequence which encodes an amino acid sequence which has greater than 85% identity to SEQ ID NO 6, wherein said identity can be determined using the DNAsis computer program and default parameters;
(d) a nucleic acid sequence which encodes amino acid sequence SEQ ID NO 6;
(e) a nucleic acid sequence which encodes an allelic variant of SEQ ID NO 6; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant envelope proteins comprising an amino acid sequence encoded by the above. Methods to impart agronomically-significant characteristics to at least one plant cell are also provided, comprising: contacting a plant envelope protein as described to at least one plant cell under conditions sufficient to allow a nucleic acid molecule to enter said cell, wherein said nucleic acid molecule encodes an agronomically-significant characteristic.

Plant integrase sequences and constructs which comprise the sequences are provided, as are cells, seeds, embryos and plants comprising them. Preferred are isolated nucleic acid molecules, wherein said nucleic acid molecules encode at least a portion of a plant integrase sequence and comprises a nucleic acid sequence selected from the group consisting of:
(a) a nucleic acid sequence which has more than 90% identity to SEQ ID NO 9, wherein said identity can be determined using the DNAsis computer program and default parameters;
(b) a nucleic acid sequence which encodes SEQ ID NO 9;
(c) a nucleic acid sequence which encodes an amino acid sequence which has greater than 85% identity to SEQ ID NO 10, wherein said identity can be determined using the DNAsis computer program and default parameters;
(d) a nucleic acid sequence which encodes amino acid sequence SEQ ID NO 10;
(e) a nucleic acid sequence which encodes an allelic variant of SEQ ID NO 10; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant integrase proteins comprising an amino acid sequence encoded by the above. Methods to impart agronomically-significant characteristics to at least one plant cell are also provided, comprising: contacting a plant integrase protein as described to at least one plant cell under conditions sufficient to allow a nucleic acid molecule to enter said cell wherein said nucleic acid molecule encodes an agronomically-significant characteristic.

Plant reverse transcriptase sequences and constructs which comprise the sequences are provided, as are cells, seeds, embryos and plants comprising them. Preferred are isolated nucleic acid molecules, wherein said nucleic acid molecules encode at least a portion of a plant reverse transcriptase sequence and comprises a nucleic acid sequence selected from the group consisting of:
(a) a nucleic acid sequence which has more than 90% identity to SEQ ID NO 11, wherein said identity can be determined using the DNAsis computer program and default parameters;
(b) a nucleic acid sequence which encodes SEQ ID NO 11;
(c) a nucleic acid sequence which encodes an amino acid sequence which has greater than 85% identity to SEQ ID NO 12, wherein said identity can be determined using the DNAsis computer program and default parameters;
(d) a nucleic acid sequence which encodes amino acid sequence SEQ ID NO 12;
(e) a nucleic acid sequence which encodes an allelic variant of SEQ ID NO 12; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant reverse transcriptase proteins comprising an amino acid sequence encoded by the above. Methods to impart agronomically-significant characteristics to at least one plant cell are also provided, comprising: contacting a plant reverse transcriptase protein as described to at least one plant cell under conditions sufficient to allow a nucleic acid molecule to enter said cell, wherein said nucleic acid molecule encodes an agronomically-significant characteristic.

Plant RNAseH sequences and constructs which comprise the sequences are provided, as are cells, seeds, embryos and plants comprising them. Preferred are isolated nucleic acid molecules, wherein said nucleic acid molecules encode at least a portion of a plant RNAseH sequence and comprises a nucleic acid sequence selected from the group consisting of:
(a) a nucleic acid sequence which has more than 90% identity to SEQ ID NO 15, wherein said identity can be determined using the DNAsis computer program and default parameters;
(b) a nucleic acid sequence which encodes SEQ ID NO 15;
(c) a nucleic acid sequence which encodes an amino acid sequence which has greater than 95% identity to SEQ ID NO 16, wherein said identity can be determined using the DNAsis computer program and default parameters;
(d) a nucleic acid sequence which encodes amino acid sequence SEQ ID NO 16;
(e) a nucleic acid sequence which encodes an allelic variant of SEQ ID NO 16; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant RNAseH proteins comprising an amino acid sequence encoded by the above. Methods to impart agronomically-significant characteristics to at least one plant cell are also provided, comprising: contacting a plant RNAseH protein as described to at least one plant cell under conditions sufficient to allow a nucleic acid molecule to enter said cell, wherein said nucleic acid molecule encodes an agronomically-significant characteristic.

Plant retroelement sequences and constructs which comprise the sequences are provided, as are cells, seeds, embryos and plants comprising them. Preferred are isolated nucleic acid molecules, wherein said nucleic acid molecules encode at least a portion of a plant retroelement sequence and comprises a nucleic acid sequence selected from the group consisting of:

(a) a nucleic acid sequence which has more than 95% identity to a nucleic acid sequence selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17, wherein said identity can be determined using the DNAsis computer program and default parameters;

(b) a nucleic acid sequence which is selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17;

(c) a nucleic acid sequence which encodes an amino acid sequence which has more than 90% identity to an amino acid sequence selected from the group consisting of SEQ ID NO 4; SEQ ID NO 6; SEQ ID NO 8; SEQ ID NO 10; SEQ ID NO 12; SEQ ID NO 14; SEQ ID NO 16; SEQ ID NO 18, wherein said identity can be determined using the DNAsis computer program and default parameters;

(d) a nucleic acid sequence which encodes an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18;

(e) a nucleic acid sequence which encodes an allelic variant of an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Nucleic acid molecule as above, which further comprises at least one nucleic acid sequence which encodes at least one agronomically-significant characteristic are preferred. More preferred are those nucleic acid molecules as described wherein the agronomically-significant characteristic is selected from the group consisting of: male sterility; self-incompatibility; foreign organism resistance; improved biosynthetic pathways; environmental tolerance; photosynthetic pathways; and nutrient content and those wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Seeds and plants comprising a nucleic acid molecule as described are also preferred. More preferred are plants as described, wherein the plant is selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower; peanut; and olive. Most preferred are plants as described which are soybean plants.

Plant retroelements comprising an amino acid sequence encoded by a nucleic acid sequence described are also provided. Plant cells comprising a nucleic acid molecule described herein, as well as plant retroviral proteins encoded by nucleic acid molecules described herein are provided.

Moreover, methods to transfer nucleic acid into a plant cell, comprising contacting a nucleic acid molecule of the present invention with at least one plant cell under conditions sufficient to allow said nucleic acid molecule to enter at least one cell of said plant are provided. In particular there is provided, methods to impart agronomically-significant characteristics to at least one plant cell, comprising: contacting a plant retroelement of the present invention to at least one plant cell under conditions sufficient to allow a nucleic acid molecule to enter said cell, wherein said nucleic acid molecule encodes an agronomically-significant characteristic. Methods as described, wherein the agronomically-significant characteristic is selected from the group consisting of: male sterility; self-incompatibility; foreign organism resistance; improved biosynthetic pathways; environmental tolerance; photosynthetic pathways; and nutrient content and those wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Plant retroelement sequences comprising specialized signals, and constructs which comprise the sequences are provided, as are cells, seeds, embryos and plants comprising them. Preferred are isolated nucleic acid molecules, comprisng a nucleic acid sequence selected from the group consisting of:

(a) a nucleic acid sequence which has more than 95% identity to SEQ ID NO 2; wherein said identity can be determined using the DNAsis computer program and default parameters;

(b) a nucleic acid sequence which is SEQ ID NO 2;

(c) a nucleic acid sequence which encodes amino acid sequence SEQ ID NO 4; and (d) a nucleic acid sequence fully complementary to a nucleic acid sequence selected from the group consisting of: a nucleic acid sequence of (a); a nucleic acid sequence of (b); and a nucleic acid sequence of (c).

Plant retroelements as described above, which further comprise at least one nucleic acid sequence which encodes at least one agronomically-significant characteristic are preferred. More preferred are those methods wherein the agronomically-significant characteristic is selected from the group consisting of: male sterility; self-incompatibility; foreign organism resistance; improved biosynthetic pathways; environmental tolerance; photosynthetic pathways; and nutrient content and those wherein the agrononically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); anino acid content; and fatty acid content.

Preferred are plant retroviral particles comprising an isolated retroelement as described, and seeds and plants comprising the retroelements as described. More preferred plants include soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower, peanut; and olive. Soybean is most preferred.

Also provided are methods to transfer nucleic acid into a plant cell, comprising contacting a plant retroelement as described with at least one plant cell under conditions sufficient to allow said plant retroelement to enter said cell. Methods to impart agronomically-significant characteristics to a plant, comprising contacting a plant retroelement as described with at least one plant cell under conditions sufficient to allow said plant retroelement to enter said cell are also preferred. Those methods wherein the plant retroelement is contacted with said cell via a plant retroviral particle described herein are preferred.

Plant retroviruses are also provided. In particular, plant retroviral particles comprising a plant-derived retrovirus envelope protein are provided. Plant retroviral particles comprising a plant-derived retrovirus envelope protein and which further comprise a plant retroviral protein selected from the group consisting of: plant-derived integrase; plant derived reverse transcriptase; plant-derived gag; and plant-derived RNAseH are preferred.

Plant retroviral particles comprising specialized retroviral proteins, and cells, seeds, embryos and plants which comprise the retroviral particles are provided. Preferred are isolated retroviral particles comprising a plant retroviral protein encoded by a nucleic acid sequence selected from the group consisting of:
(a) a nucleic acid sequence comprising (i) a nucleic acid sequence which encodes at least one plant retroviral envelope protein, and (ii) a nucleic acid sequence which has more than 60% identity to a nucleic acid sequence selected from the group consisting of: SEQ ID NO 9; SEQ ID NO 11; SEQ ID NO 15; SEQ ID NO 26; SEQ ID NO 27; SEQ ID NO 28; SEQ ID NO 29; SEQ ID NO 30; and SEQ ID NO 31, wherein said identity can be determined using the DNAsis computer program and default parameters;
(b) a nucleic acid sequence which encodes an amino acid sequence encoded by a nucleic acid sequence (a);
(c) a nucleic acid sequence which encodes an allelic variant of an amino acid sequence encoded by a nucleic acid sequence of (a); and
(d) a nucleic acid sequence fully complementary to a nucleic acid sequence selected from the group consisting of: a nucleic acid sequence of (a); a nucleic acid sequence of (b); and a nucleic acid sequence of (c).

In particular, there are provided plant retroviral particles, wherein said nucleic acid sequence as described in (a) comprises a plant envelope nucleic acid specifically mentioned in claim 6 is preferred. Those particles which further comprise at least one nucleic acid sequence which encodes at least one agronomically-significant characteristic are preferred.

Also provided are methods to transfer nucleic acid into a plant cell, comprising contacting a plant retroviral particle as described above to at least one plant cell under conditions sufficient to allow said nucleic acid to enter said cell. More preferred are methods to impart agrononically-significant characteristics to a plant, comprising contacting a plant retroviral particle as described to at least one plant cell under conditions sufficient to allow said nucleic acid to enter said cell.

More preferred are isolated retroviral particles comprising a plant retroviral protein encoded by a nucleic acid sequence selected from the group consisting of:
(a) a nucleic acid sequence which has more than 80% identity to a nucleic acid sequence selected from the group consisting of: SEQ ID NO 9; SEQ ID NO 11; and SEQ ID NO 15, wherein said identity can be determined using the DNAsis computer program and default parameters;
(b) a nucleic acid sequence which encodes a nucleic acid selected from the group consisting of: SEQ ID NO 9; SEQ ID NO 11; and SEQ ID NO 15;
(c) a nucleic acid sequence which encodes an amino acid sequence encoded by a nucleic acid sequence selected from the group consisting of: a nucleic acid sequence of (a); and a nucleic acid sequence of (b);
(d) a nucleic acid sequence which encodes an allelic variant of an amino acid sequence encoded by a nucleic acid selected from the group consisting of: a nucleic acid sequence of (a); and a nucleic acid sequence of (b); and
(e) a nucleic acid sequence fully complementary to a nucleic acid sequence selected from the group consisting of: a nucleic acid sequence of (a); a nucleic acid sequence of (b); a nucleic acid sequence of (c); and a nucleic acid sequence of (d).

Nucleic acids as above, which further comprises at least one nucleic acid sequence which encodes at least one agronomically-significant characteristic are preferred. More preferred are those nucleic acids wherein the agronomically-significant characteristic is selected from the group consisting of: male sterility; self-incompatibility; foreign organism resistance; improved biosynthetic pathways; environmental tolerance; photosynthetic pathways; and nutrient content. Also more preferred are those isolated nucleic acid molecule as described, wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

Also preferred are isolated retroviral particles comprising a plant retroviral protein encoded by a nucleic acid sequence selected from the group consisting of:
(a) a nucleic acid sequence which has more than 60% identity to a nucleic acid sequence selected from the group consisting of SEQ ID NO 9; SEQ ID NO 11; SEQ ID NO 15; SEQ ID NO 26; SEQ ID NO 27; SEQ ID NO 28; SEQ ID NO 29; SEQ ID NO 30; and SEQ ID NO 31, wherein said identity can be determined using the DNAsis computer program and default parameters;

(b) a nucleic acid sequence which encodes a nucleic acid selected from the group consisting of: SEQ ID NO 9, SEQ ID NO 11; SEQ ID NO 15; SEQ ID NO 26; SEQ ID NO 27; SEQ ID NO 28; SEQ ID NO 29; SEQ ID NO 30; and SEQ ID NO 31;

(c) a nucleic acid sequence which encodes an amino acid sequence encoded by a nucleic acid sequence selected from the group consisting of: a nucleic acid sequence of (a); and a nucleic acid sequence of (b);

(d) a nucleic acid sequence which encodes an allelic variant of an amino acid sequence encoded by a nucleic acid selected from the group consisting of: a nucleic acid sequence of (a); and a nucleic acid sequence of (b); and (e) a nucleic acid sequence fully complementary to a nucleic acid sequence selected from the group consisting of: a nucleic acid sequence of (a); a nucleic acid sequence of (b); a nucleic acid sequence of (c); and a nucleic acid sequence of (d).

Plant retroviral particles as described above, which further comprises an envelope-encoding nucleic acid sequence specifically described herein are preferred. Preferred are those retroviral particles which further comprise at least one nucleic acid sequence which encodes at least one agronomically-significant characteristic.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

"Allelic variant" is meant to refer to a full length gene or partial sequence of a full length gene that occurs at essentially the same locus (or loci) as the referent sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

By "agronomically-significant" it is meant any trait of a plant which is recognized by members of the agricultural industry as desirable.

"Fragment" is meant to refer to any subset of the referent nucleic acid molecule.

By "plant" it is meant one or more plant seed, plant embryo, plant part or whole plant. The plant may be an angiosperm (monocot or dicot), gymnosperm, man-made or naturally-occurring.

By "proteins" it is meant any compounds which comprise amino acids, including peptides, polypeptides, fusion proteins, etc.

Moreover, for the purposes of the present invention, the term "a" or "an" refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis. Lastly, "more than" and "greater than" are interchangeable, and when used to modify a percent identity, iec. "more than 90% identity", mean any increment to 100%, so long as the increment were greater than the percentage specifically named. In the example of "more than 90% identity", the term would include, among all other possibilities, 90.00001, 93.7, 98.04 and 99. 0827 and 100%.

The following is a summary of the sequence listing, as a convenient reference.

| SEQ ID NO | Description |
|---|---|
| 1 | specialized primer binding site version 1 |
| 2 | specialized primer binding site version 2 |
| 3 | specialized polypurine tract |
| 4 | targeting sequence |
| 5 | NA generic envelope |
| 6 | AA of 5 |
| 7 | NA of generic gag |
| 8 | AA of 7 |
| 9 | NA of generic integrase |
| 10 | AA of 9 |
| 11 | NA of generic reverse transcriptase |
| 12 | AA of 11 |
| 13 | generic protease |
| 14 | AA of 13 |
| 15 | generic RNAseH |
| 16 | AA of 15 |
| 17 | generic retroelement |
| 18 | AA of 17 |
| 19 | NA calypso 1-1 |
| 20 | NA calypso 1-2 |
| 21 | NA calypso 1-3 |
| 22 | NA calypso 2-1 |
| 23 | NA calypso 2-2 |
| 24 | NA athila env |
| 25 | NA cyclops env |
| 26 | NA athila integrase |
| 27 | NA athila reverse transcriptase |
| 28 | NA athila RNAseH |
| 29 | NA cyclops reverse transcriptase |
| 30 | NA cyclops RNAseH |
| 31 | NA cyclops integrase |
| 32 | NA calypso envelope |
| 33 | NA calypso RNAseH |
| 34 | NA calypso reverse transcriptase |
| 35 | NA calypso integrase |
| 36 | Primer binding site A |
| 37 | Primer binding site B |
| 38 | Primer binding site minimum |
| 39 | Primer binding site extended |
| 40 | polypurine tract A |
| 41 | polypurine tract B |

DETAILED DESCRIPTION OF THE INVENTION

In one embodiment, there are provided isolated nucleic acid molecules, wherein said nucleic acid molecules encode at least a portion of a plant retroelement and comprises a nucleic acid sequence selected from the group consisting of:

(a) a nucleic acid sequence which is a plant retroelement primer binding site and which has more than 95% identity to SEQ ID NO 2, wherein said identity can be determined using the DNAsis computer program and default parameters;

(b) a nucleic acid sequence which is at least a portion of a plant retroelement envelope sequence and which has more than 50% identity to SEQ ID NO 5, wherein said identity can be determined using the DNAsis computer program and default parameters;

(c) a nucleic acid sequence which is at least a portion of a plant retroelement gag sequence and which has more than 50% identity to SEQ ID NO 7, wherein said identity can be determined using the DNAsis computer program and default parameters;

(d) a nucleic acid sequence which is at least a portion of a plant retroelement integrase sequence and which has more than 70% identity to SEQ ID NO 9, wherein said identity can be determined using the DNAsis computer program and default parameters;

(e) a nucleic acid sequence which is at least a portion of a plant retroelement reverse transcriptase sequence and which has more than 70% identity to SEQ ID NO 11, wherein said identity can be determined using the DNAsis computer program and default parameters;

(f) a nucleic acid sequence which is at least a portion of a plant retroelement protease sequence and which has more than 50% identity to SEQ ID NO 13, wherein said identity can be determined using the DNAsis computer program and default parameters;

(g) a nucleic acid sequence which is at least a portion of a plant retroelement RNAseH sequence and which has more than 70% identity to SEQ ID NO 15, wherein said identity can be determined using the DNAsis computer program and default parameters;

(h) a nucleic acid sequence which is at least a portion of a plant retroelement sequence and which has more than 50% identity to SEQ ID NO 17, wherein said identity can be determined using the DNAsis computer program and default parameters;

(i) a nucleic acid sequence which is selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17.

(j) a nucleic acid sequence which encodes an amino acid sequence which is at least a portion of a plant retroelement envelope sequence and has more than 30% identity to SEQ ID NO 6, wherein said identity can be determined using the DNAsis computer program and default parameters;

(k) a nucleic acid sequence which encodes an amino acid sequence which is at least a portion of a plant retroelement gag sequence and has more than 30% identity to SEQ ID NO 8, wherein said identity can be determined using the DNAsis computer program and default parameters;

(l) a nucleic acid sequence which encodes an amino acid sequence which is at least a portion of a plant retroelement integrase sequence and has more than 75% identity to SEQ ID NO 10, wherein said identity can be determined using the DNAsis computer program and default parameters;

(m) a nucleic acid sequence which encodes an amino acid sequence which is at least a portion of a plant retroelement reverse transcriptase sequence and has more than 79% identity to SEQ ID NO 12, wherein said identity can be determined using the DNAsis computer program and default parameters;

(n) a nucleic acid sequence which encodes an amino acid sequence which is at least a portion of a plant retroelement protease sequence and has more than 55% identity to SEQ ID NO 14, wherein said identity can be determined using the DNAsis computer program and default parameters;

(o) a nucleic acid sequence which encodes an amino acid sequence which is at least a portion of a plant retroelement RNAseH sequence and has more than 90% identity to SEQ ID NO 16, wherein said identity can be determined using the DNAsis computer program and default parameters;

(p) a nucleic acid sequence which encodes an amino acid sequence which is at least a portion of a plant retroelement sequence and has more than 40% identity to SEQ ID NO 18, wherein said identity can be determined using the DNAsis computer program;

(q) a nucleic acid sequence which encodes an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18;

(r) a nucleic acid sequence which encodes an allelic variant of an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18; and (s) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); a nucleic acid sequence of (e); a nucleic acid sequence of (f); a nucleic acid sequence of (g); a nucleic acid sequence of (h); a nucleic acid sequence of (i); a nucleic acid sequence of j); a nucleic acid sequence of (k); a nucleic acid sequence of (l); a nucleic acid sequence of (m); a nucleic acid sequence of (n); a nucleic acid sequence of (o); a nucleic acid sequence of (p); a nucleic acid sequence of (q); and a nucleic acid sequence of (r).

Seeds and plants comprising a nucleic acid as above are particularly provided. Nucleic acid molecules as above which comprise gag, pol and env genes and which comprise adenine-thymidine-guanidine as the gag gene start codon are also particularly provided. Those which comprise gag, pol and env genes, the adenine-thymidine-guanidine as the gag gene start codon, and which further comprises SEQ ID NO 4 are also provided.

Included within the scope of the present invention, with particular regard to the nucleic acids above, are allelic variants, degenerate sequences and homologues. The present invention also includes variants due to laboratory manipulation, such as, but not limited to, variants produced during polymerase chain reaction amplification or site directed mutagenesis. It is also well known that there is a substantial amount of redundancy in the various codons which code for specific amino acids. Therefore, this invention is also directed to those nucleic acid sequences which contain alternative codons which code for the eventual translation of the identical amino acid. Also included within the scope of this invention are mutations either in the nucleic acid sequence or the translated protein which do not substantially alter the ultimate physical properties of the expressed protein. For example, substitution of valine for leucine, arginine for lysine, or asparagine for glutamine may not cause a change in functionality of the polypeptide. Lastly, a nucleic acid sequence homologous to the exemplified nucleic acid molecules (or allelic variants or degenerates thereof) will have at least 85%, preferably 90%, and most preferably 95% sequence identity with a nucleic acid molecule in the sequence listing.

It is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

Knowing the nucleic acid sequences of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain similar nucleic acid molecules from other species. Such nucleic acid molecules can be obtained in a variety of ways including screening appropriate expression libraries with antibodies of the present invention; traditional cloning techniques using oligonucleotide probes of the present invention to screen appropriate libraries of DNA; and PCR amplification of appropriate libraries or DNA using oligonucleotide primers of the present invention. Preferred libraries to screen or from which to amplify nucleic acid molecules include canine cDNA libraries as well as genomic DNA libraries. Similarly, preferred DNA sources to screen or from which to amplify nucleic acid molecules include adult cDNA and genomic DNA. Techniques to clone and amplify genes are disclosed, for example, in Sambrook et al., ibid.

Recombination constructs can be made using the starting materials above or with additional materials, using methods well-known in the art. In general, the sequences can be manipulated to have ligase-compatible ends, and incubated with ligase to generate full constructs. For example, restriction enzymes can be chosen on the basis of their ability to cut at an acceptable site in both sequence to be ligated, or a linker may be added to convert the sequence end(s) to ones that are compatible. The methods for conducting these types of molecular manipulations are well-known in the art, and are described in detail in Sambrook et al., Molecular Cloning. A Laboratory Manual (Cold Spring Harbor Laboratory Press, 1989) and Ausubel et al., Current Protocols in Molecular Biology (Greene Publishing Associates, Inc., 1993). The methods described herein according to Tinland et al., 91 Proc. Natl. Acad. Sci.USA 8000 (1994) can also be used.

The present invention also includes nucleic acid molecules that are oligonucleotides capable of hybridizing, under stringent hybridization conditions, with complementary regions of other, preferably longer, nucleic acid molecules of the present invention. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents. Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art See, for example, Sambrook, et al., 1989, Molecular Cloning: A Laboratory Manual, Cold Spring Harbor Labs Press, and Meinkoth, et al., 1984, Anal. Biochem. 138, 267–284.

Recombinant molecules of the present invention may also (a) contain secretory signals (i.e., signal segment nucleic acid sequences) to enable an expressed protein of the present invention to be secreted from the cell that produces the protein and/or (b) contain fusion sequences which lead to the expression of nucleic acid molecules of the present invention as fusion proteins. Recombinant molecules may also include intervening and/or untranslated sequences surrounding and/or within the nucleic acid sequences of nucleic acid molecules of the present invention.

One embodiment of the present invention includes recombinant vectors, which include at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule (s) are derived. The vector can be either RNA or DNA, either prokaryotic or eukaryotic, and typically is a virus or a plasmid. Recombinant vectors can be used in the cloning, sequencing, and/or otherwise manipulation of nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequences that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda pL and lambda pR and fusions that include such promoters), bacteriophage T7, T71ac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, Heliothis zea insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with plants. The present invention also comprises expression vectors comprising a nucleic acid molecule described herein.

For instance, the following promoters would be useful in early expression of the present sequences: Ogs4B (Tsuchiya et al., 36 Plant Cell Physiology 487 (1994); TA29 (Koltunow et al., 2 Plant Cell 1201 (1990); A3 & A9 (Paul et al., 19 Plant Molecular Biology 611 (1992). In order to then constitutively express the sequences described above, the construct optionally contains, for example, a 35S promoter.

Vectors which comprise the above sequences are within the scope of the present invention, as are plants transformed with the above sequences. Vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.). Preferred vectors are those which are capable of transferring the sequences disclosed herein into plant cells or plant parts.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Nucleic acids of the present invention may be transferred to cells according to the methods of the present invention, as well as using any of the following well-known means: infective, vector-containing bacterial strains (such as Agrobacterium rhizogenes and Agrobacterium tumefaciens) according to ie. Zambryski, 43 Ann. Rev. Pl. Physiol. Pl. Mol. Biol. 465 (1992); pollen-tube transformation [Zhonxun et al., 6 Plant Molec. Bio. 165 (1988)]; direct transformation of germinating seeds [Toepfer et al., 1 Plant Cell 133 (1989)]; polyethylene glycol or electroporation transformation [Christou et al., 84 Proc. Nat. Acad. Sci. 3662 (1987)]; and biolistic processes [Yang & Cristou, Particle Bombardment Technology for Gene Transfer (1994)].

The transformed cells may be induced to form transformed plants via organogenesis or embryogenesis, according to the procedures of Dixon Plant Cell Culture: A Practical Approach (IRL Press, Oxford 1987).

Any seed, embryo, plant or plant part is amenable to the present techniques. Of course, the agronomically-significant seeds, embryos, plants or plant parts are preferred. Soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower; peanut; and olive are among the preferred seeds, embryos, plants or plant parts. Particularly preferred are: soybean, tobacco and maize seeds, embryos, plants or plant parts. However, Arabidopsis seeds, embryos, plants or plant parts are also preferred, since it is an excellent system for study of plant genetics.

Preferred are those genes or sequences which are agronomically significant. For example, genes encoding male sterility, foreign organism resistance (viruses or bacteria), including genes which produce bacterial endotoxins, such as bacillus thurigiensis endotoxin, genes involved in specific biosynthetic pathways (eg. in fruit ripening, oil or pigment biosynthesis, seed formation, or carbohydrate metabolism), genes involved in environmental tolerance (eg. salt tolerance, lodging tolerance, cold/frost tolerance, drought tolerance, or tolerance to anaerobic conditions), or genes involved in nutrient content (eg. protein content, carbohydrate content, amino acid content, fatty acid content), genes involved in photosynthetic pathways, or genes involved in self-incompatibility. The choice of gene or sequence induced to recombine in the present invention is not limited. Examples of genes and how to obtain them are available through reference articles, books and supply catalogs, such as The Sourcebook (1-800-551-5291). Sambrook et al., Molecular Cloning. A Laboratory Manual (Cold Spring Harbor Laboratory Press, 1989) and Weising et al., 22 Ann Rev. Gen. 421 (1988) contain a synthesis of the information that is well-known in this art Plant envelope sequences and constructs which comprise the sequences are provided, as are cells, seeds, embryos and plants comprising them. Preferred are isolated nucleic acid molecules, wherein said nucleic acid molecules encode at least a portion of a plant envelope sequence and comprises a nucleic acid sequence selected from the group consisting of:

(a) a nucleic acid sequence which has more than 90% identity to SEQ ID NO 5, wherein said identity can be determined using the DNAsis computer program and default parameters;
(b) a nucleic acid sequence which encodes SEQ ID NO 5;
(c) a nucleic acid sequence which encodes an amino acid sequence which has greater than 85% identity to SEQ ID NO 6, wherein said identity can be determined using the DNAsis computer program and default parameters;
(d) a nucleic acid sequence which encodes amino acid sequence SEQ ID NO 6;
(e) a nucleic acid sequence which encodes an allelic variant of SEQ ID NO 6; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant envelope proteins comprising an amino acid sequence encoded by the above. Methods to impart agronomically-significant characteristics to at least one plant cell are also provided, comprising: contacting a plant envelope protein as described to at least one plant cell under conditions sufficient to allow a nucleic acid molecule to enter said cell, wherein said nucleic acid molecule encodes an agronomically-significant characteristic.

Plant integrase sequences and constructs which comprise the sequences are provided, as are cells, seeds, embryos and plants comprising them. Preferred are isolated nucleic acid molecules, wherein said nucleic acid molecules encode at least a portion of a plant integrase sequence and comprises a nucleic acid sequence selected from the group consisting of:
(a) a nucleic acid sequence which has more than 90% identity to SEQ ID NO 9, wherein said identity can be determined using the DNAsis computer program and default parameters;
(b) a nucleic acid sequence which encodes SEQ ID NO 9;
(c) a nucleic acid sequence which encodes an amino acid sequence which has greater than 85% identity to SEQ ID NO 10, wherein said identity can be determined using the DNAsis computer program and default parameters;
(d) a nucleic acid sequence which encodes amino acid sequence SEQ ID NO 10;
(e) a nucleic acid sequence which encodes an allelic variant of SEQ ID NO 10; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant integrase proteins comprising an amino acid sequence encoded by the above. Methods to impart agronomically-significant characteristics to at least one plant cell are also provided, comprising: contacting a plant integrase protein as described to at least one plant cell under conditions sufficient to allow a nucleic acid molecule to enter said cell, wherein said nucleic acid molecule encodes an agronomically-significant characteristic.

Plant reverse transcriptase sequences and constructs which comprise the sequences are provided, as are cells, seeds, embryos and plants comprising them. Preferred are isolated nucleic acid molecules, wherein said nucleic acid molecules encode at least a portion of a plant reverse transcriptase sequence and comprises a nucleic acid sequence selected from the group consisting of:
(a) a nucleic acid sequence which has more than 90% identity to SEQ ID NO 11, wherein said identity can be determined using the DNAsis computer program and default parameters;
(b) a nucleic acid sequence which encodes SEQ ID NO 11;
(c) a nucleic acid sequence which encodes an amino acid sequence which has greater than 85% identity to SEQ ID NO 12, wherein said identity can be determined using the DNAsis computer program and default parameters;
(d) a nucleic acid sequence which encodes amino acid sequence SEQ ID NO 12;
(e) a nucleic acid sequence which encodes an allelic variant of SEQ ID NO 12; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant reverse transcriptase proteins comprising an amino acid sequence encoded by the above. Methods to impart agronomically-significant characteristics to at least one plant cell are also provided, comprising: contacting a plant reverse transcriptase protein as described to at least one plant cell under conditions sufficient to allow a nucleic acid molecule to enter said cell, wherein said nucleic acid molecule encodes an agronomically-significant characteristic.

Plant RNAseH sequences and constructs which comprise the sequences are provided, as are cells, seeds, embryos and plants comprising them. Preferred are isolated nucleic acid molecules, wherein said nucleic acid molecules encode at least a portion of a plant RNAseH sequence and comprises a nucleic acid sequence selected from the group consisting of:
(a) a nucleic acid sequence which has more than 90% identity to SEQ ID NO 15, wherein said identity can be determined using the DNAsis computer program and default parameters;
(b) a nucleic acid sequence which encodes SEQ ID NO 15;
(c) a nucleic acid sequence which encodes an amino acid sequence which has greater than 95% identity to SEQ ID NO 16, wherein said identity can be determined using the DNAsis computer program and default parameters;
(d) a nucleic acid sequence which encodes amino acid sequence SEQ ID NO 16;
(e) a nucleic acid sequence which encodes an allelic variant of SEQ ID NO 16; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant RNAseH proteins comprising an amino acid sequence encoded by the above. Methods to impart agronomically-significant characteristics to at least one plant cell are also provided, comprising: contacting a plant RNAseH protein as described to at least one plant cell under conditions sufficient to allow a nucleic acid molecule to enter said cell, wherein said nucleic acid molecule encodes an agronomically-significant characteristic.

Plant retroelement sequences and constructs which comprise the sequences are provided, as are cells, seeds, embryos and plants comprising them. Preferred are isolated nucleic acid molecules, wherein said nucleic acid molecules encode at least a portion of a plant retroelement sequence and comprises a nucleic acid sequence selected from the group consisting of:
(a) a nucleic acid sequence which has more than 95% identity to a nucleic acid sequence selected from the group consisting of: SEQ ID NO 2; SEQ ID NO 5; SEQ ID NO 7; SEQ ID NO 9; SEQ ID NO 1; SEQ ID NO 13; SEQ ID NO 15; and SEQ ID NO 17, wherein said identity can be determined using the DNAsis computer program and default parameters;
(b) a nucleic acid sequence which is selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17;
(c) a nucleic acid sequence which encodes an amino acid sequence which has more than 90% identity to an amino acid sequence selected from the group consisting of SEQ ID NO 4; SEQ ID NO 6; SEQ ID NO 8; SEQ ID NO 10; SEQ ID NO 12; SEQ ID NO 14; SEQ ID NO 16; SEQ ID NO 18, wherein said identity can be determined using the DNAsis computer program and default parameters;
(d) a nucleic acid sequence which encodes an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18;
(e) a nucleic acid sequence which encodes an allelic variant of an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18; and
(f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Nucleic acid molecule as above, which further comprises at least one nucleic acid sequence which encodes at least one agronomically-significant characteristic are preferred. More preferred are those nucleic acid molecules as described wherein the agronomically-significant characteristic is selected from the group consisting of: male sterility; self-incompatibility; foreign organism resistance; improved biosynthetic pathways; environmental tolerance; photosynthetic pathways; and nutrient content. Also more preferred are those isolated nucleic acid molecule as described, wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Seeds and plants comprising a nucleic acid molecule as described are also preferred. More preferred are plants as described, wherein the plant is selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower; peanut; and olive. Most preferred are plants as described which is a soybean plant.

Plant retroelements comprising an amino acid sequence encoded by a nucleic acid sequence described are also provided. Plant cells comprising a nucleic acid molecule described herein, as well as plant retroviral proteins encoded by nucleic acid molecules described herein are provided.

Moreover, methods to transfer nucleic acid into a plant cell, comprising contacting a nucleic acid molecule of the present invention with at least one plant cell under conditions sufficient to allow said nucleic acid molecule to enter at least one cell of said plant are provided. In particular there is provided, methods to impart agronomically-significant characteristics to at least one plant cell, comprising: contacting a plant retroelement of the present invention to at least one plant cell under conditions sufficient to allow a nucleic acid molecule to enter said cell, wherein said nucleic acid molecule encodes an agronomically-significant characteristic. Methods as described, wherein the agronomically-significant characteristic is selected from the group consisting of: male sterility; self-incompatibility; foreign organism resistance; improved biosynthetic pathways; environmental tolerance; photosynthetic pathways; and nutrient content are preferred, as are methods wherein the agronomically-significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); anino acid content, and fatty acid content.

Plant retroelement sequences comprising specialized signals, and constructs which comprise the sequences are provided, as are cells, seeds, embryos and plants comprising them. Preferred are isolated nucleic acid molecules, comprisng a nucleic acid sequence selected from the group consisting of:
(a) a nucleic acid sequence which has more than 95% identity to SEQ ID NO 2; wherein said identity can be determined using the DNAsis computer program and default parameters;
(b) a nucleic acid sequence which is SEQ ID NO 2;
(c) a nucleic acid sequence which encodes amino acid sequence SEQ ID NO 4; and
(d) a nucleic acid sequence fully complementary to a nucleic acid sequence selected from the group consisting of: a nucleic acid sequence of (a); a nucleic acid sequence of (b); and a nucleic acid sequence of (c).

Plant retroelements as described above, which further comprise at least one nucleic acid sequence which encodes at least one agronomically-significant characteristic are preferred. More preferred are those methods wherein the agronomically-significant characteristic is selected from the group consisting of: male sterility; self-incompatibility; foreign organism resistance; improved biosynthetic pathways; environmental tolerance; photosynthetic pathways; and nutrient content or those wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Preferred are plant retroviral particles comprising an isolated retroelement as described, and seeds and plants comprising the retroelements as described. More preferred plants include soybean; maize; sugar cane; beet; tobacco;

wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower; peanut; and olive. Soybean is most preferred.

Also provided are methods to transfer nucleic acid into a plant cell, comprising contacting a plant retroelement as described with at least one plant cell under conditions sufficient to allow said plant retroelement to enter said cell. Methods to impart agronomically-significant characteristics to a plant, comprising contacting a plant retroelement as described with at least one plant cell under conditions sufficient to allow said plant retroelement to enter said cell are also preferred. Those methods wherein the plant retroelement is contacted with said cell via a plant retroviral particle described herein are preferred.

Plant retroviruses are also provided. In particular, plant retroviral particles comprising a plant-derived retrovirus envelope protein are provided. Plant retroviral particles comprising a plant-derived retrovirus envelope protein and which further comprise a plant retroviral protein selected from the group consisting of: plant-derived integrase; plant derived reverse transcriptase; plant-derived gag; and plant-derived RNAseH are preferred.

Plant retroviral particles comprising specialized retroviral proteins, and cells, seeds, embryos and plants which comprise the retroviral particles are provided. Preferred are isolated retroviral particles comprising a plant retroviral protein encoded by a nucleic acid sequence selected from the group consisting of:

(a) a nucleic acid sequence comprising (i) a nucleic acid sequence which encodes at least one plant retroviral envelope protein, and (ii) a nucleic acid sequence which has more than 60% identity to a nucleic acid sequence selected from the group consisting of: SEQ ID NO 9; SEQ ID NO 11; SEQ ID NO 15; SEQ ID NO 26; SEQ ID NO 27; SEQ ID NO 28; SEQ ID NO 29; SEQ ID NO 30; and SEQ ID NO 31, wherein said identity can be determined using the DNAsis computer program and default parameters;

(b) a nucleic acid sequence which encodes an amino acid sequence encoded by a nucleic acid sequence (a);

(c) a nucleic acid sequence which encodes an allelic variant of an amino acid sequence encoded by a nucleic acid sequence of (a); and (d) a nucleic acid sequence fully complementary to a nucleic acid sequence selected from the group consisting of: a nucleic acid sequence of (a); a nucleic acid sequence of (b); and a nucleic acid sequence of (c).

In particular, there are provided plant retroviral particles, wherein said nucleic acid sequence as described in (a) comprises a plant envelope nucleic acid specifically mentioned in claim 6 is preferred. Those particles which further comprise at least one nucleic acid sequence which encodes at least one agronomically-significant characteristic are preferred.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

More preferred are isolated retroviral particles comprising a plant retroviral protein encoded by a nucleic acid sequence selected from the group consisting of:

(a) a nucleic acid sequence which has more than 80% identity to a nucleic acid sequence selected from the group consisting of: SEQ ID NO 9; SEQ ID NO 11; and SEQ ID NO 15, wherein said identity can be determined using the DNAsis computer program and default parameters;

(b) a nucleic acid sequence which encodes a nucleic acid selected from the group consisting of: SEQ ID NO 9; SEQ ID NO 11; and SEQ ID NO 15;

(c) a nucleic acid sequence which encodes an amino acid sequence encoded by a nucleic acid sequence selected from the group consisting of: a nucleic acid sequence of (a); and a nucleic acid sequence of (b);

(d) a nucleic acid sequence which encodes an allelic variant of an amino acid sequence encoded by a nucleic acid selected from the group consisting of: a nucleic acid sequence of (a); and a nucleic acid sequence of (b); and (e) a nucleic acid sequence fully complementary to a nucleic acid sequence selected from the group consisting of: a nucleic acid sequence of (a); a nucleic acid sequence of (b); a nucleic acid sequence of (c); and a nucleic acid sequence of (d).

Nucleic acids as above, which further comprises at least one nucleic acid sequence which encodes at least one agronomically-significant characteristic are preferred. More preferred are those nucleic acids wherein the agronomically-significant characteristic is selected from the group consisting of: male sterility; self-incompatibility; foreign organism resistance; improved biosynthetic pathways; environmental tolerance; photosynthetic pathways; and nutrient content, or wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

Also preferred are isolated retroviral particles comprising a plant retroviral protein encoded by a nucleic acid sequence selected from the group consisting of:

(a) a nucleic acid sequence which has more than 60% identity to a nucleic acid sequence selected from the group consisting of SEQ ID NO 9; SEQ ID NO 11; SEQ ID NO 15; SEQ ID NO 26; SEQ ID NO 27; SEQ ID NO 28; SEQ ID NO 29; SEQ ID NO 30; and SEQ ID NO 31, wherein said identity can be determined using the DNAsis computer program and default parameters;

(b) a nucleic acid sequence which encodes a nucleic acid selected from the group consisting of: SEQ ID NO 9; SEQ ID NO 11; SEQ ID NO 15; SEQ ID NO 26; SEQ ID NO 27; SEQ ID NO 28; SEQ ID NO 29, SEQ ID NO 30, and SEQ ID NO 31;

(c) a nucleic acid sequence which encodes an amino acid sequence encoded by a nucleic acid sequence selected from the group consisting of: a nucleic acid sequence of (a); and a nucleic acid sequence of (b);

(d) a nucleic acid sequence which encodes an allelic variant of an amino acid sequence encoded by a nucleic acid selected from the group consisting of: a nucleic acid sequence of (a); and a nucleic acid sequence of (b); and (e) a nucleic acid sequence fully complementary to a nucleic acid sequence selected from the group consisting of: a nucleic acid sequence of (a); a nucleic acid sequence of (b); a nucleic acid sequence of (c); and a nucleic acid sequence of (d).

Also preferred are isolated retroviral particles comprising a plant retroviral sequence encoded by a nucleic acid sequence selected from the group consisting of:

(a) a nucleic acid sequence which has more than 80% identity to a nucleic acid sequence selected from the group consisting of SEQ ID NO 1; SEQ ID NO 2; SEQ ID NO 3, wherein said identity can be determined using the DNAsis computer program and default parameters;

(b) a nucleic acid sequence which encodes a nucleic acid selected from the group consisting of: SEQ ID NO 1; SEQ ID NO 2; and SEQ ID NO 3;

(c) a nucleic acid sequence which encodes SEQ ID NO 4;

(d) a nucleic acid sequence which encodes an amino acid sequence encoded by a nucleic acid sequence selected from the group consisting of: a nucleic acid sequence of (a); a nucleic acid sequence of (b); and a nucleic acid sequence of (c);

(e) a nucleic acid sequence which encodes an allelic variant of an amino acid sequence encoded by a nucleic acid selected from the group consisting of: a nucleic acid sequence of (a); a nucleic acid sequence of (b); and a nucleic acid sequence of (c) and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (e); and a nucleic acid sequence of (f).

Plant retroviral particles as described above, which further comprises an envelope-encoding nucleic acid sequence specifically described herein are preferred. Preferred are those retroviral particles which further comprise at least one nucleic acid sequence which encodes at least one agronomically-significant characteristic.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

Also provided, as part of the present invention, are isolated nucleic acid having at least 20 contiguous nucleotides of the sequence shown in SEQ ID NO 17. "At least" means that this is the lower limit and the number can be any whole number increment up to the total number of bases in SEQ ID NO 17. For example, isolated nucleic acid sequences which are 25, 30, 35, 40, 45, 50, 55, 60, 65 and 70 are within the scope of the present invention.

The following paragraph is designed to elaborate on the best mode and is not indicative of the sole means for making and carrying out the present invention. This paragraph is not intended to be limiting. The best way to make the present nucleic acids is to clone the nucleic acids from the respective organisms or amplified from genomic cDNA by the polymerase chain reaction using appropriate primers. The best way to make the present retroelements is to assemble the nucleic acids using standard cloning procedures. Transcriptional controls can be manipulated by inserting enhancers in or near the 5' LTR. Marker genes or genes of interest can be inserted within the retroelement. The best way to make the present retroviral particles is to express the retroelement, preferrably at high levels, in plant cells and the particles harvested by sucrose gradient fractionation. The best way to use the present nucleic acids is by allowing retroviral particles to come into contact with plant cells. Expression of marker genes carried by the retroelement can be used as one measure of infection and integration.

The following examples are not intended to limit the scope of the present invention as described and claimed. They are simply for the purpose of illustration.

EXAMPLES

Example 1

Characterizing the Arabidopsis Retroelements ("Tat" and "Athila" Elements)

Plant material and Southern hybridizations: The Arabidopsis Information Service supplied the following seed stocks (Kranz and Kirchheim (1987) Arabidopsis Inform. Serv. 24): Col-0, La-0, Kas-1, Co-4, Sei-0, Mv-0, Ll-0, Cvi-0, Fi-3, Ba-1, Hau-0, Aa-0, Ms-0, Ag-0, Ge-0, No-0 and Mh-0. Genomic DNA was extracted using Qiagen genoric tips and protocols supplied by Qiagen. For Southern hybridizations, the resulting DNA was digested with EcoRI, electrophoresed on 0.8% agarose and transferred to Gene Screen Plus membranes using the manufacturer's alkaline transfer protocol (New England Nuclear). All hybridizations were performed as described. Church and Gilbert (1984) Proc. Natl. Acad. Sci. USA 81: 1991–1995.

Library screening, probe preparation and PCR: Tat1 clones were obtained by screening a Landsberg erecta (La-0) 1 phage library (Voytas et al. (1990) Genetics 126: 713–721), using a probe derived by PCR amplification of La-0 DNA. The primers for probe amplification were based on the three published Tat1 sequences (DVO158, 5'-GGGATCCGCAATTAGAATCT-3'; DVO159, 5'-CGAATTCGGTCCACTTCGGA-3'). Peleman et al. (1991) Proc. Natl. Acad. Sci. USA 88: 3618–3622. Subsequent probes were restriction fragments of cloned Tat1 elements, and all probes were radiolabeled by random priming (Promega). Long PCR was performed using the Expand Long Template PCR System (Boehringer Mannheim) with LTR-specific primers (DVO354, 5'-CCACAAGATTCTAATTGCGGATTC-3'; DVO355, 5'-CCGAAATGGACCGAACCCGACATC-3'). The protocol used was for PCR amplification of DNA up to 15 kb. The following PCR primers were used to confirm the structure of Tat1-3: DVO405 (5'-TTTCCAGGCGTTACGAGATTTG-3') for the 3' non-coding region, DVO385 (5'-CGACTCGAGCTCCATAGCGATG-3') for the second ORF of Tat1-3 (note that the seventh base was changed from an A to a G to make an XhoI and a SalI restriction site) and DVO371 (5'-CGGATTGGGCCGAAATGGACCGAA-3') for the 3' LTR.

DNA sequencing: Clones were sequenced either by the DNA sequencing facility at Iowa State University or with the fmol sequencing kit (Promega). DNA from the 1 phage clones was initially subcloned into the vector pBluescript II KS- and transformed into the E. coli host strain XL1 Blue (Stratagene). AUSUBEL et al. (1987) Current Protocols in Molecular Biology. Greene/Wiley Interscience, New York. Subclones in the vector pMOB were used for transposon mutagenesis with the TN 1000 sequencing kit (Gold Biotechnologies). Transposon-specific primers were used for DNA sequencing reactions.

Sequence analysis: Sequence analysis was performed using the GCG software package (Devereux et al. (1984) Nucl. Acids Res. 12: 387–395), DNA Strider 1.2 (Marck (1991) DNA Strider 1.2, Gif-sur-Yvette, France), the BLAST search tool (Altschul et al. (1990) J. Mol. Biol. 215: 403–410) and the tRNAscan-SE 1.1 program (Lowe and Eddy (1997) Nucl. Acids Res. 25: 955–964). Phylogenetic relationships were determined by the neighbor-joining distance algorithm using Phylip (Felsenstein (1993) PHYLIP (Phylogeny Inference Package). Department of Genetics, University of Washington, Seattle; SAITOU and NEI (1987) Mol. Biol. Evol. 4: 406–425) and were based on reverse transcriptase amino acid sequences that had been aligned with ClustalW1.7. THOMPSON, et al. (1994) Nucl. Acids Res. 22: 4673–4680. Transmembrane helices were identified using the PHDhtm program. ROST et al. (1995) Prot. Science 4: 521–533. All DNA sequences have been submitted to the DDBS/EMBL/GenBank databases under the accession numbers X12345, X23456, X34567 and X45678.
Results Tat1 is a retrotransposon: Tat1 insertions share features with retrotransposon solo LTRs. We reasoned that if Tat1 is a retrotransposon, then there should be full-length elements in the genome consisting of two Tat1 sequences flanking an internal retrotransposon coding region. To test this hypothesis, additional Tat1 elements were isolated by screening a Landsberg (La-0) genomic DNA library with a Tat1 probe. Twenty-one 1 phage clones were isolated and Southern analysis revealed two clones (pDW42 and pDW99) each with two copies of Tat1 (data not shown). The two Tat1 elements in each clone were sequenced, along with the intervening DNA. All Tat1 sequences shared >89% nucleotide identity to the previously characterized Tat1a–Tat1c elements. Peleman et al. (1991) Proc. Natl. Acad. Sci. USA 88: 3618–3622. In clone pDW99, the 5' and 3' Tat1 sequences were 433 bases in length and only differed at two base positions. These Tat1 sequences also had conserved features of LTRs, including the dinucleotide end-sequences (5' TG-CA 3') that were part of 12 base inverted terminal repeats. If the two Tat1 elements in clone pDW99 were retrotransposon LTRs, then both, along with the intervening DNA, should be flanked by a target site duplication. A putative five base target site duplication (TATGT) was present immediately adjacent to the 5' and 3' Tat1 elements, supporting the hypothesis that they and the intervening DNA inserted as a single unit. In clone pDW42, the 5' Tat1 was 432 bases in length and shared 98% nucleotide sequence identity to the 3' Tat1. The last ~74 bases of the 3' Tat1 was truncated during library construction and lies adjacent to one phage arm. A target site duplication, therefore, could not be identified in this clone.

DNA sequences were analyzed for potential coding information between the 5' and 3' Tat1 elements. Nearly identical ORFs of 424 and 405 amino acids were found encoded between the Tat1 sequences in pDW42 and pDW99, respectively. The derived amino acid sequences of these ORFs were used to search the DNA sequence database with the BLAST search tool, and significant similarity was found to the Zea mays retrotransposable element Zeon-1 (p=4.4e-08). HU et al. (1995) Mol. Gen. Genet. 248: 471–480. The ORFs have ~44% similarity across their entirety to the 628 amino acid ORF encoded by Zeon-1 (see below). The Zeon-1 ORF includes a zinc finger motif characteristic of retrotransposon gag protein RNA binding domains. Hu et al. (1995) Mol. Gen. Genet. 248: 471–480. Although the Tat1 ORFs do not include the zinc finger motif, the degree of similarity suggests that they are part of a related gag protein.

If the Tat1 sequences in pDW42 and pDW99 defined retrotransposon insertions, a PBS would be predicted to lie adjacent to the 5' Tat1 elements in both clones. The putative Tat1 PBS shares similarity with PBSs of Zeon-1 and another maize retrotransposon called Cinful (see below), but it is not complementary to an initiator methionine tRNA as is the case for most plant retrotransposons. Additionally, a possible polypurine tract (PPT), the primer for second strand cDNA synthesis, was observed one base upstream of the 3' Tat1 sequence in both phage clones (5'-GAGGACTTGGGGGGCAAA-3'). We concluded from the available evidence that Tat1 is a retrotransposon, and we have designated the 3960 base insertion in pDW42 as Tat1-1 and the 3879 base insertion in pDW99 as Tat1-2. It is apparent that both Tat1-1 and Tat1-2 are non-functional. Their ORFs are truncated with respect to the coding information found in transposition-competent retrotransposons, and they lack obvious pol motifs.

In light of our findings, the previously reported Tat1 sequences can be reinterpreted. Tat1a and Tat1b, which are flanked by putative target site duplications, are solo LTRs. Tat1c, the only element without a target site duplication, is actually the 5' LTR and part of the coding sequence for a larger Tat1 element.

Copy number of Tat1 among A. thaliana ecotypes: To estimate Tat1 copy number, the 5' LTR, gag and the 3' non-coding region were used as separate probes in Southern hybridizations. The Southern filters contained genomic DNA from 17 ecotypes representing wild populations of A. thaliana from around the world. This collection of ecotypes had previously been used to evaluate retrotransposon population dynamics. Konieczny et al. (1991) Genetics 127: 801–809; Voytas et al. (1990) Genetics 126: 713–721; Wright et al. (1996) Genetics 142: 569–578. Based on the hybridization with the gag probe, element copy number ranges from two to approximately ten copies per ecotype. The copy number of the LTRs is higher, likely due to the presence of two LTRs flanking full-length elements or solo LTRs scattered throughout the genome. The Tat1 copy number contrasts with the copy numbers (typically less than three per ecotype) observed for 28 other A. thaliana retrotransposon families. Konieczny et al. (1991) Genetics 127: 801–809; Voytas et al. (1990) Genetics 126: 713–721; Wright et al. (1996) Genetics 142: 569–578. In addition, the Tat1-hybridizing restriction fragments are highly polymorphic among strains. This degree of polymorphism, coupled with the high copy number, suggested that Tat1 has been active in transposition since the separation of the ecotypes.

The Tat1-3' non-coding region contains DNA sequences from elsewhere in the genome: In an attempt to identiiy a complete and functional Tat1 element, LTR-specific primers were used in PCR reactions optimized for amplification of large DNA fragments. Most full-length retrotransposable elements are between five and six kb in length. DNAs from all 17 ecotypes were used as templates, and each gave amplification products of ~3.2 kb, the size predicted for Tat1-1 and Tat1-2 (data not shown). In La-0, however, a 3.8 kb PCR product was also recovered. This PCR product was cloned, sequenced and called Tat1-3. This insertion is expected to be about 4.6 kb in total length if the LTR sequences are included.

Tat1-3 differed from Tat1-1 and Tat1-2 in that it had two ORFs separated by stop codons and a 477 base insertion in the 3' non-coding region. The first ORF (365 amino acids) was similar to but shorter than the ORFs of the other Tat1 elements. The sequences constituting the second ORF (188 amino acids) were not present in the other Tat1 insertions and were not related to other sequences in the DNA databases. Database searches with the 477 base insertion in the 3' non-coding region, however, revealed three regions of similarity to other genomic sequences. A region of 113 bases matched a region of 26 bp repeats in the 5' untranslated sequence of the AT-P5C1 mRNA, which encodes pyrroline-5-carboxylate reductase (p=2.1e-19). Verbruggen et al. (1993) Plant Physiol. 103: 771–781. In addition, 50 bases appear to be a remnant of another retrotransposon related to Tat1. These 50 bases are 71% identical to the 3' end of the Tat1-3 LTR and the putative primer binding site. The putative primer binding site, however, is more closely related to those of other plant retrotransposons such as Huck-2 (Sanmiguel et al. (1996) Science 274: 765–768). Finally, sequences in the remainder of the insertion showed significant simlarity to a region on chromosome 5. To confirm that Tat1-3 was not a PCR artifact, two additional primer pairs were used in separate amplifications. Both amplifications gave PCR products of the predicted sizes, which were cloned and confirmed to be Tat1-3 by DNA sequencing.

PCR amplifications with the additional primer pairs also yielded a product 0.8 kb longer than that expected for Tat1-3. This product was cloned, sequenced and found to be another Tat1 element, designated Tat1-4. This element has sequences similar to a Tat1 LTR, polypurine tract and the second ORP of Tat1-3. In Tat1-4, 1182 bases of DNA are found in the 3' non-coding region at the position corresponding to the 477 base insertion in Tat1-3. This region does not match any sequences in the DNA databases.

Other Tat1-like elements in *A. thaliana*: A BLAST search of DNA sequences generated by the *A. thaliana* genome project identified two more solo LTRs similar to Tat1. All share similarities throughout, but most strikigly, they are very well conserved at the 5' and 3' ends where it is expected integrase would bind. Braiterman and Boeke (1994) Mol. Cell. Biol. 14: 5731–5740. These conserved end-sequences suggest that the integrases encoded by full-length elements are also related, and that the LTRs have evolved under functional constraints; that is, they are not simply degenerate Tat1 LTRs. The two new LTRs are designated as Tat2-1 and Tat3-1. Tat2-1 is 418 bases long, is flanked by a five base target site duplication (CTATT) and is ~63% identical to the Tat1-2 5' LTR. Tat3-1 is 463 bases long and is also flanked by a target site duplication (ATATT). Tat3-1 is ~53% identical to the Tat1-2 5' LTR.

Tat1 and Athila are related to Ty3/gypsy retrotransposons: Further analysis of data from the *A. thaliana* genome project revealed two slightly degenerate retrotransposons with similarity to the Tat1 ORF. These elements were identified within the sequence of the P1 phage clones MXA21 (Accession AB005247; bases 54,977–66,874) and MX110 (Accession AB005248; bases 24,125–35,848). Each has two LTRs, a putative PBS, and long ORFs between their LTRs. Amino acid sequence analysis indicated the presence of an RNA binding domain that defines gag in both elements. This region is followed by conserved reverse transcriptase, RNaseH, and integrase amino acid sequence domains characteristic of pol (data not shown). Classification of eukaryotic retrotransposons into the Ty1/copia elements (Pseudoviridae) and Ty3/gypsy elements (Metaviridae) is based on pol gene structure. Boeke et al. (1998) Metaviridae. In Virus Taxonomy: ICTV VIIth Report, edited by F. A. Murphy. Springer-Verlag, N.Y.; Boeke et al. (1998b) Pseudoviridae. In Virus Taxonomy: ICTV VIIth Report, edited by F. A. Murphy. Springer Verlag, N.Y. The domain order of the pol genes (reverse transcriptase precedes integrase ) and similarities among their encoded reverse transcriptases (see below) identifies these elements as the first full-length A. thaliana Ty3/gypsy elements.

Because the characterized Tat1 insertions do not encode pol genes, this element family could not be classified. However, the amino acid sequence of the Tat1-2 ORF is 51% similar to the gag region of the MXA21 retrotransposon. Since plant retrotransposons within the Ty1/copia or Ty3/gypsy families, even those with highly similar pol genes, share little amino acid sequence similarity in their gag regions, Tat1 is likely a Ty3/gypsy element. This conclusion is further supported by the report that the Tat-like Zeon-1 retrotransposon is very similar to a *Z. mays* Ty3/gypsy element called cinful (Bennetzen (1996) Trends Microbiol. 4: 347–353); however, only the 5' LTR and putative primer binding site (PBS) sequences are available in the sequence database for analysis (Accession U68402). Because of the extent of similarity to Tat1, we have named the MXA21 insertion Tat4-1.

The gag region of the MX110 element is 62% similar (p=1.1e-193) to the first ORF of Athila, which has previously been unclassified (Pelissier et al. (1995) Plant Mol. Biol. 29: 441 452). This implies that Athila is also a Ty3/gypsy element, and we have designated the MX110 insertion as Athila1-1. Our classification of Athila as a Ty3/gypsy element is further supported by the observation that the Athila gag amino acid sequences shares significant similarity to the gag protein encoded by the cyclops-2 Ty3/gypsy retrotransposon of pea (Accession AJ000640; p=1.1e-46; data not shown). Further analysis of the available *A. thaliana* genome sequences identified three additional Athila homologs. They include an additional Athilal element, designated Athila1-2, and two more distantly related Athila-like elements, designated Athila2-1 and Athila3-1.

In addition to similarities among their gag amnino acid sequences, the Tat elements have short LTRs (<550 bp) and long 3' non-coding regions (>2 kb). In contrast, the Athila-like elements have long LTRs (>1.2 kb) and are very large retrotransposons (>11 kb). One additional feature to note about both the Athila-like and Tat-like elements is the high degree of sequence degeneracy of their internal coding regions. This contrasts with the near sequence identity of their 5' and 3' LTRs, which is typically greater than 95%. Because a single template is used in the synthesis of both LTRs, LTR sequences are usually identical at the time of integration. The degree of sequence similarity between the LTRs suggests that most elements integrated relatively recently. The polymorphisms observed in the internal domains of these insertions, therefore, may have been present in their progenitors, and these elements may have been replicated in trans.

A novel, conserved coding region in Athila elements: A surprising feature of Athila1-1 is the presence of an additional ORP after integrase. Like gag, this ORF shares significant similarity across its entirety (p=3.8e-08) to the second ORF of Athila. This ORF is also encoded by the Athila2-1 and Athila3-1 elements, although it is somewhat more degenerate. The presence of this coding sequence among these divergent retrotransposons suggests that it plays a functional role in the element replication cycle. However, the ORF shows no similarity to retrotransposon gag or pol genes. The retroviruses and some Ty3/gypsy retrotransposons encode an env gene after integrase.

Although not well-conserved in primary sequence, both viral and retrotransposon envelope proteins share some structural similarities. They are typically translated from spliced mRNAs and the primary translation product encodes a signal peptide and a transmembrane domain near the C-terminus. All four families of Athila elements encode a domain near the center of the ORF that is strongly predicted to be a transmembrane region (70%–90% confidence, depending on the element analyzed) (ROST et al. (1995) Prot. Science 4: 521–533). Two retrotransposons, Athila and Athila2-1, also have a hydrophobic transmembrane domain near the 5' end of their env-like ORFs, which may serve as a secretory signal sequence. Von Heijne (1986) Nucl. Acids Res. 14: 4683–4690.

Two lineages of plant Ty3/gypsy retrotransposons: Relationships among Ty3/gypsy retrotransposons from *A. thaliana* and other organisms were assessed by constructing a neighbor-joining tree of their reverse transcriptase amino acid sequences. Included in the analysis were reverse transcriptases from two additional families of *A. thaliana* Ty3/gypsy elements that we identified from the unannotated genome sequence data (designated Tma elements; Tma1-1 and Tma3-1); two other Tma element families were identified in the genome sequence that did not encode complete reverse transcriptases (Tma2-1 and Tma4-1; Table 1). Also included in the phylogenetic analyses were reverse transcriptases from a faba bean retrotransposon and the cyclops-2 element from pea. The plant Ty3/gypsy group retrotransposons resolved into two lineages: One was made up of dell from lily, the IFG7 retrotransposon from pine, reina from *Z. mays,* and Tma1-1 and Tma3-1. This group of elements formed a single branch closely related to numerous fungal retrotransposons (branch 1). The second branch (branch 2) was well-separated from all other known Ty3/gypsy group elements, and was further resolved into two lineages: Athila1-1, cyclops-2 and the faba bean reverse transcriptase formed one lineage (the Athila branch), and Tat4-1 and Grande1-4 from Zea diploperennis formed a separate, distinct branch (the Tat branch).

Primer binding sites: Most plant Ty1/copia retrotransposons as well as the branch 1 Ty3/gypsy elements have PBSs complementary to the 3'-end of an initiator methionine tRNA. This is not the case for any of the branch 2 Ty3/gypsy elements. We compared the putative PBSs of Tat-branch and Athila-branch elements to known plant tRNA genes as well as to the 11 tRNA genes that had been identified to date in sequences generated by the *A. thaliana* genome project. In addition, we searched the unannotated *A. thaliana* genome sequences and identified 30 more *A. thaliana* tRNA genes using the program tRNAscan-SE (Lowe and Eddy (1997) Nucl. Acids Res. 25: 955–964). The PBS of Tat1 is complementary to 10 bases at the 3' end of the asparagine tRNA for the AAC codon; these 10 bases are followed by a two base mismatch and six additional bases of perfect complementarity. The Tat4-1 PBS is complementary to 20 bases at the 3' end of the arginine tRNA for the AGG codon with one mismatch 10 bases from the 3' end; Huck-2, Grande-zm1, Grande1-4, and the retrotransposon-like insertion in the 3' non-coding region of Tat1-3 al have 20-base perfect complementarity to this tRNA. The PBS of Athila1-1 is perfectly complementary to 15 bases at the 3' end of the aspartic acid tRNA for the GAC codon, and Athila and Athila2-1 have 13 bases of complementarity to this tRNA. At this time there is no known plant tRNA complementary to the PBS of Zeon-1, which has the same PBS as the maize retrotransposon cinful. As more tRNA sequences become available, a candidate primer may be identified for these elements.

Example 2

Characterizing the *Pisum sativum* Retroelement ("Cyclops" Element) Env Gene

After identifying the retrovirus-like elements in *A. thaliana,* the element called Cyclops2 from *Pisum sativum* (Chavanne et al. (1998) Plant Mol. Biol. 37:363–375) was examined. Comparison of this element to the Athila-like elements both in size and amino acid and nucleotide sequence composition was made. Cyclops2 also encodes an open reading frame (ORF) in the position corresponding to the env-like gene of the Athila elements. This Cyclops2 ORF was examined using the same methods used to characterize the Athila group env-like genes (see Example 1). The Cyclops2 ORF was found to have a potential splice site at its N-terminus and transmembrane domains at the N-temiinus, the central region and the C-terminus. Based on the presence of these features, it was concluded that Cyclops2 is a retrovirus-like retroelement that encodes on env-like gene.

Example 3

Obtaining the Soybean Retroelements ("Calypso" Elements)

Materials and Methods

Library Screening and Southern Hybridization. A soybean genomic lambda phage library (line L85-3044) was initially screened with a reverse transcriptase probe under low stringency conditions (50 degrees Celsius with a 1% SDS wash) (Church and Gilbert (1984) Proc. Natl. Acad. Sci. USA 81:1991–1995). The library was previously described (Chen et al. (1998) Soybean Genetics Newsletter 25:132–134). The probe was obtained by PCR amplification of genomic *P. sativum* DNA using primers based on the reverse transcriptase of Cyclops2 (DVO701 and DV702). All probes were radio-labeled using random primers and protocols supplied by Promega (Madison, Wis.). For Southern hybridizations, DNA was digested, electrophoresed on 0.8% agarose gels, and transferred to Gene Screen Plus membranes using the manufactureris alkaline transfer protocol (New England Nuclear, Boston, Mass.). All high stringency hybridizations were as described (Church and Gilbert (1984) Proc. Natl. Acad. Sci. USA 81:1991–1995).

DNA sequencing. Lambda phage clones were subcloned into the vector pBluescript KSII—and transformed into the *E.coli* host strain XL1 Blue (Stratagene, La Jolla, Calif.) (Ausubel et al., Current Protocols in Molecular Biology (Greene Publishing Associates, Inc., 1993). Subclones were sequenced by primer walking at the Iowa State University DNA sequencing facility.

Sequence Analysis. DNA Sequence analysis was performed using the GCG software package (Devereux et al. (1984) Nucleic Acids Res. 12:387–395), DNA Strider 1.2 (Marck (1991) DNA Strider 1.2, Gif-sur-Yvette, France) and the BLAST search tool (Altschul et al. (1990) J. Mol. Biol. 215: 403–410). Phylogenetic relationships were determined by the neighbor-joining distance algorithm (Saitou and Nei (1987) Mol. Biol. Evol. 4: 406–425) using PAUP v4.0 beta 1 (Swofford (1993) Illinois Natural History Survey, Champaign, Ill.) and were based on reverse transcriptase amino acid sequences that had been aligned with ClustalX v1.63b (Thompson et al. (1994) Nucl. Acids Res. 22: 4673–4680). Transmembrane helices were identified using the PHDhtm program and TMPred (Rost et al. (1995) Prot. Science 4: 521–533; Hofmann and Stoffel (1993) Biol. Chem. 374:166).

Results

Retrovirus-like elements in Glycine max. Soybean retrovirus-like elements were identified by a low stringency (50 degrees C.) screen of a soybean lambda library using a reverse transcriptase probe. The probe was based on a sequence from Cyclops2 (Chavanne et al. (1998) Plant Mol. Biol. 37:363–375). The screen produced 63 lambda clones that appeared to contain a retrovirus-like reverse transcriptase based on hybridization to the probe. Thirty-five of these putative elements were sequenced to varying degrees and 24 encoded readily identifiable retrovirus-like sequences. Most of the elements were distantly related and had premature stop codons, frame shifts, deletions or insertions. A related group of three elements and another related pair were completely sequenced and analyzed. The three elements in the first group are referred to as Calypso1-1, Calypso1-2, and Calypso1-3. The elements in the second pair are referred to as Calypso2-1 and Calypso2-2. The remaining soybean retrovirus-like elements will be given the Calypso name and a sequential designator number based on their family grouping.

The Calypso retrovirus-like elements have the same overall structure and sequence homology as the previously described Athila and Cyclops elements. The elements are ~12 kb in length; they have a 5' LTR, a PBS (Primer Binding Site), a gag protein, a pol protein, a spacer, an env-like protein, another spacer region, a PPT (Polypurine Tract) and a 3' LTR. The LTRs vary from ~1.3 to ~1.5 kb in length and characteristically begin with TG and end with CA. The PBS is similar to that used by the Athila and Cyclops elements; it is 4 to 6 bases past the 5' LTR and matches the 3' end of a soybean aspartic acid tRNA for 18 to 19 bases with 1 mismatch. The fact that the sequences of the Calypso primer binding sites are shared with the *A. thaliana* and *P. sativum* retrovirus-like elements, indicates that this sequence is a unique marker for envelope-encoding retroelements. The gag protein extends ~850 amino acids and encodes a zinc finger domain (characterized by the amino acid motif CxxCxxxHxxxxC) and a protease domain (characterized by the amino acid motif LIDLGA). These domains are located at approximately the same positions witin gag as in other retroelements. The ~600 amino acid reverse transcriptase region follows gag and has the conserved plant retrovirus-like motifs which approximate the following amino acids: KTAF, MP/SFGLCNA, V/I/MEVFMDDFS/WV/I, FELMCDASDYAI/VGAVLGQR, and YATT/IEKEL/MLAIVF/YAL/FEKFR/KSYLI/VGSR/KV, respectively. The ~450 amino acid integrase domain has the plant retrovirus-like integrase motifs that approximate HCHxSxxGGH30xCDxCQR for the Zn finger as well as two other motifs that approximate WGIDFI/V/MGP, and PYHPQTxGQA/VE. After integrase, there is a ~0.7 kb spacer then a ~450 amino acid env-like protein coding region. The env-like protein of the Calypso elements is well conserved through most of the ORF but conservation decreases toward the C-terminus. The conservation includes 2 or 3 presumed transmembrane domains and a putative RNA splice site acceptor. The env-like protein is followed by a ~2 kb spacer then a Polypurine tract with the approximate sequence ATTTGGGGG/AANNT. The 3' LTR starts immediately after the final T of the PPT.

Calypso elements are abundant and heterogeneous. The Calypso elements appear to be abundant in the soybean genome. High stringency Southern blots of soybean DNA probed with reverse transcriptase, gag or env-like sequences produced smeared hybridization patterns, suggesting that the elements are abundant and heterogeneous. Their heterogeneity was also supported by DNA sequence analysis, which revealed a maximum of 93% nucleotide identity among elements, and most elements averaged ~88% nucleotide identify. This identity can be region-specific or dispersed over the element's entirety. For example, reverse transcriptase, integrase and envelope-like coding regions may be well conserved, whereas the LTR, gag and spacer regions may have very little sequence conservation.

Phylogenetic analysis of Calypso reverse transcriptase. The reverse transcriptase of retroelements is the preferred protein for assessment of phylogenetic relationships (Xiong and Eickbush (1990) EMBO J. 9:3353–3362). This is due to the high degree of amino acid sequence conservation found in reverse transcriptase proteins from many sources. The Calypso retrovirus-like elements were compared to previously described Ty3/gypsy and retrovirus-like elements from plants, fungi and invertebrate animals. The Calypso elements formed a distinct group with other plant retrovirus-like elements from *A. thaliana* and *P. sativum* and Faba bean. This group did not include plant Ty3/gypsy elements that are members of the metavirus genus. This indicates that the plant retrovirus-like elements from these four plant species are closely related and form a new element group that may be present in all or most plant species.

The Calypso reverse transcriptase and integrase are well-conserved. Frame shifts in the retrovirus-like elements were repaired through sequence comparison between the retrovirus-like elements from *A. thaliana*, *P. sativum* and *G. max*. Restoration typically involved an insertion or deletion of a single nucleotide or a single nucleotide substitution. When the edited ORFs of seven plant retrovirus-like elements from three species were compared, it was found that the gag domain had very little conservation. The amino acid sequence around the protease domain was reasonably conserved (~50%) but the reverse transcriptase and integrase domains were highly conserved (~70%).

The env-like ORF of Calypso is well-conserved. Animal retrovirus env proteins share little in common. They are however cleaved into two functional units that consist of the surface (SU) and transmembrane (In peptides. The SU peptide contains a transmembrane secretory signal at the N-terminus. The TM peptide has two transmembrane domains, one at the N-terminus, which functions in membrane fusion, and another near the C-terminus, which acts as an anchor site. The retrovirus env protein is expressed from an RNA that is spliced near the beginning of the env ORP. There are currently nine Athila group elements from *A. thaliana* that have an identifiable env-like ORF. Alignment of the env-like amino acid sequence shows that there are five subgroups of env-like proteins in the Athila family. Three are distinct, four are closely related and another pair is closely related. As a whole, these env-like sequences share limited homology over the entire length of the ORF, but within subgroups, they share high homology (data not shown). Some of the Athila env-like proteins have an apparent secretory peptide and a central transmembrane domain, suggesting that they may have an env-like function.

Among the Calypso elements, seven have been characterized that encode env-like ORFs. These env-like ORFs form four families that have a high degree of overall sequence similarity beginning at the first methionine and continuing for three quarters of the ORF; sequence similarity falls off dramatically near the C-terminus. The amino acid sequence at the first methionine has the consensus sequence QMASR/KKRR/KA, which appears to be a nuclear targeting signal, however, the program PSORT only predicts a 0.300 confidence level for this targeting role (Nakai and Horton (1999) Trends Biochem. Sci. 24:34–36). A similar sequence (ASKKRK) is found at the same position in the env-like ORF of Cyclops2, suggesting that it serves a similar purpose. No other potential targeting peptide stands out from the sequence that has been analyzed so far. There is a conserved region that is predicted to be a transmembrane domain near the center of the Calypso env-like protein and a second transmembrane domain located at variable positions near the C-terminus. These may be the fusion and anchor functions of a TM peptide. It should also be noted that five of the seven ORFs are predicted to have a transmembrane domain that is just before and includes the first methionine. This N-terminal transmembrane domain may be a secretory signal of an SU peptide. The program TMpred estimates these transmembrane domains to be significant based on a score >500 (Hofmann and Stoffel (1993) Biol. Chem. 374:166). These three transmembrane domains are found in the Cyclops2 env-like protein at similar locations but at a reduced significance score. Another feature of the Calypso env-like ORF is the conserved splice site that is predicted to be at the first methionine by the program NetGene2 v. 2.4 with a confidence level of 1.00 (Hebsgaard et al. (1996) Nucleic Acids Res. 24:3439–3452); Brunak et al. (1991) J. Mol. Biol 220:49–65). There are other less preferred putative splice sites in the region, but only the splice site near the methionine is optimally placed and conserved in all seven env-like ORFs.

Example 4

Obtaining the Generic Plant Retroelements ("Generic" Elements)

ClustalX v1.63b (Thompson et al. (1994) Nucl. Acids Res. 22: 4673–4680) was used to align nucleotide sequences of Calypso1-1 Calypso1-2 and Calypso1-3. A consensus sequence was generated from the ClustalX output. The consensus sequence file was then translated and compared using ClustalX to amino acid sequences of retrovirus-like elements from soybean, pea (Cyclops2) and *A. thaliana* (Athila-like elements) using the GCG computer software package (Devereux et al. (1984) Nucleic Acids Res. 12:387–395). For coding regions encompassing protease, reverse transcriptase and integrase, a new consensus sequence was generated that best matched the coding information in all elements. This second consensus sequence forms the protase, reverse transcriptase and integrase genes of the generic element. The gag gene of the generic element is a consensus sequence generated by editing alignments between Calypso1-1 and Calypso2-2. The env gene is a consensus sequence based on env gene sequence alignments of all Calypso elements. All non-coding regions for the generic element were obtained >from Calypso1-2, with the exception of the LTRs, which were taken from Calypso1-1.

A generic retrovirus will be constructed by first generating a DNA sequence that approximates the sequence of the generic element. An element that closely matches the consensus—for example, Calypso1-1—will be modified by PCR-based site-directed mutagenesis (Ausubel et al., Current Protocols in Molecular Biology (Greene Publishing Associates, Inc., 1993). Modifications will be sequentially introduced into the starting element until it conforms to the sequence of the generic element.

The generic element will be modified so that it will be expressed at high levels in plant cells. This will be accomplished by inserting an enhancer—such as the cauliflower mosaic virus 35S enhancer—into the 5' LTR. To monitor replication, a marker gene will be inserted into the virus between the end of the coding region for the env gene and the polypurine tract The marker gene may encode resistance to an herbicide or antibiotic. The modified generic element will then be introduced into plant cells by standard means of plant transformation. Because the modified generic element will be expressed at high levels, retroviral particles will be produced by the host plant cell. These will be harvested and purified by passing cell lysates over sucrose density gradients.

The plant retroviral particles will be incubated in the presence of non-transformed plant cells. The virus will associate with the plant cell and fuse with the plant cell membrane. The mRNA carried by the virus will be reverse transcribed and the resultant cDNA will be integrated into the genome of the plant. The integration of the viral DNA and the expression of the marker gene it carries will confer antibiotic resistance to the plant cell. Cells that carry integrated viruses can be identified through genetic selection.

Although the present invention has been fully described herein, it is to be noted that various changes and modifications are apparent to those skilled in the art Such changes and modifications are to be understood as included within the scope of the present invention as defined by the appended claims.

What is claimed is:

1. An isolated nucleic acid molecule, wherein said nucleic acid molecule encodes at least a portion of a plant retroelement and comprises a nucleic acid sequence selected from the group consisting of:

(a) a nucleic acid sequence which is at least a portion of a plant generic retroelement sequence and which has more than 50% identity to SEQ ID NO:17, wherein said identity can be determined using the DNAsis computer program and default parameters, and wherein said nucleic acid sequence has functional properties of a plant generic retroelement of SEQ ID NO: 17;

(b) the nucleic acid sequence of SEQ ID NO: 17;

(c) a nucleic acid sequence which encodes an amino acid sequence which has more than 40% identity to SEQ ID NO: 18, wherein said identity can be determined using the DNAsis computer program, and wherein said amino acid sequence has functional properties of the retroelement polypeptide of SEQ ID NO:18;

(d) a nucleic acid sequence which encodes the amino acid sequence of SEQ ID NO:18; and (e) a nucleic acid sequence fully complementary to a nucleic acid sequence selected from the group consisting of: a nucleic acid sequence of (a) a nucleic acid sequence of (b) a nucleic acid sequence of (c) a nucleic acid sequence of (d).

2. A seed comprising a nucleic acid of claim 1.

3. A plant comprising a nucleic acid of claim 1.

4. A nucleic acid molecule of claim 2, which further comprises SEQ ID NO:4.

5. An isolated nucleic acid having at least 20 contiguous nucleotides of the sequence shown in SEQ ID NO:17.

* * * * *

UNITED STATES PATENT AND TRADEMARK OFFICE
CERTIFICATE OF CORRECTION

PATENT NO. : 6,331,662 B1
DATED : December 18, 2001
INVENTOR(S) : David A. Wright and Daniel F. Voytas It is certified that error appears in the above-identified patent and that said Letters Patent is hereby corrected as shown below:

Column 125,
Line 11, insert -- g -- after "(a)", therefor.

Column 126,
Line 1, insert -- g -- after "(b)", therefor.
Line 1, insert -- g -- after "(c)", therefor.

Signed and Sealed this

Twenty-third Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,331,662 B1
DATED : December 18, 2001
INVENTOR(S) : David A. Wright and Daniel F. Voytas It is certified that error appears in the above-identified patent and that said Letters Patent is hereby corrected as shown below:

Column 125,
Line 11, after "(a)" and before "a" please remove "g" and insert -- , -- therefor.

Column 126,
Line 1, after "(b)" and before "a" please remove "g" and insert -- , -- therefor.
Line 1, after "(c)" and before "a" please remove "g" and insert -- , -- therefor.

Signed and Sealed this

Eighth Day of June, 2004

JON W. DUDAS
*Acting Director of the United States Patent and Trademark Office*

SEQUENCE LISTING

```
<160> NUMBER OF SEQ ID NOS: 41

<210> SEQ ID NO 1
<211> LENGTH: 18
<212> TYPE: DNA
<213> ORGANISM: Glycine max

<400> SEQUENCE: 1
tggcgccgtt gccaattg                                                 18

<210> SEQ ID NO 2
<211> LENGTH: 18
<212> TYPE: DNA
<213> ORGANISM: Glycine max

<400> SEQUENCE: 2
tggcgccgtt gtcgggga                                                 18
```

```
<210> SEQ ID NO 3
<211> LENGTH: 6
<212> TYPE: DNA
<213> ORGANISM: Glycine max

<400> SEQUENCE: 3 ttgggg                                                              6

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: plant
      retroelement sequence

<400> SEQUENCE: 4

Met Ala Ser Arg Lys Arg Lys
 1               5

<210> SEQ ID NO 5
<211> LENGTH: 1263
<212> TYPE: DNA
<213> ORGANISM: Artificial Sequence
<220> FEATURE:
<223> OTHER INFORMATION: Description of Artificial Sequence: plant
      retroelement sequence

<400> SEQUENCE: 5
atggcctccc gtaaacgcaa agctgtgccc acacccgggg aagcgtccaa ctgggactct    60
tcacgtttca ctttcgagat tgcttggcac agataccagg atagcattca gctccggaac   120
atccttccag agaggaatgt agagcttgga ccagggatgt tgatgagtt cctgcaggaa    180 ctccagaggc tcagatggga ccaggttctg acccgacttc agagaagtg gattgatgtt    240 gctctggtga aggagtttta ctccaaccta tatgatccag aggaccacag tccgaagttt    300
tggagtgttc gaggacaggt tgtgagattt gatgctgaga cgattaatga tttcctcgac    360
accccggtca tcttggcaga gggagaggat tatccagcct actctcagta cctcagcact    420
cctccagacc atgatgccat cctttccgct ctgtgtactc caggggacg atttgttctg     480 aatgttgata gtgccccctg gaagctgctg cggaaggatc tgatgacgct cgcgcagaca    540
tggagtgtgc tctcttattt taaccttgca ctgacttttc acacttctga tattaatgtt    600
gacagggccc gactcaatta tggcttggtg atgaagatgg acctggacgt gggcagcctc    660
atttctcttc agatcagtca gatcgcccag tccatcactt ccaggcttgg gttcccagcg    720
ttgatcacaa cactgtgtga gattcagggg gttgtctctg ataccctgat ttttgagtca    780
ctcagtcctg tgatcaacct tgcctacatt aagaagaact gctggaaccc tgccgatcca    840
tctatcacat ttcagggac ccgccgcacg cgcaccagag cttcggcgtc ggcatctgag     900
gctcctcttc catcccagca tccttctcag ccttttccc agagaccacg gcctccactt    960
ctatccacct cagcacctcc atacatgcat ggacagatgc tcaggtcctt gtaccagggt   1020
cagcagatca tcattcagaa cctgtatcga ttgtccctac atttgcagat ggatctgcca   1080
ctcatgactc cggaggccta tcgtcagcag gtcgccaagc taggagacca gccctccact   1140 gacaggggg aagagccttc tggagccgct gctactgagg atcctgccgt tgatgaagac   1200
ctcatagctg acttggctgg cgctgattgg agcccatggg cagacttggg cagaggcagc   1260
tga                                                                1263
```

```
<210> SEQ ID NO 6
<211> LENGTH: 421
<212> TYPE: PRT
<213> ORGANISM: Artificial Sequence
<220> FEATURE:
<223> OTHER INFORMATION: Description of Artificial Sequence: plant
      retroelement sequence

<400> SEQUENCE: 6

Met Ala Ser Arg Lys Arg Lys Ala Val Pro Thr Pro Gly Glu Ala Ser
 1               5                  10                  15

Asn Trp Asp Ser Ser Arg Phe Thr Phe Glu Ile Ala Trp His Arg Tyr
            20                  25                  30

Gln Asp Ser Ile Gln Leu Arg Asn Ile Leu Pro Glu Arg Asn Val Glu
         35                  40                  45

Leu Gly Pro Gly Met Phe Asp Glu Phe Leu Gln Glu Leu Gln Arg Leu
     50                  55                  60

Arg Trp Asp Gln Val Leu Thr Arg Leu Pro Glu Lys Trp Ile Asp Val
 65                  70                  75                  80

Ala Leu Val Lys Glu Phe Tyr Ser Asn Leu Tyr Asp Pro Glu Asp His
                 85                  90                  95

Ser Pro Lys Phe Trp Ser Val Arg Gly Gln Val Val Arg Phe Asp Ala
            100                 105                 110

Glu Thr Ile Asn Asp Phe Leu Asp Thr Pro Val Ile Leu Ala Glu Gly
        115                 120                 125

Glu Asp Tyr Pro Ala Tyr Ser Gln Tyr Leu Ser Thr Pro Pro Asp His
    130                 135                 140

Asp Ala Ile Leu Ser Ala Leu Cys Thr Pro Gly Gly Arg Phe Val Leu
145                 150                 155                 160

Asn Val Asp Ser Ala Pro Trp Lys Leu Leu Arg Lys Asp Leu Met Thr
                165                 170                 175

Leu Ala Gln Thr Trp Ser Val Leu Ser Tyr Phe Asn Leu Ala Leu Thr
            180                 185                 190

Phe His Thr Ser Asp Ile Asn Val Asp Arg Ala Arg Leu Asn Tyr Gly
        195                 200                 205

Leu Val Met Lys Met Asp Leu Asp Val Gly Ser Leu Ile Ser Leu Gln
    210                 215                 220

Ile Ser Gln Ile Ala Gln Ser Ile Thr Ser Arg Leu Gly Phe Pro Ala
225                 230                 235                 240

Leu Ile Thr Thr Leu Cys Glu Ile Gln Gly Val Val Ser Asp Thr Leu
                245                 250                 255

Ile Phe Glu Ser Leu Ser Pro Val Ile Asn Leu Ala Tyr Ile Lys Lys
            260                 265                 270

Asn Cys Trp Asn Pro Ala Asp Pro Ser Ile Thr Phe Gln Gly Thr Arg
        275                 280                 285

Arg Thr Arg Thr Arg Ala Ser Ala Ser Ala Ser Glu Ala Pro Leu Pro
    290                 295                 300

Ser Gln His Pro Ser Gln Pro Phe Ser Gln Arg Pro Arg Pro Pro Leu
305                 310                 315                 320

Leu Ser Thr Ser Ala Pro Pro Tyr Met His Gly Gln Met Leu Arg Ser
                325                 330                 335

Leu Tyr Gln Gly Gln Gln Ile Ile Ile Gln Asn Leu Tyr Arg Leu Ser
            340                 345                 350

Leu His Leu Gln Met Asp Leu Pro Leu Met Thr Pro Glu Ala Tyr Arg
        355                 360                 365
```

| Gln | Gln | Val | Ala | Lys | Leu | Gly | Asp | Gln | Pro | Ser | Thr | Asp | Arg | Gly | Glu |
|---|---|---|---|---|---|---|---|---|---|---|---|---|---|---|---|
| 370 | | | | | 375 | | | | | 380 | | | | | |

| Glu | Pro | Ser | Gly | Ala | Ala | Thr | Glu | Asp | Pro | Ala | Val | Asp | Glu | Asp |
|---|---|---|---|---|---|---|---|---|---|---|---|---|---|---|
| 385 | | | | | 390 | | | | | 395 | | | | 400 |

| Leu | Ile | Ala | Asp | Leu | Ala | Gly | Ala | Asp | Trp | Ser | Pro | Trp | Ala | Asp | Leu |
|---|---|---|---|---|---|---|---|---|---|---|---|---|---|---|---|
| | | | | 405 | | | | 410 | | | | 415 | | | |

| Gly | Arg | Gly | Ser | Glx |
|---|---|---|---|---|
| | | | 420 | |

<210> SEQ ID NO 7
<211> LENGTH: 1596
<212> TYPE: DNA
<213> ORGANISM: Artificial Sequence
<220> FEATURE:
<223> OTHER INFORMATION: Description of Artificial Sequence: plant
      retroelement sequence

<400> SEQUENCE: 7

```
atgcgaggta gaactgcatc tggagacgtt gttcctatta acttagaaat tgaagctacg      60
tgtcggcgta caacgctgc aagaagaaga agggagcaag acatagaagg aagtagttac     120
acctcacctc ctccttctcc aaattatgct cagatggacg gggaaccggc acaaagagtc    180
acactagagg acttctctaa taccaccact cctcagttct ttacaagtat cacaaggccg    240
gaagtccaag cagatctcct tactcaaggg aacctcttcc atggtcttcc aaatgaagat    300
ccatatgcgc atctagcctc atacatagag atatgcagca ccgttaaaat cgccggagtt    360
ccaaaagatg cgatactcct taacctcttt tccttttccc tagcaggaga ggcaaaagga    420
tggttgcact cctttaaagg caatagctta agaacatggg aagaagtagt ggaaaaattc    480
ttaaagaagt atttcccaga gtcaaagacc gtcgaacgaa agatggagat ttcttatttc    540
catcaatttc tggatgaatc ccttagcgaa gcactagacc atttccacgg attgctaaga    600
aaaacaccaa cacacagata cagcgagcca gtacaactaa acatattcat cgatgacttg    660
caactcttaa tcgaaacagc tactagaggg aagatcaagc tgaagactcc cgaagaagcg    720
atggagctcg tcgagaacat ggcggctagc gatcaagcaa tccttcatga tcacacttat    780
gttcccacaa aaagaagcct cttggagctt agcacgcagg acgcaacttt ggtacaaaac    840
aagctgttga cgaggcagat agaagccctc atcgaaaccc tcagcaagct gcctcaacaa    900
ttacaagcga taagttcttc ccactcttct gttttgcagg tagaagaatg ccccacatgc    960
agagggacac atgagcctgg acaatgtgca agccaacaag cccctctcg tgaagtaaat   1020
tatataggca tactaaatcg ttacggattt cagggctaca accagggaaa tccatctgga   1080
ttcaatcaag gggcaacaag atttaatcac gagccaccgg ggtttaatca aggaagaaac   1140
ttcatgcaag gctcaagttg gacgaataaa ggaaatcaat ataaggagca aggaaccaa    1200
ccaccatacc agccaccata ccagcaccct agccaaggtc cgaatcagca gaaaagccc    1260
accaaaatag gaactgctgct gctgcaattc atcaaggaga caagatcaca tcaaaagagc   1320
acggatgcag ccattcggaa tctagaagtt caaatgggcc aactggcgca tgacaaagcc   1380
gaacggccca ctagaacttt cggtgctaac atggagagaa gaaccccaag gaaggataaa   1440
gcagtactga ctagagggca gagaagagcg caggaggagg taaggttga aggagaagac    1500
tggccagaag aaggaaggac agagaagaca gaagaagaag agaaggtggc agaagaacct   1560
aagcgtacca agagccagag agcaagggaa gccaag                              1596
```

<210> SEQ ID NO 8
<211> LENGTH: 532
<212> TYPE: PRT
<213> ORGANISM: Artificial Sequence
<220> FEATURE:
<223> OTHER INFORMATION: Description of Artificial Sequence: plant retroelement sequence

<400> SEQUENCE: 8

```
Met Arg Gly Arg Thr Ala Ser Gly Asp Val Val Pro Ile Asn Leu Glu
 1               5                  10                  15

Ile Glu Ala Thr Cys Arg Arg Asn Asn Ala Ala Arg Arg Arg Arg Glu
                20                  25                  30

Gln Asp Ile Glu Gly Ser Ser Tyr Thr Ser Pro Pro Ser Pro Asn
        35                  40                  45

Tyr Ala Gln Met Asp Gly Glu Pro Ala Gln Arg Val Thr Leu Glu Asp
    50                  55                  60

Phe Ser Asn Thr Thr Thr Pro Gln Phe Thr Ser Ile Thr Arg Pro
65                  70                  75                  80

Glu Val Gln Ala Asp Leu Leu Thr Gln Gly Asn Leu Phe His Gly Leu
                85                  90                  95

Pro Asn Glu Asp Pro Tyr Ala His Leu Ala Ser Tyr Ile Glu Ile Cys
            100                 105                 110

Ser Thr Val Lys Ile Ala Gly Val Pro Lys Asp Ala Ile Leu Leu Asn
        115                 120                 125

Leu Phe Ser Phe Ser Leu Ala Gly Glu Ala Lys Arg Trp Leu His Ser
    130                 135                 140

Phe Lys Gly Asn Ser Leu Arg Thr Trp Glu Glu Val Val Glu Lys Phe
145                 150                 155                 160

Leu Lys Lys Tyr Phe Pro Glu Ser Lys Thr Val Glu Arg Lys Met Glu
                165                 170                 175

Ile Ser Tyr Phe His Gln Phe Leu Asp Glu Ser Leu Ser Glu Ala Leu
            180                 185                 190

Asp His Phe His Gly Leu Leu Arg Lys Thr Pro Thr His Arg Tyr Ser
        195                 200                 205

Glu Pro Val Gln Leu Asn Ile Phe Ile Asp Asp Leu Gln Leu Leu Ile
    210                 215                 220

Glu Thr Ala Thr Arg Gly Lys Ile Lys Leu Lys Thr Pro Glu Glu Ala
225                 230                 235                 240

Met Glu Leu Val Glu Asn Met Ala Ala Ser Asp Gln Ala Ile Leu His
                245                 250                 255

Asp His Thr Tyr Val Pro Thr Lys Arg Ser Leu Leu Glu Leu Ser Thr
            260                 265                 270

Gln Asp Ala Thr Leu Val Gln Asn Lys Leu Leu Thr Arg Gln Ile Glu
        275                 280                 285

Ala Leu Ile Glu Thr Leu Ser Lys Leu Pro Gln Gln Leu Gln Ala Ile
    290                 295                 300

Ser Ser Ser His Ser Ser Val Leu Gln Val Glu Glu Cys Pro Thr Cys
305                 310                 315                 320

Arg Gly Thr His Glu Pro Gly Gln Cys Ala Ser Gln Gln Asp Pro Ser
                325                 330                 335

Arg Glu Val Asn Tyr Ile Gly Ile Leu Asn Arg Tyr Gly Phe Gln Gly
            340                 345                 350

Tyr Asn Gln Gly Asn Pro Ser Gly Phe Asn Gln Gly Ala Thr Arg Phe
        355                 360                 365
```

```
Asn His Glu Pro Pro Gly Phe Asn Gln Gly Arg Asn Phe Met Gln Gly
    370                 375                 380

Ser Ser Trp Thr Asn Lys Gly Asn Gln Tyr Lys Glu Gln Arg Asn Gln
385                 390                 395                 400

Pro Pro Tyr Gln Pro Tyr Gln His Pro Ser Gln Gly Pro Asn Gln
            405                 410                 415

Gln Glu Lys Pro Thr Lys Ile Glu Leu Leu Leu Gln Phe Ile Lys
            420                 425                 430

Glu Thr Arg Ser His Gln Lys Ser Thr Asp Ala Ala Ile Arg Asn Leu
                435                 440                 445

Glu Val Gln Met Gly Gln Leu Ala His Asp Lys Ala Glu Arg Pro Thr
    450                 455                 460

Arg Thr Phe Gly Ala Asn Met Glu Arg Arg Thr Pro Arg Lys Asp Lys
465                 470                 475                 480

Ala Val Leu Thr Arg Gly Gln Arg Arg Ala Gln Glu Glu Gly Lys Val
                485                 490                 495

Glu Gly Glu Asp Trp Pro Glu Gly Gly Arg Thr Glu Lys Thr Glu Glu
                500                 505                 510

Glu Glu Lys Val Ala Glu Glu Pro Lys Arg Thr Lys Ser Gln Arg Ala
            515                 520                 525

Arg Glu Ala Lys
    530

<210> SEQ ID NO 9
<211> LENGTH: 603
<212> TYPE: DNA
<213> ORGANISM: Artificial Sequence
<220> FEATURE:
<223> OTHER INFORMATION: Description of Artificial Sequence: plant
      retroelement sequence

<400> SEQUENCE: 9
tgtgataaat gccagagaac agggggata  tctcgaagaa atgagatgcc tttgcagaat    60
atcatggaag tagagatctt tgactgttgg ggcatagact tcatgggcc  ttttccttcg   120 tcatacggga atgtctacat cttggtagct gtggattacg tctccaaatg ggtggaagcc   180
atagccacgc caaggacga  tgccagggta gtgatcaaat ttctgaagaa gaacattttt   240
tcccgttttg gagtcccacg agccttgatt agtgataggg gaacgcactt ctgcaacaat   300
cagttgaaga aagtcctgga gcactataat gtccgacata aggtggccac acctttatcac  360 cctcagacaa atggccaagc agaaatttct aacagggagc tcaagcgaat cctggaaaag   420
acagttgcat caacaagaaa ggattggtcc ttgaagctcg atgatgctct ctgggcctat   480
aggacagcgt tcaagactcc catcggctta tcaccatttc agctagtgta tgggaaggca   540
tgtcatttac cagtggagct ggagtacaaa gcatattggg ctctcaagtt gctcaacttt   600
gac                                                                603

<210> SEQ ID NO 10
<211> LENGTH: 201
<212> TYPE: PRT
<213> ORGANISM: Artificial Sequence
<220> FEATURE:
<223> OTHER INFORMATION: Description of Artificial Sequence: plant
      retroelement sequence

<400> SEQUENCE: 10

Cys Asp Lys Cys Gln Arg Thr Gly Gly Ile Ser Arg Arg Asn Glu Met
 1               5                  10                  15
```

```
Pro Leu Gln Asn Ile Met Glu Val Glu Ile Phe Asp Cys Trp Gly Ile
             20                  25                  30

Asp Phe Met Gly Pro Phe Pro Ser Ser Tyr Gly Asn Val Tyr Ile Leu
         35                  40                  45

Val Ala Val Asp Tyr Val Ser Lys Trp Val Glu Ala Ile Ala Thr Pro
     50                  55                  60

Lys Asp Asp Ala Arg Val Val Ile Lys Phe Leu Lys Lys Asn Ile Phe
 65                  70                  75                  80

Ser Arg Phe Gly Val Pro Arg Ala Leu Ile Ser Asp Arg Gly Thr His
                 85                  90                  95

Phe Cys Asn Asn Gln Leu Lys Lys Val Leu Glu His Tyr Asn Val Arg
            100                 105                 110

His Lys Val Ala Thr Pro Tyr His Pro Gln Thr Asn Gly Gln Ala Glu
        115                 120                 125

Ile Ser Asn Arg Glu Leu Lys Arg Ile Leu Glu Lys Thr Val Ala Ser
    130                 135                 140

Thr Arg Lys Asp Trp Ser Leu Lys Leu Asp Asp Ala Leu Trp Ala Tyr
145                 150                 155                 160

Arg Thr Ala Phe Lys Thr Pro Ile Gly Leu Ser Pro Phe Gln Leu Val
                165                 170                 175

Tyr Gly Lys Ala Cys His Leu Pro Val Glu Leu Glu Tyr Lys Ala Tyr
            180                 185                 190

Trp Ala Leu Lys Leu Leu Asn Phe Asp
        195                 200

<210> SEQ ID NO 11
<211> LENGTH: 600
<212> TYPE: DNA
<213> ORGANISM: Artificial Sequence
<220> FEATURE:
<223> OTHER INFORMATION: Description of Artificial Sequence: plant
      retroelement sequence

<400> SEQUENCE: 11
ttggaggctg ggctcatata ccccatctct gacagcgctt gggtaagccc agtacaggtg      60
gttcccaaga aaggtggaat gacagtggta cgagatgaga ggaatgactt gataccaaca    120
cgaactgtca ctggttggcg aatgtgtatc gactatcgca agctgaatga agccacacgg    180
aaggaccatt tcccttacc tttcatggat cagatgctgg agagacttgc agggcaggca     240
tactactgtt tcttggatgg atactcggga tacaaccaga tcgcggtaga ccccagagat    300
caggagaaga cggcctttac atgccccttt ggcgtctttg cttacagaag gatgccattc    360
gggttatgta atgcaccagc cacatttcag aggtgcatgc tggccatttt ttcagacatg    420
gtggagaaaa gcatcgaggt atttatggac gacttctcgg tttttggacc ctcatttgac    480
agctgtttga ggaacctaga gagggtactt cagaggtgcg aagagactaa cttggtactg    540
aattgggaaa agtgtcattt catggttcga gagggcatag tcctaggcca caagatctca    600

<210> SEQ ID NO 12
<211> LENGTH: 200
<212> TYPE: PRT
<213> ORGANISM: Artificial Sequence
<220> FEATURE:
<223> OTHER INFORMATION: Description of Artificial Sequence: plant
      retroelement sequence
```

<400> SEQUENCE: 12

```
Leu Glu Ala Gly Leu Ile Tyr Pro Ile Ser Asp Ser Ala Trp Val Ser
 1               5                  10                  15

Pro Val Gln Val Val Pro Lys Lys Gly Gly Met Thr Val Val Arg Asp
             20                  25                  30

Glu Arg Asn Asp Leu Ile Pro Thr Arg Thr Val Thr Gly Trp Arg Met
         35                  40                  45

Cys Ile Asp Tyr Arg Lys Leu Asn Glu Ala Thr Arg Lys Asp His Phe
     50                  55                  60

Pro Leu Pro Phe Met Asp Gln Met Leu Glu Arg Leu Ala Gly Gln Ala
 65                  70                  75                  80

Tyr Tyr Cys Phe Leu Asp Gly Tyr Ser Gly Tyr Asn Gln Ile Ala Val
                 85                  90                  95

Asp Pro Arg Asp Gln Glu Lys Thr Ala Phe Thr Cys Pro Phe Gly Val
             100                 105                 110

Phe Ala Tyr Arg Arg Met Pro Phe Gly Leu Cys Asn Ala Pro Ala Thr
         115                 120                 125

Phe Gln Arg Cys Met Leu Ala Ile Phe Ser Asp Met Val Glu Lys Ser
     130                 135                 140

Ile Glu Val Phe Met Asp Asp Phe Ser Val Phe Gly Pro Ser Phe Asp
145                 150                 155                 160

Ser Cys Leu Arg Asn Leu Glu Arg Val Leu Gln Arg Cys Glu Glu Thr
                165                 170                 175

Asn Leu Val Leu Asn Trp Glu Lys Cys His Phe Met Val Arg Glu Gly
            180                 185                 190

Ile Val Leu Gly His Lys Ile Ser
        195                 200
```

<210> SEQ ID NO 13
<211> LENGTH: 858
<212> TYPE: DNA
<213> ORGANISM: Artificial Sequence
<220> FEATURE:
<223> OTHER INFORMATION: Description of Artificial Sequence: plant retroelement sequence

<400> SEQUENCE: 13

```
aaggaagaac cactagccct tccacaggat ctcccatatc ctatggcacc caccaagaag      60
aacaaggagc gttactttgc acgtttcttg gaaatattca aagggttaga atcactatg      120
ccattcgggg aagccttaca gcagatgccc ctctactcca aatttatgaa agacatcctc     180
accaagaagg ggaagtatat tgacaacgag aatattgtgg taggaggcaa ttgcagtgcg     240
ataatacaaa ggattctacc caagaagttt aaagaccccg gaagtgttac catcccgtgc     300
accattggga aggaagccgt aaacaaggcc ctcattgatc taggagcaag tatcaatctg     360
atgcccttgt caatgtgcaa agaattggga aatttgaaga tagatcccac caagatgacg     420
cttcaactgg cagaccgctc aatcacaagg ccatatgggg tggtagaaga tgtcctggtc     480
aaggtacgcc acttcacttt tccggtggac tttgttatca tggatatcga agaagacact     540
gagattcccc ttatcttagg cagacccttc atgctgactg ccaactgtgt ggtgatatg      600
gggaaaggga acttagagtt gactattgat aatcagaaga tcacctttga ccttatcaag     660
gcaatgaagt acccacagga gggttggaag tgcttcagaa tagaggagat tgatgaggaa     720
gatgtcagtt ttctcgagac accaaagact tcgctagaaa aagcaatggt aaatcattta     780
gactgtctaa ccagtgaaga ggaagaagat ctgaaggctt gcttggaaaa cttggatcaa     840
```
gaagacagta ttcctgag                                                858

<210> SEQ ID NO 14
<211> LENGTH: 286
<212> TYPE: PRT
<213> ORGANISM: Artificial Sequence
<220> FEATURE:
<223> OTHER INFORMATION: Description of Artificial Sequence: plant
      retroelement sequence

<400> SEQUENCE: 14

Lys Glu Glu Pro Leu Ala Leu Pro Gln Asp Leu Pro Tyr Pro Met Ala
 1               5                  10                  15

Pro Thr Lys Lys Asn Lys Glu Arg Tyr Phe Ala Arg Phe Leu Glu Ile
            20                  25                  30

Phe Lys Gly Leu Glu Ile Thr Met Pro Phe Gly Glu Ala Leu Gln Gln
        35                  40                  45

Met Pro Leu Tyr Ser Lys Phe Met Lys Asp Ile Leu Thr Lys Lys Gly
    50                  55                  60

Lys Tyr Ile Asp Asn Glu Asn Ile Val Val Gly Asn Cys Ser Ala
 65                  70                  75                  80

Ile Ile Gln Arg Ile Leu Pro Lys Lys Phe Lys Asp Pro Gly Ser Val
                85                  90                  95

Thr Ile Pro Cys Thr Ile Gly Lys Glu Ala Val Asn Lys Ala Leu Ile
            100                 105                 110

Asp Leu Gly Ala Ser Ile Asn Leu Met Pro Leu Ser Met Cys Lys Arg
        115                 120                 125

Ile Gly Asn Leu Lys Ile Asp Pro Thr Lys Met Thr Leu Gln Leu Ala
    130                 135                 140

Asp Arg Ser Ile Thr Arg Pro Tyr Gly Val Val Glu Asp Val Leu Val
145                 150                 155                 160

Lys Val Arg His Phe Thr Phe Pro Val Asp Phe Val Ile Met Asp Ile
                165                 170                 175

Glu Glu Asp Thr Glu Ile Pro Leu Ile Leu Gly Arg Pro Phe Met Leu
            180                 185                 190

Thr Ala Asn Cys Val Val Asp Met Gly Lys Gly Asn Leu Glu Leu Thr
        195                 200                 205

Ile Asp Asn Gln Lys Ile Thr Phe Asp Leu Ile Lys Ala Met Lys Tyr
    210                 215                 220

Pro Gln Glu Gly Trp Lys Cys Phe Arg Ile Glu Glu Ile Asp Glu Glu
225                 230                 235                 240

Asp Val Ser Phe Leu Glu Thr Pro Lys Thr Ser Leu Glu Lys Ala Met
                245                 250                 255

Val Asn His Leu Asp Cys Leu Thr Ser Glu Glu Glu Asp Leu Lys
            260                 265                 270

Ala Cys Leu Glu Asn Leu Asp Gln Glu Asp Ser Ile Pro Glu
        275                 280                 285

<210> SEQ ID NO 15
<211> LENGTH: 192
<212> TYPE: DNA
<213> ORGANISM: Artificial Sequence
<220> FEATURE:
<223> OTHER INFORMATION: Description of Artificial Sequence: plant
      retroelement sequence

```
<400> SEQUENCE: 15
tttgaactaa tgtgtgatgc cagtgattat gcagtaggag cagttttggg acagaggaaa      60
gacaaggtat ttcacgccat ctattatgct agcaaggtcc tgaatgaagc acagttgaat     120
tatgcaacca cagaaaagga gatgctagcc attgtctttg ccttggagaa gttcaggtca     180
tacttgatag gg                                                         192

<210> SEQ ID NO 16
<211> LENGTH: 64
<212> TYPE: PRT
<213> ORGANISM: Artificial Sequence
<220> FEATURE:
<223> OTHER INFORMATION: Description of Artificial Sequence: plant
      retroelement sequence

<400> SEQUENCE: 16

Phe Glu Leu Met Cys Asp Ala Ser Asp Tyr Ala Val Gly Ala Val Leu
  1               5                  10                  15

Gly Gln Arg Lys Asp Lys Val Phe His Ala Ile Tyr Tyr Ala Ser Lys
             20                  25                  30

Val Leu Asn Glu Ala Gln Leu Asn Tyr Ala Thr Thr Glu Lys Glu Met
         35                  40                  45

Leu Ala Ile Val Phe Ala Leu Glu Lys Phe Arg Ser Tyr Leu Ile Gly
     50                  55                  60

<210> SEQ ID NO 17
<211> LENGTH: 12286
<212> TYPE: DNA
<213> ORGANISM: Artificial Sequence
<220> FEATURE:
<223> OTHER INFORMATION: Description of Artificial Sequence: plant
      retroelement sequence

<400> SEQUENCE: 17
tgataactgc taaataattg tgaattaata gtagaaaatt agtcaaattt tggcttaaaa      60
ttaattattt agcagttatt tgtgattaaa agttagaaaa gcaattaagt tgaatttttg     120
gccatagata tgaaaactga aggtacaaca agcaaaaggc agcagaaagt gaagaaaaag     180
aataaaatct gaagcagacc cagcccaaca cgcgccctta gcgcgcgtca cgcgctaagc     240
ttgcaaggca gcacaggcac taagcgaggc gttaagcacg aagatgcagg attcgttacg     300
tgcgctaagc gcgaggcaca cgctaagcgc gcgatccaac agaagcacac gctaagcctg     360
cagcatgcgc taagcgcgcc tacgaaggcc caaagcccat ttctacacct ataaatagag     420
atccaagcca agggagaatg tacaccttgc ctcagagcac ttctctcagc attccaagct     480
tgagctctcc cttttctctc tatattcttt gcttttatta tccattcttt ctttcacccc     540
agttgtaaag cccctcaatg gccatgagtg gttaatcccc tagctacggc ctggtaggcc     600
taaaaagcca atgatgtatg gtgtacttca agagttatca atgcaaagag gattcattcc     660
aggttttatg ttctaattct ttcctttta tcttgcattt atgtcttaaa tttctgttgg     720
gttttattcg ctcgggagag ggtatttcct aataagggtt taagaagtaa tgcatgcatc     780
agttttaggg gttatacgct tggtaaaggg taacacctaa tagaacaaat taagaaaagg     840
atcgtcgggc tagcattgct aggcatagaa tgatggccca atgcccatgc atttagcaac     900
atctagaatt taaccttaat gcattttaat tattgaatct tcacaaaggc atttgggaga     960
taggtagtta aaataggctt gtcatcgtga ggcatcaagg gcaagtaaaa ttaatagatg    1020
tgggtagaac taattcaact gcattggtaa tgaacatcat aaattcattc atcgtaggcc    1080
```

```
aattaggttt gtccggtctt ggcattttca tcaattgtct tcctaaatta tttgatctaa     1140
tagcaacaat ttattcttat gcctattcct gtttttacta tttactttta cttacaaatt     1200
gaagagtatt caataaagtg caataaaatc cctatggaaa cgatactcgg acttccgaga     1260
attactactt agaacgattt ggtacacttg tcaaacacct caacaagttt ttggcgccgt     1320
tgtcggggat tttgttctcg cacttaattg ccatactata ttagtttgta agcttaattc     1380 ttctttttctt ggctcattct tttattattc tttactttac ttttttcttct atcctttctt     1440 tcttctccca taaattgcac gggtagtgcc tttttgtttt tatgcgaggt agaactgcat     1500
ctggagacgt tgttcctatt aacttagaaa ttgaagctac gtgtcggcgt aacaacgctg     1560
caagaagaag aagggagcaa gacatagaag gaagtagtta cacctcacct cctccttctc     1620
caaattatgc tcagatggac ggggaaccgg cacaaagagt cacactagag gacttctcta     1680
ataccaccac tcctcagttc tttacaagta tcacaaggcc ggaagtccaa gcagatctcc     1740
ttactcaagg gaacctcttc catggtcttc caaatgaaga tccatatgcg catctagcct     1800
catacataga gatatgcagc accgttaaaa tcgccggagt tccaaaagat gcgatactcc     1860
ttaacctctt ttccttttcc ctagcaggag aggcaaaaag atggttgcac tcctttaaag     1920
gcaatagctt aagaacatgg gaagaagtag tggaaaaatt cttaaagaag tatttcccag     1980
agtcaaagac cgtcgaacga aagatggaga tttcttattt ccatcaattt ctggatgaat     2040
cccttagcga agcactagac catttccacg gattgctaag aaaaacacca acacacagat     2100
acagcgagcc agtacaacta acatattcca tcgatgactt gcaactctta atcgaaacag     2160
ctactagagg gaagatcaag ctgaagactc ccgaagaagc gatggagctc gtcgagaaca     2220
tggcggctag cgatcaagca atccttcatg atcacactta tgttcccaca aaaagaagcc     2280
tcttggagct tagcacgcag gacgcaactt tggtacaaaa caagctgttg acgaggcaga     2340
tagaagccct catcgaaacc ctcagcaagc tgcctcaaca attacaagcg ataagttctt     2400
cccactcttc tgttttgcag gtagaagaat gccccacatg cagagggaca catgagcctg     2460
gacaatgtgc aagccaacaa gacccctctc gtgaagtaaa ttatataggc atactaaatc     2520
gttacggatt tcagggctac aaccagggaa atccatctgg attcaatcaa ggggcaacaa     2580
gatttaatca cgagccaccg gggtttaatc aaggaagaaa cttcatgcaa ggctcaagtt     2640
ggacgaataa aggaaatcaa tataaggagc aaaggaacca accaccatac cagccaccat     2700
accagcaccc tagccaaggt ccgaatcagc aagaaaagcc caccaaaata gaggaactgc     2760
tgctgcaatt catcaaggag acaagatcac atcaaaagag cacggatgca gccattcgga     2820
atctagaagt tcaaatgggc caactggcgc atgacaaagc cgaacggccc actagaactt     2880
tcggtgctaa catggagaga agaaccccaa ggaaggataa agcagtactg actagagggc     2940
agagaagagc gcaggaggag ggtaaggttg aaggagaaga ctggccagaa gaaggaagga     3000
cagagaagac agaagaagaa gagaaggtgg cagaagaacc taagcgtacc aagagccaga     3060
gagcaaggga agccaagaag gaagaaccac tagcccttcc acaggatctc ccatatccta     3120
tggcacccac caagaagaac aaggagcgtt actttgcacg tttcttggaa atattcaaag     3180
ggttagaaat cactatgcca ttcggggaag ccttacagca gatgccctc tactccaaat      3240 ttatgaaaga catcctcacc aagaagggga agtatattga caacgagaat attgtggtag     3300
gaggcaattg cagtgcgata atacaaagga ttctacccaa gaagtttaaa gacccggaa      3360 gtgttaccat cccgtgcacc attgggaagg aagccgtaaa caaggccctc attgatctag     3420
gagcaagtat caatctgatg cccttgtcaa tgtgcaaaag aattgggaat ttgaagatag     3480
```

-continued

```
atcccaccaa gatgacgctt caactggcag accgctcaat cacaaggcca tatgggtgg      3540
tagaagatgt cctggtcaag gtacgccact tcacttttcc ggtggacttt gttatcatgg     3600
atatcgaaga agacactgag attcccctta tcttaggcag acccttcatg ctgactgcca     3660
actgtgtggt ggatatgggg aaagggaact tagagttgac tattgataat cagaagatca     3720
cctttgacct tatcaaggca atgaagtacc cacaggaggt tggaagtgc ttcagaatag      3780
aggagattga tgaggaagat gtcagttttc tcgagacacc aaagacttcg ctagaaaaag     3840
caatggtaaa tcatttagac tgtctaacca gtgaagagga agaagatctg aaggcttgct     3900
tggaaaactt ggatcaagaa gacagtattc ctgagggaga agccaatttc gaggagctag     3960
agaaggaagt tccgtctgag aagccgaaga tagagttgaa gatattgcct gatcatctga     4020
agtatgtgtt cttggaggaa gataaaccta tagtgatcag taacgcactc acaacagagg     4080
aggaaaatag gttggtagat gtcctcaaga aacacaggga agcaattgga tggcacatat     4140
cggatctcaa ggaaattagc cctgcttact gcatgcacag gataatgatg gaagaggact     4200
acaagccagt ccgacaaccc cagaggcggc tgaatccaac aatgaaggaa gaggtaagaa     4260
aggaggtact caagctcttg gaggctgggc tcatataccc catctctgac agcgcttggg     4320
taagcccagt acaggtggtt cccaagaaag gtggaatgac agtggtacga gatgagagga     4380
atgacttgat accaacacga actgtcactg gttggcgaat gtgtatcgac tatcgcaagc     4440
tgaatgaagc cacacggaag gaccatttcc ccttaccttt catggatcag atgctggaga     4500
gacttgcagg gcaggcatac tactgtttct tggatggata ctcgggatac aaccagatcg     4560
cggtagaccc cagagatcag gagaagacgg cctttacatg ccccttggc gtctttgctt      4620
acagaaggat gccattcggg ttatgtaatg caccagccac atttcagagg tgcatgctgg     4680
ccatttttc agacatggtg gagaaaagca tcgaggtatt tatggacgac ttctcggttt      4740
ttggaccctc atttgacagc tgtttgagga acctagagag ggtacttcag aggtgcgaag     4800
agactaactt ggtactgaat tgggaaaagt gtcatttcat ggttcgagag ggcatagtcc     4860
taggccacaa gatctcagcc agagggattg aggttgatcg ggcaaagata gacgtcatcg     4920
agaagctgcc accaccactg aatgttaaag gggttagaag tttcttaggg catgcaggtt     4980
tctacaggag gttatcaag gacttctcga agattgccag gcccttaagc aatctgttga      5040
ataaagacgt ggcttttgtg tttgatgaag aatgtttagc agcatttcaa tcactgaaga     5100
ataagctcgt cactgcaccc gtaatgattg cacccgactg gaataaagat tttgaactaa     5160
tgtgtgatgc cagtgattat gcagtaggag cagttttggg acagaggaaa gacaaggtat     5220
ttcacgccat ctattatgct agcaaggtcc tgaatgaagc acagttgaat tatgcaacca     5280
cagaaaagga gatgctagcc attgtctttg ccttggagaa gttcaggtca tacttgatag     5340
ggtcgagggt catcatttac acagatcatg ctgccatcaa gcacctgctc gccaaaacag     5400
actcaaagcc gaggttgatt agatgggtcc tgctgttaca agaatttgac atcatcatca     5460
aggacaagaa aggatccgag aatgtggtag ccaatcatct atctcgatta agaatgaag      5520
aagtcaccaa ggaagaacca gaggtaaaag gtgaatttcc tgatgagttt cttttgcagg     5580
ttaccgaaag accttggttt gcagacatgg ctaactacaa agccacggga gtcattccag     5640
aggagtttaa ttggagtcag aggaagaaat tcttgcacga tgcacgcttc tatgtgtggg     5700
atgatcctca tttgttcaag gcaggagcag ataatttatt aaggagatgc gtcacaaagg     5760
aggaagcacg gagcattctt tggcactgcc acagttcacc ctatgcgga caccacagtg      5820
gggacagaac agcagcaaaa gtgctacaat caggttttttt ctggccctct atttttaaag   5880
```

```
atgctcacga gtttgtgcgt tgttgtgata aatgccagag aacagggggg atatctcgaa    5940
gaaatgagat gcctttgcag aatatcatgg aagtagagat ctttgactgt tggggcatag    6000
acttcatggg gccttttcct tcgtcatacg ggaatgtcta catcttggta gctgtggatt    6060
acgtctccaa atgggtggaa gccatagcca cgccaaagga cgatgccagg gtagtgatca    6120
aatttctgaa gaagaacatt ttttcccgtt ttggagtccc acgagccttg attagtgata    6180
ggggaacgca cttctgcaac aatcagttga agaaagtcct ggagcactat aatgtccgac    6240
ataaggtggc cacaccttat caccctcaga caaatggcca agcagaaatt tctaacaggg    6300
agctcaagcg aatcctggaa aagacagttg catcaacaag aaaggattgg tccttgaagc    6360
tcgatgatgc tctctgggcc tataggacag cgttcaagac tcccatcggc ttatcaccat    6420
ttcagctagt gtatgggaag gcatgtcatt taccagtgga gctggagtac aaagcatatt    6480
gggctctcaa gttgctcaac tttgacaaca acgcatgcgg ggaaaagagg aagctacagc    6540
tgctggaatt agaagagatg agactgaatg cctacgagtc atccaaaatt tacaaggaaa    6600
agatgaaggc atatcatgac aagaagctac tgaggaaaga attccagcca gggcagcagg    6660
tattactctt taactcaagg ctaaggctat tcccaggtaa gctgaagtcc aagtggtcag    6720
ggccattcat aatcaaagaa gtcagacctt acggagcagt agaattggtg gaccctagag    6780
aagaggactt tgagaagaaa tggatcgtca atggacagcg cttgaagcct tataacggag    6840
gacaactaga gcgattgacg accatcatct acttaaatga cccttgagaa ggcctactgt    6900
ctagctaaag acaataaact aagcgctggt tgggaggcaa cccaacatat tttgtaaaaa    6960
tgtagttatc tttattctat gtaaaaaaaa aaaaaagcc caataggtgc aaataggaaa    7020
caggaggtgc aaaaagcaaa ggcccaacag gtgaagacaa cataggagg ggtgccaata    7080 gcaaaactga agtgggctgc acgaagccac gcgcccaatt cttggtcttt tcacacaaaa    7140
caatcactaa cgaaggtaaa gaattgcttt gtatggatgt tgttatgaat gcacaggtaa    7200
cagcacgcta agccctgctc gacgcttagc caatgaagac ggattgaagg ccataacgac    7260
gagctcgtta agcgtgacga agcacgctaa gcaggcgcct gacaggacga gaaagcaaag    7320
cgcgcgctta gccggcactt ccgcgctaag cgcgctcatg aacatcactg aacgcgctaa    7380
acgtgtgcca gaggcgctaa acgcgtgcca gaggcgctaa acgcgtgcat tagtcacagc    7440
aggatggtgc taagcgcggg gttgggcctc agggcccatc aaccctcgca ccttacttgt    7500
tgcaccccta tttctactat tcccactccc ttctaatttc tttttgcacc cccttcttt    7560 actgactgca cctctatttt gattactttt tgcaccccc ctgattgcta acttcagact    7620
atctttcttg tttttttgttt ttttggtttt ttggtcagat ggcctcccgt aaacgcaaag    7680
ctgtgcccac acccggggaa gcgtccaact gggactcttc acgtttcact ttcgagattg    7740
cttggcacag ataccaggat agcattcagc tccggaacat ccttccagag aggaatgtag    7800
agcttggacc agggatgttt gatgagttcc tgcaggaact ccagaggctc agatgggacc    7860
aggttctgac ccgacttcca gagaagtgga ttgatgttgc tctggtgaag gagttttact    7920
ccaacctata tgatccagag gaccacagtc cgaagttttg gagtgttcga ggacaggttg    7980
tgagatttga tgctgagacg attaatgatt tcctcgacac cccggtcatc ttggcagagg    8040
gagaggatta tccagcctac tctcagtacc tcagcactcc tccagaccat gatgccatcc    8100
tttccgctct gtgtactcca gggggacgat ttgttctgaa tgttgatagt gcccctggaa    8160
agctgctgcg gaaggatctg atgacgctcg cgcagacatg gagtgtgctc tcttatttta    8220
accttgcact gacttttcac acttctgata ttaatgttga cagggcccga ctcaattatg    8280
```

```
gcttggtgat gaagatggac ctggacgtgg gcagcctcat ttctcttcag atcagtcaga    8340
tcgcccagtc catcacttcc aggcttgggt tcccagcgtt gatcacaaca ctgtgtgaga    8400
ttcaggrggggt tgtctctgat accctgattt ttgagtcact cagtcctgtg atcaaccttg  8460
cctacattaa gaagaactgc tggaaccctg ccgatccatc tatcacattt caggggaccc    8520
gccgcacgcg caccagagct tcggcgtcgg catctgaggc tcctcttcca tcccagcatc    8580
cttctcagcc ttttcccag agaccacggc ctccacttct atccacctca gcacctccat     8640
acatgcatgg acagatgctc aggtccttgt accagggtca gcagatcatc attcagaacc    8700
tgtatcgatt gtccctacat ttgcagatgg atctgccact catgactccg gaggcctatc    8760
gtcagcaggt cgccaagcta ggagaccagc cctccactga caggggggaa gagccttctg    8820
gagccgctgc tactgaggat cctgccgttg atgaagacct catagctgac ttggctggcg    8880
ctgattggag cccatgggca gacttgggca gaggcagctg atcttatgct taatgttttt    8940
cttttatatt atgtttgtgt tctctttat gttttatgtt atgtttttat gtagtctgtt     9000
tggtaattaa aaagaggtag tagtaaaaat attagtattt cagtatgtgt tttctgagta    9060
ataagtgcat gataactcaa gcaatcataa ttctttagct tgttcagaaa ggttcaacac    9120
ttgagatgcc actgatcctt ggagaaacac tggttctgga agcaaaagtc aggtcaagaa    9180
atggaacatg aatagcacag agtggaaagg ttagcttgat ggaacaaggt cataactggt    9240
acgccgaata cttgtttaag tccctgtgag catggttgtc aaactctaga gtcaactcat    9300
agactctcat gagtttaaga gtttacttca gtcccgcgag ttgactcgga agcaaactcg    9360
cttttgagca aactcgtgga ctcggagtga actcatgtaa actcgtaaga gtctacgagt    9420
tgactctaga gtttgacaac catgcataag tgttcaaaat taaagcattt aataattaa     9480
aaaaagcaca aatgtcttca aagaagcatg ttcaatcctc taataggatc atcttcatga    9540
atatcatcac tttcatcatc atctccatct ccatcatcat catcaaggtc ttcctcagat    9600
tgtgcatcat cattaggttc cacaaagatt aaattatcta gatcaaaagc ttaaaataga    9660
tatcaaatat gctatattag aaatagttaa aacttaaaat aatacacaag caaattttaa    9720
atatgagaaa gttcagaaat tataccttt cttggtgtta ttaaagtttc attttatctt     9780
ctcttttgca ttttccatct cctcacatat gaaaagcata attctattga atttcagtaa    9840
caagtttgat ccaactccaa cattgtaagg tcagttgttg tgttttgtaa tagactaata   9900
tgaagtatga agtatgaact atgaacttat tgtcatctgt ttgcaaattg gtgcatttg     9960
aatatattta cttattatcc attttttttt ttttacgaag tagactctca cgagtctgcg   10020
tagactctcg atatcgataa ccttgccgat gagagtgtga acttaattgt gagagaaaat   10080
gcctattttt aagttcctgg ttttgcatca ttcttagacg gttagaatag ttacttaagg   10140
tggatatgat caaggccatg tttgtttgtt tacctactta gccaaaaagc caacctaaca   10200
tagtttacc ccttgcaccc atgattgagc caactgatta ttttgaatta accttgagcc     10260
aattaaacaa aatcctgacc ttttaggatt ttaagagagt aaaaatgggt tataaaggtc   10320
ttaatttggg ggattttggg aaataggtag ccaagacaat aagtacagca cacaaagtag   10380
gacaccttt acaaacagta ggcccaattt cgaaaaaaaa atgaaaagaa tttaataaag     10440
ggcagaaaca aaagagcaag agaggtgtca aagaaaaagt gttgtgggga aataaagggg   10500
ctaagtaaaa aggcctaggc agaattggaa attttttgttc tcttttaatc ctaactttga  10560
atttccaaga aaaccatga tttttttgtaa gccaggcccc gatacaagcc aataaagtcc    10620
ttagtgatcc accaaaggta actagagata actgtaactg agatgaaatg caaaattttg   10680
```

-continued

```
aagtgttact tgcaggttgt tatcaaattg caaacactaa actaggcact tgtgagcaga    10740
gggaaacacc agccttgtga ggaaagtaag gcaagccaaa tttgattgag ttccagatga    10800
ctaactgatt caattcttct gttgtaatgc tttcatttta agatgttgac agatgcagaa    10860
aggaccagtg aaagaaggag gaactgagcc attgatagtg ttggaatatt aagaacttg     10920 cttgagaatt tacttgtttt tggttttctt ggggacaagc aaagtttcat ttggggaatt    10980
ttgataactg ctaaataatt gtgaattaat agtagaaaat tagtcaaatt ttggcttaaa    11040
attaattatt tagcagttat ttgtgattaa aagttagaaa agcaattaag ttgaattttt    11100
ggccatagat atgaaaactg aaggtacaac aagcaaaagg cagcagaaag tgaagaaaaa    11160
gaataaaatc tgaagcagac ccagcccaac acgcgccctt agcgcgcgtc acgcgctaag    11220
cttgcaaggc agcacaggca ctaagcgagg cgttaagcac gaagatgcag gattcgttac    11280
gtgcgctaag cgcgaggcac acgctaagcg cgcgatccaa cagaagcaca cgctaagcct    11340
gcagcatgcg ctaagcgcgc ctacgaaggc ccaaagccca tttctacacc tataaataga    11400
gatccaagcc aagggagaat gtacaccttg cctcagagca cttctctcag cattccaagc    11460
ttgagctctc cctttctctc tatattctt tgcttttatt atccattctt tctttcaccc     11520
cagttgtaaa gcccctcaat ggccatgagt ggttaatccc ctagctacgg cctggtaggc    11580
ctaaaaagcc aatgatgtat ggtgtacttc aagagttatc aatgcaaaga ggattcattc    11640
caggttttat gttctaattc tttccttttt atcttgcatt tatgtcttaa atttctgttg    11700
ggttttattc gctcgggaga gggtatttcc taataagggt ttaagaagta atgcatgcat    11760 cagtttagg ggttatacgc ttggtaaagg gtaacaccta atagaacaaa ttaagaaaag    11820
gatcgtcggg ctagcattgc taggcataga atgatgccc aatgcccatg catttagcaa     11880
catctagaat ttaaccttaa tgcatttaa ttattgaatc ttcacaaagg catttgggag     11940
ataggtagtt aaaataggct tgtcatcgtg aggcatcaag ggcaagtaaa attaatagat    12000
gtgggtagaa ctaattcaac tgcattggta atgaacatca taaattcatt catcgtaggc    12060
caattaggtt tgtccggtct tggcattttc atcaattgtc ttcctaaatt atttgatcta    12120
atagcaacaa tttattctta tgcctattcc tgttttttact atttactttt acttacaaat   12180
tgaagagtat tcaataaagt gcaataaaat ccctatggaa acgatactcg gacttccgag    12240
aattactact tagaacgatt tggtacactt gtcaaacacc tcaaca                   12286
```

<210> SEQ ID NO 18
<211> LENGTH: 1802
<212> TYPE: PRT
<213> ORGANISM: Artificial Sequence
<220> FEATURE:
<223> OTHER INFORMATION: Description of Artificial Sequence: plant retroelement sequence

<400> SEQUENCE: 18

```
Met Arg Gly Arg Thr Ala Ser Gly Asp Val Val Pro Ile Asn Leu Glu
  1               5                  10                  15

Ile Glu Ala Thr Cys Arg Arg Asn Asn Ala Ala Arg Arg Arg Arg Glu
             20                  25                  30

Gln Asp Ile Glu Gly Ser Ser Tyr Thr Ser Pro Pro Ser Pro Asn
         35                  40                  45

Tyr Ala Gln Met Asp Gly Glu Pro Ala Gln Arg Val Thr Leu Glu Asp
     50                  55                  60

Phe Ser Asn Thr Thr Thr Pro Gln Phe Phe Thr Ser Ile Thr Arg Pro
 65                  70                  75                  80
```

-continued

```
Glu Val Gln Ala Asp Leu Leu Thr Gln Gly Asn Leu Phe His Gly Leu
                 85                  90                  95
Pro Asn Glu Asp Pro Tyr Ala His Leu Ala Ser Tyr Ile Glu Ile Cys
            100                 105                 110
Ser Thr Val Lys Ile Ala Gly Val Pro Lys Asp Ala Ile Leu Leu Asn
        115                 120                 125
Leu Phe Ser Phe Ser Leu Ala Gly Glu Ala Lys Arg Trp Leu His Ser
130                 135                 140
Phe Lys Gly Asn Ser Leu Arg Thr Trp Glu Glu Val Glu Lys Phe
145                 150                 155                 160
Leu Lys Lys Tyr Phe Pro Glu Ser Lys Thr Val Glu Arg Lys Met Glu
                165                 170                 175
Ile Ser Tyr Phe His Gln Phe Leu Asp Glu Ser Leu Ser Glu Ala Leu
            180                 185                 190
Asp His Phe His Gly Leu Leu Arg Lys Thr Pro Thr His Arg Tyr Ser
        195                 200                 205
Glu Pro Val Gln Leu Asn Ile Phe Ile Asp Asp Leu Gln Leu Leu Ile
210                 215                 220
Glu Thr Ala Thr Arg Gly Lys Ile Lys Leu Lys Thr Pro Glu Glu Ala
225                 230                 235                 240
Met Glu Leu Val Glu Asn Met Ala Ala Ser Asp Gln Ala Ile Leu His
                245                 250                 255
Asp His Thr Tyr Val Pro Thr Lys Arg Ser Leu Leu Glu Leu Ser Thr
            260                 265                 270
Gln Asp Ala Thr Leu Val Gln Asn Lys Leu Leu Thr Arg Gln Ile Glu
        275                 280                 285
Ala Leu Ile Glu Thr Leu Ser Lys Leu Pro Gln Gln Leu Gln Ala Ile
290                 295                 300
Ser Ser Ser His Ser Ser Val Leu Gln Val Glu Glu Cys Pro Thr Cys
305                 310                 315                 320
Arg Gly Thr His Glu Pro Gly Gln Cys Ala Ser Gln Gln Asp Pro Ser
                325                 330                 335
Arg Glu Val Asn Tyr Ile Gly Ile Leu Asn Arg Tyr Gly Phe Gln Gly
            340                 345                 350
Tyr Asn Gln Gly Asn Pro Ser Gly Phe Asn Gln Gly Ala Thr Arg Phe
        355                 360                 365
Asn His Glu Pro Pro Gly Phe Asn Gln Gly Arg Asn Phe Met Gln Gly
370                 375                 380
Ser Ser Trp Thr Asn Lys Gly Asn Gln Tyr Lys Glu Gln Arg Asn Gln
385                 390                 395                 400
Pro Pro Tyr Gln Pro Pro Tyr Gln His Pro Ser Gln Gly Pro Asn Gln
                405                 410                 415
Gln Glu Lys Pro Thr Lys Ile Glu Glu Leu Leu Leu Gln Phe Ile Lys
            420                 425                 430
Glu Thr Arg Ser His Gln Lys Ser Thr Asp Ala Ala Ile Arg Asn Leu
        435                 440                 445
Glu Val Gln Met Gly Gln Leu Ala His Asp Lys Ala Glu Arg Pro Thr
450                 455                 460
Arg Thr Phe Gly Ala Asn Met Glu Arg Arg Thr Pro Arg Lys Asp Lys
465                 470                 475                 480
Ala Val Leu Thr Arg Gly Gln Arg Arg Ala Gln Glu Glu Gly Lys Val
                485                 490                 495
```

-continued

```
Glu Gly Glu Asp Trp Pro Glu Gly Arg Thr Glu Lys Thr Glu Glu
            500                 505                 510

Glu Glu Lys Val Ala Glu Pro Lys Arg Thr Lys Ser Gln Arg Ala
        515                 520                 525

Arg Glu Ala Lys Lys Glu Pro Leu Ala Leu Pro Gln Asp Leu Pro
        530                 535                 540

Tyr Pro Met Ala Pro Thr Lys Lys Asn Lys Glu Arg Tyr Phe Ala Arg
545                 550                 555                 560

Phe Leu Glu Ile Phe Lys Gly Leu Glu Ile Thr Met Pro Phe Gly Glu
                565                 570                 575

Ala Leu Gln Gln Met Pro Leu Tyr Ser Lys Phe Met Lys Asp Ile Leu
                580                 585                 590

Thr Lys Lys Gly Lys Tyr Ile Asp Asn Glu Asn Ile Val Val Gly Gly
            595                 600                 605

Asn Cys Ser Ala Ile Ile Gln Arg Ile Leu Pro Lys Lys Phe Lys Asp
    610                 615                 620

Pro Gly Ser Val Thr Ile Pro Cys Thr Ile Gly Lys Glu Ala Val Asn
625                 630                 635                 640

Lys Ala Leu Ile Asp Leu Gly Ala Ser Ile Asn Leu Met Pro Leu Ser
                645                 650                 655

Met Cys Lys Arg Ile Gly Asn Leu Lys Ile Asp Pro Thr Lys Met Thr
            660                 665                 670

Leu Gln Leu Ala Asp Arg Ser Ile Thr Arg Pro Tyr Gly Val Val Glu
        675                 680                 685

Asp Val Leu Val Lys Val Arg His Phe Thr Phe Pro Val Asp Phe Val
        690                 695                 700

Ile Met Asp Ile Glu Glu Asp Thr Glu Ile Pro Leu Ile Leu Gly Arg
705                 710                 715                 720

Pro Phe Met Leu Thr Ala Asn Cys Val Val Asp Met Gly Lys Gly Asn
                725                 730                 735

Leu Glu Leu Thr Ile Asp Asn Gln Lys Ile Thr Phe Asp Leu Ile Lys
            740                 745                 750

Ala Met Lys Tyr Pro Gln Glu Gly Trp Lys Cys Phe Arg Ile Glu Glu
        755                 760                 765

Ile Asp Glu Glu Asp Val Ser Phe Leu Glu Thr Pro Lys Thr Ser Leu
770                 775                 780

Glu Lys Ala Met Val Asn His Leu Asp Cys Leu Thr Ser Glu Glu Glu
785                 790                 795                 800

Glu Asp Leu Lys Ala Cys Leu Glu Asn Leu Asp Gln Glu Asp Ser Ile
                805                 810                 815

Pro Glu Gly Glu Ala Asn Phe Glu Glu Leu Glu Lys Glu Val Pro Ser
                820                 825                 830

Glu Lys Pro Lys Ile Glu Leu Lys Ile Leu Pro Asp His Leu Lys Tyr
        835                 840                 845

Val Phe Leu Glu Glu Asp Lys Pro Ile Val Ile Ser Asn Ala Leu Thr
        850                 855                 860

Thr Glu Glu Glu Asn Arg Leu Val Asp Val Leu Lys Lys His Arg Glu
865                 870                 875                 880

Ala Ile Gly Trp His Ile Ser Asp Leu Lys Glu Ile Ser Pro Ala Tyr
                885                 890                 895

Cys Met His Arg Ile Met Met Glu Glu Asp Tyr Lys Pro Val Arg Gln
                900                 905                 910
```

-continued

```
Pro Gln Arg Arg Leu Asn Pro Thr Met Lys Glu Glu Val Arg Lys Glu
            915                 920                 925

Val Leu Lys Leu Leu Glu Ala Gly Leu Ile Tyr Pro Ile Ser Asp Ser
        930                 935                 940

Ala Trp Val Ser Pro Val Gln Val Val Pro Lys Lys Gly Gly Met Thr
945                 950                 955                 960

Val Val Arg Asp Glu Arg Asn Asp Leu Ile Pro Thr Arg Thr Val Thr
                965                 970                 975

Gly Trp Arg Met Cys Ile Asp Tyr Arg Lys Leu Asn Glu Ala Thr Arg
            980                 985                 990

Lys Asp His Phe Pro Leu Pro Phe Met Asp Gln Met Leu Glu Arg Leu
        995                 1000                1005

Ala Gly Gln Ala Tyr Tyr Cys Phe Leu Asp Gly Tyr Ser Gly Tyr Asn
    1010                1015                1020

Gln Ile Ala Val Asp Pro Arg Asp Gln Glu Lys Thr Ala Phe Thr Cys
1025                1030                1035                1040

Pro Phe Gly Val Phe Ala Tyr Arg Arg Met Pro Phe Gly Leu Cys Asn
                1045                1050                1055

Ala Pro Ala Thr Phe Gln Arg Cys Met Leu Ala Ile Phe Ser Asp Met
            1060                1065                1070

Val Glu Lys Ser Ile Glu Val Phe Met Asp Asp Phe Ser Val Phe Gly
        1075                1080                1085

Pro Ser Phe Asp Ser Cys Leu Arg Asn Leu Glu Arg Val Leu Gln Arg
    1090                1095                1100

Cys Glu Glu Thr Asn Leu Val Leu Asn Trp Glu Lys Cys His Phe Met
1105                1110                1115                1120

Val Arg Glu Gly Ile Val Leu Gly His Lys Ile Ser Ala Arg Gly Ile
                1125                1130                1135

Glu Val Asp Arg Ala Lys Ile Asp Val Ile Glu Lys Leu Pro Pro Pro
            1140                1145                1150

Leu Asn Val Lys Gly Val Arg Ser Phe Leu Gly His Ala Gly Phe Tyr
        1155                1160                1165

Arg Arg Phe Ile Lys Asp Phe Ser Lys Ile Ala Arg Pro Leu Ser Asn
    1170                1175                1180

Leu Leu Asn Lys Asp Val Ala Phe Val Phe Asp Glu Glu Cys Leu Ala
1185                1190                1195                1200

Ala Phe Gln Ser Leu Lys Asn Lys Leu Val Thr Ala Pro Val Met Ile
                1205                1210                1215

Ala Pro Asp Trp Asn Lys Asp Phe Glu Leu Met Cys Asp Ala Ser Asp
            1220                1225                1230

Tyr Ala Val Gly Ala Val Leu Gly Gln Arg Lys Asp Lys Val Phe His
        1235                1240                1245

Ala Ile Tyr Tyr Ala Ser Lys Val Leu Asn Glu Ala Gln Leu Asn Tyr
    1250                1255                1260

Ala Thr Thr Glu Lys Glu Met Leu Ala Ile Val Phe Ala Leu Glu Lys
1265                1270                1275                1280

Phe Arg Ser Tyr Leu Ile Gly Ser Arg Val Ile Ile Tyr Thr Asp His
                1285                1290                1295

Ala Ala Ile Lys His Leu Leu Ala Lys Thr Asp Ser Lys Pro Arg Leu
            1300                1305                1310

Ile Arg Trp Val Leu Leu Leu Gln Glu Phe Asp Ile Ile Ile Lys Asp
        1315                1320                1325
```

-continued

```
Lys Lys Gly Ser Glu Asn Val Val Ala Asn His Leu Ser Arg Leu Lys
    1330                1335                1340

Asn Glu Glu Val Thr Lys Glu Pro Glu Val Lys Gly Glu Phe Pro
1345                1350                1355                1360

Asp Glu Phe Leu Leu Gln Val Thr Glu Arg Pro Trp Phe Ala Asp Met
                1365                1370                1375

Ala Asn Tyr Lys Ala Thr Gly Val Ile Pro Glu Glu Phe Asn Trp Ser
            1380                1385                1390

Gln Arg Lys Lys Phe Leu His Asp Ala Arg Phe Tyr Val Trp Asp Asp
                1395                1400                1405

Pro His Leu Phe Lys Ala Gly Ala Asp Asn Leu Leu Arg Arg Cys Val
            1410                1415                1420

Thr Lys Glu Glu Ala Arg Ser Ile Leu Trp His Cys His Ser Ser Pro
1425                1430                1435                1440

Tyr Gly Gly His His Ser Gly Asp Arg Thr Ala Ala Lys Val Leu Gln
                1445                1450                1455

Ser Gly Phe Phe Trp Pro Ser Ile Phe Lys Asp Ala His Glu Phe Val
            1460                1465                1470

Arg Cys Cys Asp Lys Cys Gln Arg Thr Gly Gly Ile Ser Arg Arg Asn
            1475                1480                1485

Glu Met Pro Leu Gln Asn Ile Met Glu Val Glu Ile Phe Asp Cys Trp
            1490                1495                1500

Gly Ile Asp Phe Met Gly Pro Phe Pro Ser Ser Tyr Gly Asn Val Tyr
1505                1510                1515                1520

Ile Leu Val Ala Val Asp Tyr Val Ser Lys Trp Val Glu Ala Ile Ala
                1525                1530                1535

Thr Pro Lys Asp Asp Ala Arg Val Val Ile Lys Phe Leu Lys Lys Asn
            1540                1545                1550

Ile Phe Ser Arg Phe Gly Val Pro Arg Ala Leu Ile Ser Asp Arg Gly
            1555                1560                1565

Thr His Phe Cys Asn Asn Gln Leu Lys Lys Val Leu Glu His Tyr Asn
    1570                1575                1580

Val Arg His Lys Val Ala Thr Pro Tyr His Pro Gln Thr Asn Gly Gln
1585                1590                1595                1600

Ala Glu Ile Ser Asn Arg Glu Leu Lys Arg Ile Leu Glu Lys Thr Val
                1605                1610                1615

Ala Ser Thr Arg Lys Asp Trp Ser Leu Lys Leu Asp Asp Ala Leu Trp
            1620                1625                1630

Ala Tyr Arg Thr Ala Phe Lys Thr Pro Ile Gly Leu Ser Pro Phe Gln
            1635                1640                1645

Leu Val Tyr Gly Lys Ala Cys His Leu Pro Val Glu Leu Glu Tyr Lys
    1650                1655                1660

Ala Tyr Trp Ala Leu Lys Leu Leu Asn Phe Asp Asn Asn Ala Cys Gly
1665                1670                1675                1680

Glu Lys Arg Lys Leu Gln Leu Leu Glu Leu Glu Glu Met Arg Leu Asn
                1685                1690                1695

Ala Tyr Glu Ser Ser Lys Ile Tyr Lys Glu Lys Met Lys Ala Tyr His
            1700                1705                1710

Asp Lys Lys Leu Leu Arg Lys Glu Phe Gln Pro Gly Gln Gln Val Leu
            1715                1720                1725

Leu Phe Asn Ser Arg Leu Arg Leu Phe Pro Gly Lys Leu Lys Ser Lys
    1730                1735                1740
```

Trp Ser Gly Pro Phe Ile Ile Lys Glu Val Arg Pro Tyr Gly Ala Val
1745                1750                1755                1760

Glu Leu Val Asp Pro Arg Glu Asp Phe Glu Lys Lys Trp Ile Val
        1765                1770                1775

Asn Gly Gln Arg Leu Lys Pro Tyr Asn Gly Gly Gln Leu Glu Arg Leu
            1780                1785                1790

Thr Thr Ile Ile Tyr Leu Asn Asp Pro Glx
        1795                1800

<210> SEQ ID NO 19
<211> LENGTH: 9829
<212> TYPE: DNA
<213> ORGANISM: Glycine max

<400> SEQUENCE: 19

| | | | | | |
|---|---|---|---|---|---|
| tgataactgc | taaataattg | tgaattaata | gtagaaaatt | agtcaaattt | tggcttaaaa | 60 |
| ttaattattt | agcagttatt | tgtgattaaa | agttagaaaa | gcaattaagt | tgaatttttg | 120 |
| gccatagata | tgaaaactga | aggtacaaca | agcaaaaggc | agcagaaagt | gaagaaaaag | 180 |
| aataaaatct | gaagcagacc | cagcccaaca | cgcgcccttaa | gcgcgcgtca | cgcgctaagc | 240 |
| ttgcaaggca | gcacaggcac | taagcgaggc | gttaagcacg | aagatgcagg | attcgttacg | 300 |
| tgcgctaagc | gcgaggcaca | cgctaagcgc | gcgatccaac | agaagcacac | gctaagcctg | 360 |
| cagcatgcgc | taagcgcgcc | tacgaaggcc | caaagcccat | ttctacacct | ataaatagag | 420 |
| atccaagcca | agggagaatg | tacaccttgc | ctcagagcac | ttctctcagc | attccaagct | 480 |
| tgagctctcc | cttttctctc | tatattcttt | gcttttatta | tccattcttt | ctttcacccc | 540 |
| agttgtaaag | cccctcaatg | gccatgagtg | gttaatcccc | tagctacggc | ctggtaggcc | 600 |
| taaaaagcca | atgatgtatg | gtgtacttca | agagttatca | atgcaaagag | gattcattcc | 660 |
| aggttttatg | ttctaattct | ttccttttta | tcttgcattt | atgtcttaaa | tttctgttgg | 720 |
| gttttattcg | ctcgggagag | ggtatttcct | aataagggtt | taagaagtaa | tgcatgcatc | 780 |
| agttttaggg | gttatacgct | tggtaaaggg | taacacctaa | tagaacaaat | taagaaaagg | 840 |
| atcgtcgggc | tagcattgct | aggcatagaa | tgatggccca | atgcccatgc | atttagcaac | 900 |
| atctagaatt | taaccttaat | gcattttaat | tattgaatct | tcacaaaggc | atttgggaga | 960 |
| taggtagtta | aaataggctt | gtcatcgtga | ggcatcaagg | gcaagtaaaa | ttaatagatg | 1020 |
| tgggtagaac | taattcaact | gcattggtaa | tgaacatcat | aaattcattc | atcgtaggcc | 1080 |
| aattaggttt | gtccggtctt | ggcattttca | tcaattgtct | tcctaaatta | tttgatctaa | 1140 |
| tagcaacaat | ttattcttat | gcctattcct | gtttttacta | tttactttta | cttacaaatt | 1200 |
| gaagagtatt | caataaagtg | caataaaatc | cctatggaaa | cgatactcgg | acttccgaga | 1260 |
| attactactt | agaacgattt | ggtacacttg | tcaaacacct | caacaagttt | ttggcgccgt | 1320 |
| tgtcggggat | tttgttctcg | cacttaattg | ccatactata | ttagtttgta | agcttaattc | 1380 |
| ttctttttctt | ggctcattct | tttattattc | tttactttac | tttttcttct | atcctttctt | 1440 |
| tcttctccca | taaattgcac | gggtagtgcc | tttttgtttt | tatacgaggt | agaactgcat | 1500 |
| ctggagacgt | tgttcctatt | aacttagaaa | ttgaagctac | gtgtcggcgt | aacaacgctg | 1560 |
| caagaagaag | aagggagcaa | gacatagaag | gaagtagtta | cacctcacct | cctccttctc | 1620 |
| caaattatgc | tcagatggac | ggggaaccgg | cacaaagagt | cacactagag | gacttctcta | 1680 |
| ataccaccac | tcctcagttc | tttacaagta | tcacaaggcc | ggaagtccaa | gcagatctcc | 1740 |
| tactcaaggg | aacctcttcc | atggtcttcc | aaatgaagat | ccatatgcgc | atctagcctc | 1800 |

-continued

| | | | | |
|---|---|---|---|---|
| atacatagag | atatgcagca | ccgttaaaat | cgccggagtt | ccaaaagatg cgatactcct | 1860 |
| taacctcttt | tccttttccc | tagcaggaga | ggcaaaaaga | tggttgcact cctttaaagg | 1920 |
| caatagctta | agaacatggg | aagaagtagt | ggaaaaattc | ttaaagaagt atttcccaga | 1980 |
| gtcaaagacc | gtcgaacgaa | agatggagat | ttcttatttc | catcaatttc tggatgaatc | 2040 |
| ccttagcgaa | gcactagacc | atttccacgg | attgctaaga | aaacaccaa cacacagata | 2100 |
| cagcgagcca | gtacaactaa | acatattcat | cgatgacttg | caaccttaat cgaaacagct | 2160 |
| actagaggga | agatcaagct | gaagactccc | gaagaagcga | tggagctcgt cgagaacatg | 2220 |
| gcggctagcg | atcaagcaat | ccttcatgat | cacacttatg | ttcccacaaa aagaagcctc | 2280 |
| ttggagctta | gcacgcagga | cgcaactttg | gtacaaaaca | agctgttgac gaggcagata | 2340 |
| gaagccctca | tcgaaaccct | cagcaagctg | cctcaacaat | acaagcgat aagttcttcc | 2400 |
| cactcttctg | ttttgcaggt | agaagaatgc | cccacatgca | gagggacaca tgagcctgga | 2460 |
| caatgtgcaa | gccaacaaga | cccctctcgt | gaagtaaatt | ataggcat actaaatcgt | 2520 |
| tacggatttc | agggctacaa | ccagggaaat | ccatctggat | tcaatcaagg ggcaacaaga | 2580 |
| tttaatcacg | agccaccggg | gtttaatcaa | ggaagaaact | tcatgcaagg ctcaagttgg | 2640 |
| acgaataaag | gaaatcaata | taaggagcaa | aggaaccaac | caccatacca gccaccatac | 2700 |
| cagcacccta | gccaaggtcc | gaatcagcaa | gaaaagccca | ccaaaataga ggaactgctg | 2760 |
| ctgcaattca | tcaaggagac | aagatcacat | caaaagagca | cggatgcagc cattcggaat | 2820 |
| ctagaagttc | aaatgggcca | actggcgcat | gacaaagcc | aacggccac tagaactttc | 2880 |
| ggtgctaaca | tggagaagaa | ccccaaggaa | gaatgaaaag | cagtactgac ttgagggcag | 2940 |
| agaagagcgc | aggaggaggg | taaggttgaa | ggagaagact | ggccagaaga aggaaggaca | 3000 |
| gagaagacag | aagaagaaga | gaaggtggca | tcaccaccta | agaccaagag ccagagagca | 3060 |
| agggaagcca | agaaggaaga | accactagcc | cttccacagg | atctcccata tcttatggca | 3120 |
| cccaccaaga | agaacaagga | gcgttacttt | agacgtttct | tggaaatatt caaagggtta | 3180 |
| gaaatcacta | tgccattcgg | ggaagcctta | cagcagatgc | ccctctactc caaatttatg | 3240 |
| aaagacatcc | tcaccaagaa | ggggaagtat | attgacaacg | agaatattgt ggtaggaggc | 3300 |
| aattgcagtg | cgataataca | aaggaagcta | cccaagaagt | ttaaagaccc cggaagtgtt | 3360 |
| accatcccgt | gcaccattgg | gaaggaagcc | gtaaacaagg | ccctcattga tctaagagca | 3420 |
| agtatcaatc | tgatgcccctt | gtcaatgtgc | aaaagaattg | ggaatttgaa gatagatccc | 3480 |
| accaagatga | cgcttcaact | ggcagaccgc | tcaatcacaa | ggccatatgg ggtggtagaa | 3540 |
| gatgtcctgg | tcaaggtacg | ccacttcact | tttccggtgg | acttttttat catggatatc | 3600 |
| gaagaagaca | ctgagattcc | ccttatctta | ggcagaccct | tcatgctgac tgccaactgt | 3660 |
| gtggtggata | tggggaatgg | gaacttagag | ttgactattg | ataatcagaa gatcacctt | 3720 |
| gaccttatca | aggcaatgaa | gtacccacag | gagggttgga | agtgcttcag aatagaggag | 3780 |
| attgatgagg | aagatgtcag | ttttctcgag | acaccataga | cttcgctaga aaagcaatg | 3840 |
| gtaaatgctt | tagactgtct | aaccagtgaa | gaggaagaag | atctgaaggc ttgcttggaa | 3900 |
| aacttggatc | aagaagacag | tattcctgag | ggagaagcca | atttcgagac gctagagaag | 3960 |
| gaagttccgt | ctgagaagaa | gaagatagag | ttgaagatat | tgcctaatca tttgaagtat | 4020 |
| gtgttcttgg | aggaagataa | gcctatagtg | atcagtaatg | cactcacaac agaggaagaa | 4080 |
| aataggttgg | tagacgtcct | aaagaaacac | agggaagcaa | ttggatggca catatcggat | 4140 |
| ctcaggaatt | agccctgcct | actgcatgca | catgataatg | atggaagagg actacaagcc | 4200 |

-continued

```
agtccgacaa ccctagaggc ggctgaatcc aacaatgaag gaagaggtaa gaaaggaggt    4260
gctcaagctt ttggaggctg ggttcatata ccccatctct gatagcgctt gggtaagtcc    4320
agtacaggtg gttcctaaga aaggcggaat gacagtggta cgaaatgaga ggaatgactt    4380
gataccaaca cgaactgcca ctggttggtg gatgtgtatc gactatcgca agttgaatga    4440
agccacacag aaggaccatt tccccttacc tttcatggat tagatgctgg aaaggcttgc    4500
agggcaggca tactactgct tttggatgga tattcaggat acaaccagat cgcggtagac    4560
cccagagatc aggagaagac ggcctttaca tgccccttcg gcgtctttgc ttacagaagg    4620
atgtcattcg ggttatgtaa cgcactagcc atatttcaga ggtgcatgct agccattttt    4680
tcagacatgg tggagaagag catcgaggta tttatggacg acttctggat ttttggaccc    4740
tcatttgaca actatttgag gaacctagag atggtactac agaggtgcgt atagactaac    4800
ttggtactaa attgggaaaa gtgtcatttc atggttcgag agggcatagt cctgagccac    4860
aagatctcag ccagagggat tgaggttgat cagacaaaga tagacgtcat tgagaagttg    4920
ccgccaccaa tgaatgttaa aggtgtcaga agtttcttag gcatgcagg tttctacagg     4980 aggtccatca aggacttctc gaagattgcc aggcccttaa gcaatctgtt gaataaggat    5040
gtggctttta agtttgatga agaatgttca gcagcatttt tagacactaa agaataagct    5100
caccactgca ccagtaatga ttgcaccaga ctggaataaa gattttgaac taatgtgtga    5160
tgccagtgat tatgcagtag gagcagtttt gggacagagg cacgacaagg tatttcacgc    5220
catctattat gctagtaagg tccttaataa agcataacta aattatgcga ccacagaaaa    5280
gcagatgcta gccattgtct tttccttgga gaagttcagg tcgtacttga tagggtcgag    5340
ggtcaccatt ttcacaaatc atgctgccat caagcacttg ctcgccaaaa cagactcaaa    5400
gctgaggttg attagatggg tcctgctgat acaagaattt gacatcatca tcaaggacaa    5460 taaggatcc aagaatgtgg tagccaatca tttatcctga ttaaagaatg aagaagtcac     5520
caaggaagaa ccagaggtaa aaggagaatt tcctgatgaa tttcttttgt aggttaccac    5580
cagaccttgg tttgcagaga tggctaacta caaagccaca ggagtcattc cagaggagtt    5640
taattggagt cagaggaaga aattcttgca tgatgcacgc ttctatgtgt gggataatcc    5700
tcatttgttt agggcaggag ctgataatct attaaggaga tgcgtcacaa aggaggaagc    5760
acagagcatt ctttggcact gccacagttc accctatggc ggacaccaca gtggggacag    5820
aacagcagca aaagtgctac aatcaggttt tttctggcct tctatttta aagatgctta     5880 cgagtttgtg cgttgttgtg ataaatgcca gagaacaggg gggatatctc gaaggatgga    5940
gatgcctttg cagaatatca tggaagtaga gatctttgac tgttggggca tagacttcat    6000
ggggcctctt ccttcttcat acgagaatgt ttacatcctg gtagctgtgg attacgtctc    6060
caaatgggtg gaggccatag ccattccaaa agacgatgcc agggtagtga taaaatttct    6120
gaagaagaac atcttttccc attttggagt cccatgagcc ttgattagtg atggggaacg    6180
cacttctgca ataatcagtt gaagaaagtc ctggagcact ataatgtaag acataaggtg    6240
gccacacctt atcaccctca gacaaatggc caagtagaaa tttctaacaa agagctcaag    6300
cgaatcctgg agaagacagt tgcatcatca agaaagaatt gggccttgaa gctcgatgat    6360
actctttggg cctacagggc agcattcaaa actcccatcg gcttatcacc gtttcagcta    6420
gtgtatggga aggcatgtca tttaccagtg gagctggagc acaaagcata ttaggctctc    6480
gagttactca actttgataa caacgcatgc ggagaaaaga ggaagctaca gttgctggaa    6540
ttagaagaga tgagactgaa tgcctacgag tcatccaaaa tttacaacca aaagatgaag    6600
```

```
gcatatcatg acaagaagct acagaggaaa gaattccaac catggcagca ggtattactc    6660
tttaaatcaa ggctaaggct attcccaggt aagctgaagt ccaagtggtt agggccgttc    6720
ataatcaatg aagtcagacc tcacggagca gtagaattgg gggaccctag agaagagaac    6780
tttgagaaga aatggatcgt caatggacaa cgcttaaagc tttataacga aggacaacta    6840
gagcgattga cgaccatcat ctacttgaat gacccttgag gaggcctagt gtctagctaa    6900
agacaataaa ctaagcgctg gttgggaggc aacccaacat attttgtaaa aatgtagtca    6960
tttttctgta ttccttcaaa aaaaagggga aaagcccaat aggtgcaaat agaaaacagc    7020
aggtgcagaa agtaaagacc cagtaggtga agtcagcaat aggaggggtg ccaatagaag    7080
aagcgaagtg ggctgcacga agccacgcgc atctaggcgc taagcgccta ggtatatttt    7140
caattttta atttaaaaa ttctgaggga aaccaaggga cgcttccctt ggtatgctta    7200
gcgaccagat gcgcgctaag cgcgcgaacc ataaattgct ggacagtttt caaaactgtc    7260
ccacccctca gctgcccttt tgtatttta atttcaacca cctcattttt ttttctcttc    7320
tgcgcactcc cactccctat accctttttc tctacatttc tctaaactt actcgcctcc    7380
ctgtgcctct tcacgtagtt tttacgaaaa taggtgagat tgggaatctg gactgttgct    7440
gtaatacttt gcaggtacca tcacgctaag ccctacacaa aggcttagcg agaaaaagaa    7500
acatagaaag gaagaaagaa gcatgcgcta agcctgcgcc agacaggaca agaaaacaca    7560
gcatgcgttt agccggcacc tcgtgctaag cgcgctcatg agactcagtg aacgcgctaa    7620
gcatgggct gggccttagg gcccatcagc cctcgtgcct tactttctgc accctctttt    7680
tcactaacta cactcccttc tgaatttctt tttgcaccct cctctattac taaccacaat    7740
ctattttcc gtctttgttt ctttgttttt tcagatggcc tcccgcaaac gccgagctgt    7800
gcccacacct ggggaagcat caagctggga ctcttcccgc ttcacctcgg agatcatttg    7860
gcatagatac caggataaca ttcagctccg gaacattctt ctggagagga atgtcgagct    7920
cacacccagg atgtttgatg agttcctcca ggagctccag aggtgcagat gggaccaggt    7980
gttaacccga cttccagaga agaggattga tgtcgctctg gtgaaggagt tttactccaa    8040
cttatatgat ccagaggacc atagtccaaa gttttgtagg gttcaaggac aggtcatgtg    8100
gtttgatgca gagacgatta acgacttcct tgacacccca gtcatcctgg cagatgtaga    8160
ggagtaccca gcctactctc agtacctccg cactcctccc gatcatgatg ccatcctctc    8220
cactttgtgt actccagggg gacggtttgt tctgaatgtt gatggtgccc cctagaagtt    8280
gctgcggaag gatctgacga cactcgctca gacatagagt gtccttctt attttaacct    8340
tgttcttact tctcacactt ctgatattaa tgttgacagg gcccgtctca tatatggctt    8400
ggtgatgaag atggacctgg acgtggacag ttttatttcc cagcaaatca gtcagatcgc    8460
ccaatccaac acatccaggc tcgggttccc agcgttgatc acggcactgt gtgacattca    8520
gggggttgtt tctaacaccc tgattttga gttactcaat cctatgatta accttgcgta    8580
cattacacta ctaaaaaaaa gctatttac gacgcgcgtt ccacatcgtt tctgccaaaa    8640
atgtcgtaat aggagtagcg gtggcaattc cgtaaataag tgagcatttt atgtgccatg    8700
tgcatggcgc gtgacacatt caacgacgtt ggccatgggt gcccgtcttt gtaggtggcg    8760
cgctggtaac ttaagacggt gcacttaaaa acatcgtcgt tgaaattttg aatttcgaag    8820
acgttgctct taagccaccg tcgttaaggt tgatgtatat aatgttgtaa tttgcgctat    8880
ttcgtgaaca ctcgctcgag ctcccgcttc cctgtgtgtc tgaaatttct gtgtactgtg    8940
acctcgccat gacttgtggc gtttgcccac accccgtca cctcgtccgg catctcgtct    9000
```

-continued

| | | | | |
|---|---|---|---|---|
| tgtggtggca | ccgccgaagc | cagtgagtac | ccctttttgg | aggggtcgta acacggctgt 9060 |
| gttttgaagg | taaggttgtg | cgaagatttg | atgctccata | gttgttactt gctctgagtt 9120 |
| tttcttttag | tgatgtatct | tttacccctc | tttcagtgct | tcttccctca gaatttgatt 9180 |
| gccggtatta | gaaccccact | attcatcagg | tccaaacaag | cttaaatcat ggtaaatgta 9240 |
| cttcttgaca | atccaacat | ttgcaaggtg | gtttgacata | tgagaaatag ctttaaccta 9300 |
| atgttcttaa | atttattatg | aagctctcta | gcgattacga | aaatctctca atatcttctc 9360 |
| tctctgtctc | acatgcatca | ctgtaagata | ggtgtcaaaa | agaaaggatt gaagttaaat 9420 |
| ttaaacctaa | tgttttgaaa | tgaaggaaaa | aagaaagag | attaatgacg ctagggaact 9480 |
| tgaatgaaga | aagagaaagg | aacataatta | gtcctttgaa | ctgattgggg tggggagtgt 9540 |
| ggcacgaaac | ataatttcta | gttctatgga | tttattcgtg | acactgtggt aggaccaagc 9600 |
| aaactctgcc | cccagagtgc | gcagtgtctt | gcagtctgag | aggttctttt gttgggctag 9660 |
| tttgaggaat | tcttcattgc | agggttgagc | acggtggcca | atggccaagg agagaaaaga 9720 |
| cagtactgtc | aaaatggtta | atggtaagat | gagtgaagat | gacatgtttt tttgttgtct 9780 |
| ctttgtgtgt | ttcctttttgg | tgggaaaatg | tgatgcatag | agagatcga 9829 |

<210> SEQ ID NO 20
<211> LENGTH: 12571
<212> TYPE: DNA
<213> ORGANISM: Glycine max

<400> SEQUENCE: 20

| | | | | |
|---|---|---|---|---|
| gatcttaaat | tcttaaactt | tgataacagt | gcatacggag | agaagagaaa gttgcagtta 60 |
| ctggaactcg | aagaaatgag | gttgaacgct | tacgaatcat | ctaggattta caagcagaag 120 |
| gtaaaggcgt | atcatgataa | gaaattacaa | aagaaagaat | tccagccagg gcagcaagta 180 |
| ctactcttca | actccaggtt | gagattattc | acaggaaagc | tgaagtcaaa gtggtcagga 240 |
| tcgttcatta | ttaaggaaat | cagacctcac | ggagcggtag | aattggtgga ccctcgagaa 300 |
| gaaaattatg | agaagaaatg | gatcgtcaac | ggacaacgct | taaaaattta caatggagga 360 |
| caactagaga | agttgacgac | catcatgcat | ttaaaagatt | cttgaaagaa gccctatgtc 420 |
| tagctaaaga | cattaaacta | agcgctggtt | gggaggcaac | ccaacatact tatgtaaggt 480 |
| atttataagt | atttatattc | tgtctttatt | atattttgca | gttgttattt caggttaaaa 540 |
| gaaaaaacag | gggccctccg | gactcgcacc | agagtatcaa | cgtccatatc tgaggcaccc 600 |
| cctacttctc | agccttccgc | tccatcacct | actgatcttc | atgctcagat gttgcggtct 660 |
| attcacacag | gacaggagac | ccttatggag | aacatgcaca | agctgtcctt tcatctacat 720 |
| atggatccac | cactgatcac | tccataggtc | tatcgtcagc | gggtcgtctg gccatgagac 780 |
| cagctctcca | ctgacagggg | ggaagagccc | tctggagatg | ctgcagttga tgaagacctc 840 |
| atagcagact | tggctagtgc | tgattgggt | ccatgggcag | atttgggagg cggcacagga 900 |
| cactggtttt | atttttcttg | atgttttgt | ttatgtttaa | tgtttatgtt ttatgtcttt 960 |
| atgtttatt | tggtttctag | ttattatggt | cttaattgta | gttttatgtt caaaatgaaa 1020 |
| agcagtggta | ataatattag | atttgagcat | atgcgtgaat | aaataaattg catgataact 1080 |
| tgagaaatga | caattttgag | tttgttctaa | aaggtccaac | actggaaagg ctactagtca 1140 |
| ttggaaagca | ctggtcttgg | aagcaaaagt | caaatcaagg | aatgaaacat gattcacgga 1200 |
| aaaggaaagg | ttagcttgat | ggaatgaaga | cacatctggt | acgccaatac tgaattaatc 1260 |
| ccggtgagag | tgtgacctta | attgtgagag | aaaacgcctg | tttttaagct cttagttttg 1320 |

-continued

```
catcattctt ggactgttaa aattagttac ttaaggtgga tatgatcaag gccatgtttg    1380 tttttatttta cccactcagc caaaaagcca acccaacata attttatccc ttgcacccat    1440
attgagccaa aaagaattat aatgatttat ttgagtaaac ccctgagcca agaaaattgat   1500 attcctaacc ttgtgtagga ttctaagaga gcagtagggt tccaaatgct tataaggcct    1560
tattttgggg gattttgaac aaatgggtaa agtagccaag gtaataacac acattagaac    1620
acctctaaat aattgtgagc ccattactat tattattatt attattatta ttattattat    1680
tattattatt attattatta ttattattat tattggttat aaaaaaaaga agaaaaaaag    1740
agaaagaata agaagagaaa gggcaaagaa aaaaaatgaa aaagagaggt ttcagtggaa    1800
agtgctgaag gcaaaaaagg ctaagtggga aataggtctt ggcaagacct taaattttg     1860 gaatgtatgc tctcttataa ccttatattt tgaatttcca agaaaaacca tgattctttg    1920
ttagccaggc cccattacaa ggcatgaaag tccttagtga cccaccgaag gtaattaagg    1980
ctaaccttaa ccaagatgaa gtacaaaact cttgagtttt atttacaggt tgttaaaatt    2040
gcaaacactt gaccaggcac ttgtgagtag agagaaacac cagttttgta aggaagtaag    2100
gcaagccgga cctgttggaa ttccatataa ttgacttgtt tctgctcttg tgtttatgct    2160
tttatttcaa gatcatgaca gatgcaaaga gaccagccaa aggatcaagg aattgaagtc    2220
atggagagtg ttggaatgat tggaacttgc ttgagaaaat ttttgcttaa gaatggaata    2280
attttattct ttttatttgc ttggggacaa gcaaagttta atttggggga ttttgataac    2340
tgctaaataa tagtgaatta atagtggaaa attggtctga aattaactta gaattaatta    2400
tttagtagtt atttatgctt taatttggaa agatttaatt aattttgaat tctgattgca    2460
gatgtgaaaa agggaggtac aacaagcaaa aaggagcaaa aataaagaaa agaagaaga    2520 aaatcagacg aagacccaag cccaaatttt cacctataaa taagaaggtc agcctagcaa    2580
aacacacaca ctttcagaga gctcagtttt cagacttctg gcactcagtt ctctccttct    2640
ccttcccttt ttcttatatt cttattacct ttctttcacc cccttctcat tgtaaagccc    2700
tcttgactat gagtggctaa acccctagct agggcctggc aggcctaaaa agccaatgat   2760
gtatggagca tttcaagagt tatcaataaa gagaggattt ccttccaggt tctttattta    2820
ccgttctttc ttatttatcc tgtatttcgg accttatttt ctgttagggt ttagtccact    2880
cgggagaggg taaagcctaa ttaggggtaa ggaatgaata cttgaatcta ttttaagggt    2940
tagtccattc gggagagggt aaagcttaat agaacaataa aaggaagaaa ttatcgggtt    3000
atcattagag ggttttcctt ccaggttctt ttatctgctt ttctttctta ttctgcatct    3060
cagtctttat tttctgttag tcttttagtcc actcgggaga gggtaaagcc taattaaggg    3120
taaggaatga ttgcgtgaat ctgttttaag ggttagttca ctcaggagag ggtaacgctt    3180
aatagaacaa taaagaaaa aaatcacagg gttagcattg acccgatgcc catactttag    3240
caaacatata gaatttaatc ttaatgcatc ttagttattg agtctttgca aagggcattt    3300
ggaagatagg taattaaggt aggcttgtca tcatgaggca tcaggggcaa gtagatggat    3360
agatgtgggg cagaatcagt tcactggtat tgataacaga caaatcttga atccatatat    3420
ctaggctgat tagacttttt aggttttagc aattttatta tatagatttt attccctatt    3480
ttattgtttg aagtttctta ttctattgtt gggttttctt agaagtagct attccttatt    3540
ttactgttgg gttttcttag aaatagttat tccttattgt tgggtttctt agaagtagtt    3600
attccttatt ttactgttgg gttttattag gagtactat cccctgttta ggagtaggta    3660
tttaggctta ttagatttag taatatttta tagactttat tctttatttta ttgcttgagt    3720
```

```
ttcctttaat ttagaagtag ctgcttagat ttaaattact ttatctttat cctttaatct  3780
tatctttaaa tcttttatct tttccttatc ttatcttttta tctttcttta tcttttattt  3840
caaatttctt atcccttgct agatttaaat tgcatttaat tttatacact aaatttacaa  3900
tttgcaaact aaaaagtact tcacataagt gcaacaaaat ccctatggta cgatactcga  3960
cttaccgaga gattattact acgagcgatt tggtacactt gccaaagagc taacaaagat  4020
attgcctgat catctaaagt atgtgttctt ggaggaagat aaacctatag taatcagtaa  4080
cgcactcaca acaaaggagg aaaataggtt ggttgatgtc ctcaagaaat acagggaagc  4140
aattggatgg catatatcgg atctcaagga aattagccct gcttactaca tgcacagaat  4200
aatgatggaa gagaactaca agccagtccg acaaccccag aggcggctga atccaacaat  4260
gaaggaagag gtaagaaagg aggtactcaa gctcttggag gctgggctca tatacccctt  4320
ctctaacagt gcttgggtaa gcccagtaca ggtggttccc aagaaaggtg aaatgacagt  4380
ggtacgaaat gagaagaatg acttgatacc cagacgaact atcactggtt ggcgaatgtg  4440
tatcaactat cgcaagctga atgaagccac acgaaaggac catttcccct tacttttcat  4500
ggatcagatg ctagagagac ttgtagggca ggcatactac tatttcttgg atggatactc  4560
gggatataat cagatcgcgg tggacccag agatcaagag aaggcggcct ttacatgccc  4620
ttttggcgtt tttgcttata gaaggatgcc attcggttta tgtaatgcac cagccacatt  4680
tcagaggttc atgctggcca tttttcaga catggtgtag aaaagcattg aggtatttat  4740
ggacgacttc tgggttttg gaccctcatt taacagtttg aggaacctag agatggtact  4800
ttagagttga gtagagacta acttggtact gaactgggag aagtgtcact tcatggttca  4860
agagggcatc gtcctaggcc acaagatctc agcaagaggg attgaggtcg atcgggcaaa  4920
gatagacgtc atcgagaagc tgccaccacc actgaatgtt aaaggggtta gaagtttctt  4980
agggcatgca ggtttctaca agaggtttat caaggacttc tcaaagattg ccaggcccct  5040
aagtaacctg ttgaataaag acatggtttt caagtttgat gaagaatgtt caacagcatt  5100
ccaatcattg aagaataagc ttaccactgc acctgtaatg attgcacccg actgaataa  5160
agattttgaa ctaatgtgtg atgccaatga ttatgcagta ggagcagttc tgggatagag  5220
gcacgacaag gtatttcacg ccatctatta tgctagcaag gtcctgaatg aagcatagtt  5280
gaattatgca accatagaaa aggagatgct agccattgtc tttgccttgg agaaattcaa  5340
gtcatacttg atagggttga gggtcaccat tttcacagat catgctgcca tcaagcacct  5400
gcttgccata acagactcaa aaccgaggtt gattagatgg gtcctactgt tacaagaatt  5460
tgacatcatc atcaaggaca agaaaggatc gagaatgtg gtagccaatc atctatctcg  5520
attgaagaat gaagaagtca ccaaggaaga accagaggta aaaggtgaat tcctgatga  5580
gtttcttttg caggttaccg ctagatcttg gtttgcagac atggccaatt acaaagccac  5640
gggagtcatt ccagaggagc ttaattggag tcaaaggaag aaattcttgc acaatgcacg  5700
cttctatgtg tgggatgatc ctcatctgtt caaggcagga gcagataatt tactaaggag  5760
atgcgtcaca aaggaggaag cacggagcat tctttggcac tgccacagtt caccctatgg  5820
cggtcaccac agtggggaca gaacagcagc aaaagtgcta caatcaggtt ttttctggcc  5880
ctctatttt aaagatgctc acgagtttgt gcgttgttgt gataaatgcc aaagaacagg  5940
ggggatatct cgaagaaatg agatgccttt gcaaaatatc atggaagtag agatcttga  6000
ctgttgggc atagacttca tcgggcccct gccttcgtta tatggaaatg tctacatctt  6060
ggtagttgtg gattacgtct ccaaatgggt ggaagtcata gctacgccaa aggatgatgc  6120
```

```
caaggtagta atcaaatttc tgaagaagaa catttttttcc cgttttggag tcccacgagc   6180
cttgattagt gatagggggaa cgcacttctg caacaatcag ttgaagaaag tcttggagca   6240
ctataatgtc cgacataagg tggccacacc ttatcatcct cagacaaatg gccaagcaga   6300
aatctctaac agggagctca aggcgaatct tggaaaagac aattgcatca tcaagaaagg   6360
attgggcctt gaagctcgat gatactctct tggcctatag ggcagcgttc aagactctca   6420
tcggcttatc gccatttcag ctagtgtatg ggaaggcatg ccatttacca gtggagctag   6480
agcacaaagc atattgggct ctcaagttgc tcaacttcga caacaacgca tgcggggaaa   6540
agaggaagct acagatgttg gaattagaag agatgagact gaatgcctac gagtcatcca   6600
gaatttacaa gcaaaagatg aaggcatatc atgataaaaa gctacagagg aaagaattcc   6660
atccagggaa gcaggtatta ctcttaact cgaggctaag gctattccca ggtaagctga   6720
agtccaagtg gtcaaggcca tttatcataa aagaagtcag acctcatgga gcagtagaat   6780
tggtggaccc ttgagaagag aactttaaga agaaatggat cgtcaatcga cagcgcttga   6840
agccctacaa cggaggacaa ctcgagcgat tgacgaccat catctactta aatgatcctt   6900
gagaaggcct actgtctagc taaagacaat aaactaagca ctggttggga ggcaacccaa   6960
catatttttg taaaaatgta gttattttta ttttatgtaa aaaaaaacaa gagggcccaa   7020
taggtgcaaa tagcaaacag gaggtgcaaa aagcaaaggc ccaacaggtg aagacaacaa   7080
taggaagggt gccaatagca aaactgaagt gggctgcatg aagccgcgcg ctaagcgccc   7140
aggtatgttt ttaaaatctg atgggcaacc aagggacgct ttccttggtg cgcttagcgg   7200
ccacatgcgc gctaagcgcg taagtcataa attactggac agttttcgaa actgcccaac   7260
ccctcagctg cctcctccgc gttattaaat tacaaccatt tcatttcatt atccttctttt   7320 tctttcgcaa atctacccctt ctttgcacct ctgctactgt aaccccctgaa ttcttggtct   7380 tttcacacaa aacaatcact aacgaaggta aagaattgct ttgtatggat gttgttatga   7440
atgcacaggt aacagcacgc taagccctgc tcgacgctta gccaatgaag acggattgaa   7500
ggccataacg acgagctcgt taagcgtgac gaagcacgct aagcaggcgc ctgacaggac   7560
gagaaagcaa agcgcgcgct tagccggcac ttccgcgcta agcgcgctca tgaacatcac   7620
tgaacgcgct aaacgtgtgc cagaggcgct aaacgcgtgc cagaggcgct aaacgcgtgc   7680
attagtcaca gcaggatggt gctaagcgcg gggttgggcc tcagggccca tcaaccctcg   7740
caccttactt gttgcacccc tatttctact attcccactc ccttctaatt tcttttttgca   7800 cccccttct ttactgactg cacctctatt ttgattactt tttgcacccc ccctgattgc   7860
taacttcaga ctatctttct tgttttttgt ttttttggtt ttttggtcag atggcctcct   7920
gtaaacaccg agctgtgccc acacccgggg aagcgtccaa ctgggactct tcacgtttca   7980
ctttcgagat tgcttggcac agataccagg atagcattca gctccggaac atccttccag   8040
agaggaatgt agagcttgga ccagggatgt tgatgagtt cctgcaggaa ctccagaggc   8100
tcagatggga ccaggttctg acccgacttc cagagaagtg gattgatgtt gctctggtga   8160 aggagttta ctccaaccta tatgatccag aggaccacag tccgaagttt tggagtgttc   8220
gaggacaggt tgtgagattt gatgctgaga cgattaatga tttcctcgac accccggtca   8280
tcttggcaga gggagaggat tatccagcct actctcagta cctcagcact cctccagacc   8340
atgatgccat ccttctccgct ctgtgtactc caggggacg atttgttctg aatgttgata   8400
gtgccccctg gaagctgctg cggaaggatc tgatgacgct cgcgcagaca tggagtgtgc   8460
tctcttattt taaccttgca ctgacttttc acacttctga tattaatgtt gacagggccc   8520
```

```
gactcaatta tggcttggtg atgaagatgg acctggacgt gggcagcctc atttctcttt    8580
agatcagtca gatcgcccag tccatcactt ccaggcttgg gttcccagcg ttgatcacaa    8640
cactgtgtga gattcagggg gttgtctctg ataccctgat ttttgagtca ctcagtcctg    8700
tgatcaacct tgcctacatt aagaagaact gctggaaccc tgccgatcca tctatcacat    8760
ttcaggggac ccgccgcacg cgcaccagag cttcggcgtc ggcatctgag gctcctcttc    8820
catcccagca tccttctcag cctttttccc agtgaccacg gcctccactt ctatccacct    8880
cagcacctcc atacatgcat ggacagatgc tcaggtcctt gtaccagggt cagcagatca    8940
tcattcagaa cctgtatcga ttgtccctac atttgcagat ggatctgcca ctcatgactc    9000
cggaggccta tcgtcagcag gtcgcctagc taggagacca gccctccact gacagggggg    9060
aagagccttc tggagccgct gctactgagg atcctgccgt tgatgaagac ctcatagctg    9120
acttggctgg cgctgattgg agcccatggg cagacttggg cagaggcagc tgatcttatg    9180
ctttaatgtt ttcttttata ttatgtttgt gttctctttt atgttttatg ttatgttttt    9240
atgtagtctg tttggtaatt aaaaagaggt agtagtaaaa atattagtat ttcagtatgt    9300
gttttctgag taataagtgc atgataactc aagcaatcat aattctttag cttgttcaga    9360
aaggttcaac acttgagatg ccactgatcc ttggagaaac actggttctg gaagcaaaag    9420
tcaggtcaag aaatggaaca tgaatagcac agagtggaaa ggttagcttg atggaacaag    9480
gtcataactg gtacgccgaa tacttgttta agtccctgtg agcatggttg tcaaactcta    9540
gagtcaactc atagactctc atgagtttaa gagtttactt cagtcccgcg agttgactcg    9600
gaagcaaact cgcttttgag caaactcgtg gactcggagt gaactcatgt aaactcgtaa    9660
gagtctacga gttgactcta gagtttgaca accatgcata agtgttcaaa attaaagcat    9720
ttaaataatt aaaaaaagca caaatgtctt caaagaagca tgttcaatcc tctaatagga    9780
tcatcttcat gaatatcatc actttcatca tcatctccat ctccatcatc atcatcaagg    9840
tcttcctcag attgtgcatc atcattaggt tccacaaaga ttaaattatc tagatcaaaa    9900
gcttaaaata gatatcaaat atgctatatt agaaatagtt aaaacttaaa ataatacaca    9960
agcaaatttt aaatatgaga aagttcagaa attatacctt tccttggtgt tattaaagtt   10020 tcatttatc ttctcttttg cattttccat ctcctcacat atgaaaagca taattctatt   10080
gaatttcagt aacaagtttg atccaactcc aacattgtaa ggtcagttgt tgtgttttgt   10140
aatagactaa tatgaagtat gaagtatgaa ctatgaactt attgtcatct gtttgcaaat   10200
tggtgcattt tgaatatatt tacttattat ccatttttt tttttacga agtagactct   10260 cacgagtctg cgtagactct cgatatcgat aaccttgccg atgagagtgt gaacttaatt   10320
gtgagagaaa atgcctattt ttaagttcct ggttttgcat cattcttaga cggttagaat   10380
agttacttaa ggtggatatg atcaaggcca tgtttgtttg tttacctact tagccaaaaa   10440
gccaacctaa catagtttta ccccttgcac ccatgattga gccaactgat tattttgaat   10500
taaccttgag ccaattaaac aaaatcctga ccttttagga ttttaagaga gtaaaaatgg   10560
gttataaagg tcttaatttg ggggattttg ggaaataggt agccaagaca ataagtacag   10620
cacacaaagt aggacacctt ttacaaacag taggcccaat ttcgaaaaaa aaatgaaaag   10680
aatttaataa agggcagaaa caaagagca agagaggtgt caaagaaaa gtgttgtggg   10740 gaaataaaag ggctaagtaa aaaggcctag gcagaattgg aaattttgt tctcttttaa   10800 tcctaacttt gaatttccaa gaaaaccat gatttttgt aagccaggcc ccgatacaag   10860
ccaataaagt ccttagtgat ccaccaaagg taactagaga taactgtaac tgagatgaaa   10920
```

-continued

```
tgcaaaattt tgaagtgtta cttgcaggtt gttatcaaat tgcaaacact aaactaggca    10980
cttgtgagca gagggaaaca ccagccttgt gaggaaagta aggcaagcca aatttgattg    11040
agttccagat gactaactga ttcaattctt ctgttgtaat gctttcattt taagatgttg    11100
acagatgcag aaaggaccag tgaaagaagg aggaactgag ccattgatag tgttggaata    11160
tttaagaact tgcttgagaa tttacttgtt tttggttttc ttggggacaa gcaaagtttc    11220
atttggggaa ttttgataac tgctaaataa ttgtgaatta atagtaaaga attattcaaa    11280
ttttggcctg aaattaatta tttagcagtt atttgtgatt aaaagttaga aaattaatta    11340
aattgaattt ttggttgcag ataagaaaat tggagttaca ttaagcaaaa aaggcaacaa    11400
aaaatgaagg aaaagaagaa gtctgaagca ggcccagccc aacacgcacg ctaagcgcgt    11460
gtcacgcgct aagcgtgcaa ggcagtacag gcgctaagcg aggcgttaag ctcgaagatg    11520
cagaatccgt tacgcgcgct aagcaagggc cacgcgctaa gcgtgcgatc aacagaaac    11580 acacgctaag cctgcatctc gcgctaagcg cgcgatctga acgcgctaag cgcgaggtgt    11640
cgcgctaagc gcgcttacga aggcccaaaa cccactttag cagctataaa tagagagtca    11700
gtccaaggga acaacacat ctcgcctcag agcacttccc tcagcattct aagcctaagc    11760 tctcccttt ctctttgttt ttattatcct cattctttct ttcaccccca gttgtaaagc    11820
cctcaatggc catgagtggc taatctagta gctagggcct ggcaggccta aaagccaac    11880 gatatatggt gtacttcaag agttatcaat gcaaagaaga ttcattccag gtttttttgt    11940
tctaattatt ttcttttat cttgcattca tttcttgaat ttcttttggg ttttatttgc    12000
tcgggagagg gtatttccta ataagggttt aaggattaat gcatgcatca gttttagggg    12060
ttatacgctt gggaaagggt aacacctaat agaacatctt aagaaaagaa tcatcggtt    12120 agcattgcta ggcatagaat gataactcaa tgcccacgca tttagcaaca tctagaattt    12180
taccttaatg cattttaatt attgagtctt cgcaaaggca tttgggagat aggtagttaa    12240
aataggcttg tcatcgtgag gcatcagggg caagtaaaat taatagatgt gggtagaact    12300
gttacaaatg cattggtaat gaatatcata tttacatgca tcgtaggcca attgggtttg    12360
tccggtcttg gcatttatat taattgtctt tctaaaacta tttgatctag taatagcaat    12420
ctattcttgc acttactcct gtttttacta tttactctt acaaattgaa aagtattcga    12480
taaagtgcaa taaaatccct gtggaaacga tactcggact tccgaggttt actacttaga    12540
gcgatttggt acacttgcca aagtctcaac a                                  12571
```

<210> SEQ ID NO 21
<211> LENGTH: 4609
<212> TYPE: DNA
<213> ORGANISM: Glycine max

<400> SEQUENCE: 21

```
gatctcccat atcctatggt acccaccaag aagaacaagg aacattactt ctgacgtttc      60
ttggaaatat tcaaaggact ggaaatcacc atgccattcg gggaagcctt acagcagatg     120
cccctctact ccaaatttat gaaggacatc ctcaccaaga aggggaagta tattgacaat     180
gagaatattg tggtagggggg caactgtagt gcaataatac agaggaagct acccaagaag     240
tttaaggacc ccggaagtgt taccatcccg tgcaccatag gaaaggaaga ggtaaacaag     300
gccctcattg atctaggagc aagtatcaat ctaatgccct tgtcaatgtg cagaagaatc     360
aggaatttga agatagatcc caccaagatg acacttcaac tggcagaccg ctcgatcaca     420
agaccataca gggtggtaga agatgtcctg gtcaaggtac accacttcac ttttccggtg     480
```

-continued

| | | |
|---|---|---|
| gactttgtta tcatggatat cgaagaagac acagagattc cccttatctt aggcagaccc | 540 |
| ttcatgctga ttgccaactg tgtggtggat atggggaatg ggaacttgga ggtgagtatt | 600 |
| gacaatcaga agatcacctt tgaccttttc aaggcaataa agtacccata ggagggttgg | 660 |
| aagtgcttta gaatggagga gattgataag gaagatgtca gtattctcga gacaccacag | 720 |
| tcttcgctgg ggaaagcaat ggtaaatgct ttagactgtc taaccagtga agaggaagaa | 780 |
| gatctaaagg cttgcttgga agacttggat tgacaagaca gtattcctaa gggagaagcc | 840 |
| agatttgaga ctctagaaaa ggaagttccg tccgagaaga agaagataga gttgaagata | 900 |
| ttgcccgatc atctgaagta tgtgttcttg gaggaagata aacctgtagt gatcagtaac | 960 |
| gtactcacaa cagaggagga aaacaggtta gtagatgtcc tcaagaaaca cagggaatca | 1020 |
| attggatggc acacatcgga tctcaaggga attagccctg cttactgcat gcacaggata | 1080 |
| atgatggaag aggactacaa gccagtctga caaccccaga ggcggctgaa tccaacaatg | 1140 |
| aaggaagagg taagaaaaga ggtactcaag ctcttggagg ttgggctcat atacccatc | 1200 |
| tctgacaacg cttgggtaag cccagtacag gtggttccca agaaaggtgg aatgacagtg | 1260 |
| gtacaaaatg agaggaatga cttgatacca acacgaacag tcactggctg gcgaatgtgt | 1320 |
| attgactatc acaagctgaa tgaagctaca cggaaggacc atttcccctt acctttcatg | 1380 |
| gatcagatgc tggagagact tgcagggcag gcatactact gtttcttgga tggatactcg | 1440 |
| ggatacaacc agatcgcggt agaccccata gatcaggaga agacggtctt tacatgcccc | 1500 |
| tttggcgtct tgcttacag aaggatgtca ttcgggttat gtaatgtacc agccacattt | 1560 |
| cagaggtgca tgctgaccat ttttcagac atggtggaga aaagcatcga ggtatttatg | 1620 |
| gacgacttct cggtttttgg accctcattt gacagctgtt tgaggaacct agaaatggta | 1680 |
| cttcagaggt gcgtagagac taacttggta ctgaattggg aaaagtgtca ttttatggtt | 1740 |
| cgagagggca tagtcctagg ccacaagatc tcagctagag ggattgaggt tgatcgggcg | 1800 |
| aagatagacg tcatcgagaa gctgccacca ccactgaatg ttaaaggggt tagaagtttc | 1860 |
| ttagggcatg caggtttcta taggaggttt atcaaggatt tctcgaagat tgccaggccc | 1920 |
| ttaagcaatc tgctgaataa agacatgatt tttaagtttg atgaagaatg ttcagcagca | 1980 |
| tttcagacac tgaaaaataa gctcaccact gcaccggtaa tgattgcacc cgactggaat | 2040 |
| aaagattttg aactaatgtg tgatgctagt gattatgcag taggagcagt tttgggacag | 2100 |
| aggcacgaca aggtatttca caccatctat tatgctagca aggtcctgaa tgaagcacag | 2160 |
| ttgaattatg caaccacaga aaaggagatg ctagccattg tctttgcctt ggagaagttt | 2220 |
| aggtcatact agatagggtc gagggtcacc attttcacag atcatgctgc catcaagcac | 2280 |
| ctgctcgcca aaacagactc aaagctgagg ttgattagat gggtcatgct attacaagag | 2340 |
| tttgacatca ttattaagga caagaaagga tccgagaatg tggtagctga tcatctatct | 2400 |
| cgattaaaga atgaagaagt caccaaggaa gaaccagagg taaaggtga atttcctgat | 2460 |
| gagtttcttt tgcaggttac cgctagacct tggtttgcag acatggctaa ctacaaagcc | 2520 |
| atgggaatca tcccagagga gtttaattgg agtcagagga agaaattttt gcacgatgca | 2580 |
| cgcttatatg tgtgggatga tcctcatttg ttcaaggcgg gagcaaataa tttattaagg | 2640 |
| agatgcgtca caaggagga agcacgaagc attctttggc actgccacag ttcaccctat | 2700 |
| ggcatacatc acagcgagga tagaacaaca gcaaaagtgc tacaatcaag ttttttctag | 2760 |
| cccttttattt ttaaagatgc tcacgagttt gtgcattgtt gtgataaatg tcagagaaca | 2820 |
| aggggggatat ctcgaagaaa tgagatgcct ttgcagaata tcatggaggt agagatcttt | 2880 |

-continued

| | |
|---|---|
| gatagttggg gcatagactt catggggcct cttccttcat catacaggaa tgtctacatc | 2940 |
| ttggtagctg tggattacgt ctccaaatgg gtggaagcca tagccacgct gaaggacgat | 3000 |
| gccaggtag tgatcaaatt tctgaagaag aacatttttt cccatttcgg agtcccacga | 3060 |
| gccttgatta gtgatggggg aacgcacttc tgcaacaatc agttgaagaa agtcctggag | 3120 |
| cactataatg tccgacacaa ggtggccaca ccttatcaca ctcagacgaa tggccaagca | 3180 |
| gaaatttcta acagggagct caagcgaatc ctggaaaaga cagttgcatc atcaagaaag | 3240 |
| gattgggcct tgaagctcga tgatactctc tgggcctata ggacagcgtt caagactccc | 3300 |
| atcggcttat caccatttca gctagtatat gggaaggcat gtcatttacc agtagagctg | 3360 |
| gagcacaagg catattgggc tctcaagttg ctcaactttg acaacaacgc atgcggggaa | 3420 |
| aagaggaagc tacaactgct ggaattagaa gagatgagac tgaatgccta cgagtcatcc | 3480 |
| aaaatttaca agcaaaagac aaaggcatat catgacaaga agctacaaag gaaagaattc | 3540 |
| cagccagggc agcaggtatt actcgttaac tcaaggctaa ggctattccc aagtaagctg | 3600 |
| aagtccaatt ggtcagggcc attcataatc aaagaagtca gacctcacag agcagtagaa | 3660 |
| ttggtggacc ctagagaaga gaactttgat aagaaatgga tcatcaatgg acagcgcttg | 3720 |
| aagcctata acggaggaca actagagcga ttgacgacca tcatctactt aaatgaccct | 3780 |
| tgagaaggcc tactgtcgag ctaaagacaa taaactaagc gctggttggg aggcaaccca | 3840 |
| acatattttg taaaaatgta gttatcttca ttctatgtaa aaaaaaagcc caacaggtgc | 3900 |
| aaataggaaa cacgaggtgc aaaaagcaaa ggcccaacat gtgaagacaa caataggagg | 3960 |
| ggtgccaata gcaaaactga agtgggctac acgaagctac gtgcttagct cgcgtccgcg | 4020 |
| cgctaagcgc ccagattgca caaaatagg tgagacttgg aatctggact attgctgtaa | 4080 |
| tatcttgcag gtaccattac gctaagccct acacagaggc ttagcgagaa caggcagcat | 4140 |
| ggaaaaaggg aaggaggagc gcgctaagcc acaacaagta atagaagaaa acgaagcacg | 4200 |
| cgcttagcgg gcactgccgc gctaagcgca ctcttcaaca tcagtgaacg cgctaagcgc | 4260 |
| gtgccagaag cgctaagcgc gtgtcaccgt caccagcagg aaggcgctaa gcgcgaggtt | 4320 |
| gggccttagg gcccatcagc cttcgcgcct tactttttgc acaccccttc tttactaact | 4380 |
| gcacccctat tttgatttct ttttgcaccc cctctgttta ctaactgcag tttgtttctg | 4440 |
| ctgtttcttg tttttgtttc agatggcctc ctgcaaacgc cgagccgtgc ccacacccag | 4500 |
| ggaagcgtct aattgggact cttcccgttt cacttcagag attgcatggc acagatatca | 4560 |
| ggacaacatt cagctctgga acatcctttc ggagaggaat gtcgagctc | 4609 |

<210> SEQ ID NO 22
<211> LENGTH: 9139
<212> TYPE: DNA
<213> ORGANISM: Glycine max

<400> SEQUENCE: 22

| | |
|---|---|
| acctggttgt tgtatgctt gtcttaatgc ggataggttg tcaagtagct ttagtgctaa | 60 |
| cactgagaag aatccgaagg aagaatgtaa agttttaatg acaaagagca gaatggaaat | 120 |
| tcaagttgat gaagttagag ctgaagagaa ggtggaggga tataaacaac agtcgatagc | 180 |
| tgagcctgca ctggaactag tttccgatct tattgaactt gaggaagttt tggaagagga | 240 |
| agatgaccaa caggagagag agacaccaat aaaagatagt caagaaggaa taagatgaa | 300 |
| ggaagagcat gaaaaagaaa aacaaaaaga aaagaagaa atagaaaaag aaaataataa | 360 |
| aaaaaatgaa aaataaaaaa agatggttga tgaggagaaa aaaagagca agagtgaggt | 420 |

```
ttcaagagaa aaaaagagag agattacttc agctgaaggc aaggaagtac catatctatt      480
ggtaccttcc aagaaggata aagagcaaca cttagccaga tttcttgaca tcttcaagaa      540
actgaaaatt actttgcctt ttggagaagc tctccaacag atgccactct atgccaaatt     600
tttaaaagac atgctgacaa agaagaacta gtatatccac agtgacacaa tagttgtgga     660
aggaaattgt agtgctgtca ttcaacacat ccttccccca aatcataagg atcccggaag     720
tgtcactata ttatgttcca ttagcgaggt tgttgtgggt aaagctctca tagacttggg     780
agctagtatc aatttaatgc ctctctcaat gtgtcgacga cttggagaga tagagataat     840
gcccacacgc atgacccttc agttggttga tcactccatc acaagaccat atggagtgat     900
tgaggatatg ttgattcagg tcaagcaact tgtattccct gtagatttcg tggttatgga     960
tatagaggag gatcctgaca ttcccataat cttgggacgt cctttcatgt ccgcgaccaa    1020
ctatatagta gatataggga aaggcaagtt agaattgggt gtggaggatc agaaagtctc    1080
attcgactta tttgaagcaa ataagcatcc aaatgataag aaagcttgct ttgatctaga    1140
caaggtagaa caataaatag aattagctac tatagccatg gtactgaact ctcctttgga    1200
aaaagcattg attaatcatg tagaatgtct tactaaagag gaggaacatg aagtgcaaac    1260
ttgtattaaa gagttggatg gtgcaggaga aaattctgag ggacaggatg catttcaaga    1320
attgaagaat ggtgggcaaa tagaaaaacc aaaagtagaa ttgaagacct tgcctgcaca    1380
tttgaagtat gtatttctcg aagacaatga ctccaaacca gtgattatta gcagctcgtt    1440
gaagaaaata gaagatcaac tggtgaagat tttgaagaga cacaaagctg caattggatg    1500
gcacatatct gacttgcaag gaattagtcc atcttattgc atgcacaaaa tcaatatgga    1560
agctgattac aaaccagtga gagagcctca agaagactg aacccaatca tgaaagaaga    1620
gatgcataag gaggtgctta aattgtagga agcaggcctt atttaccct cctcggatag     1680 tgcatgggtt agccttgtgc aggttgtccc caagaaagga ggtatgacag tcattaaaaa    1740
tgataaagat gagttaatat ccataaggac tgtcaccggg tggagaatgt gcattgacta    1800
tcggaagctg aatgatgcca ctcggaagga ccattatcca cttcctttca tggaccaaat    1860
gcttgaaaga cttgtaggga atcctatta ttgttttctc gatgagtact ctggctataa     1920
ttagattgtt gttgatccta agatcaaga aagactgct tcacctacc ctttggtgt        1980 attcgcatat cggcacatgc cttttggtct gtgcaatgcc ccagctacat ttcagaggtg    2040
tattatggca attttttctg atatggtgga aaaatgcatc gaagttttca tggatgattt    2100
ctctattttt gggccatcct ttaaggggtg cctattaaat cttgaaagag tattacagag    2160
atgtgaagag tccaatctag ttctcaattg ggagaaattc catttcatgg ttcaagaagg    2220
aatagtgctg gggcataaaa tttcagtaag gggaatagag gtggacaagg caaagattga    2280
tgtaattgag aaacttcctc ctccaatgaa tgccaaagaa gtgagaagtt tcttatgaca    2340
tgcaggattc tacagatgat tcataaaaga tttctcaaaa gtcgcccagc cacttagcaa    2400
tctgttgaat aaagatgttg cttttgtgtt caatcaagag tgcatggaag catttaatga    2460
tctgaaaacc agattagtgt ctgctccagt aagtatagca ccagattggg gacaagaatt    2520
tgagttgatg tgtgatgcaa gtgactatgt cgtaggtgta gtgcttcgac aacgaaggg    2580 aaaacttttt catgctatat actacgccaa caaggttcta aatgatgcac aggtgaacta    2640
tgctaccata gaaaagaaa tgctggcaat tgtctatgca cttgaaaagt ttagatctta    2700
tttggtaggt tcaagagtta tcatctacat cgatcacgca gctattaaat atttgctcaa    2760
caaggctgat tccaaaccta gattgataag atggatcttg ttgttgcaag aatttgattt    2820
```

-continued

```
ggtgattcgg gataaaaagg gatcggaaaa tgttgtagct gaccatttgt ctagattggt    2880
gaatgaggaa gtcacattga agaagcaga agtgagagat gaattccctg atgaatcatt     2940
attcttagtg agtgagagac cttggtttgc cgatatggcc aacttcaaag ctacaagaat    3000
catcccaaag gacttaactt ggtagcagag gaagaaattc ctacatgatg ctcgattcta    3060 tatctggggtt gatcctcatt tgttcaagat aggagctgac aatctcctat gaagatgtgt   3120
gacacaagaa gaggccaaga acatattatg aaattgccac aattctccat gtggcagcca   3180
ttatggtgga gataagacga tgaccaaggt tttgcaatct ggattctttt ggcccatgct    3240
tttcaaagat gctcatcagc atgtgcaaca ctgtgatcaa tgtaagagga tgagggtat    3300 atcaagaaga aatgaaatgc ctctacagaa tattatggag gttgaggtat tcaattgcta   3360
ggggattgat tttgtaggtc ccttcccttc gtcttttggc aatgaatata tactagtggc    3420
gattgactat gtctctaaat tggttgaagc agtggctacc ccgcataatg atgctaagac    3480
tgtggtaaag tttctaaaga aaaacatttt ctcaagattt ggggtgccta gaattctgat    3540
taacgatgga ggcacacact tctgcaataa tcatctatag aaggtgttga agcaatataa    3600
tgtgacacaa agtagcatca ccttatcacc cccagaccaa tgggcaagca gaagtatcaa    3660
acagggaatt gaaaaagatt ttggagaaga ctatagcttc tactagaaaa gactagtcta   3720
tcaaattaga tgatgctttta tgggcataca gaacaacatt caagactccg ataggattat    3780
ctccatttca gatggtgtac ggcaaggctt gtcacttacc agtggagatg gaatataaag    3840
catactaggc cttgaagttt ttgaactttg atgaagccgc atccagagaa caaggaggc     3900 tgcaacttt ggagttggga gatatgagat taactactta tgaatcttca aggctataca    3960
aagaaagggt caaaaagtat catgacaaga agctgctcaa gaaggacttt cagccaggac    4020
gacaagagtt gcttttcaac tcaagactta aattgttccc tggaaagctt acatcgaaat    4080
ggtctggacc atttaccatc aagaaagtcc gcccatatag agcagtggag ctttgtgatc    4140
ctcaatctaa agatcctgac aggacatggg tagtgaacgg acaaaggttg aatcaatatc    4200
atggttcatg caatcctacc cctcaagggt attggataga agactccaag aggattgggc    4260
tagagctgct aaagaaggcc ttggggttct catgaacccc agggtaaatt tctgagccca    4320
tggaccaagg ttgggtcctc tcttcttgt aaatattaga ataggttttt ccttcttctc     4380
aggctaagca ccaatatgct tctgttttc agtcctttga ataaggctaa gcgcagctgc    4440
tgcactaagc ccttgttgtg tgtcaaggag gttgagctaa gcgtgcccta ctgcgctaag    4500
ctcaactatc tcactatttt tgtgttttta tggtcaggct aagcgcgccc tatgtgctaa    4560
gcctaagggt cattctggtg agcgtgagct aagcgcgcca tgctgcacta agcttagacc    4620 ctttttttgtt ttgaaaattt tagacttagg ctaagcccaa catgctacgc taagcctatc    4680
tacagaaaaa tattttgtgt ctttaggcta agctcgagtc tactgcgctt agctcatgag    4740
taatatttta taaggcgcgc taagcccagc ctgctgcgct aagtgcccag ttcagttttc    4800
agctttaatt ttttgttttt gatagaaata atcttattta accttgtggt ttgattttat    4860
tctttcagat agcatcaaag aagagaaagg cacctgccac accttcccag gtctgatatg    4920
gccgatcgag gttcacttct cttgtggcct aggaaaggta cactgatatt gtggtaccca    4980
ggaagatact ccctgagtgg aatgtggtaa tctaccacac tgagtttgat gagtttaagg    5040
aagaactaga gagaagaaaa tgggatgagg aattgaccag ttttgatgaa ggcaacattg    5100
atgttgccat tctgaaagag ttttatgata acctctatga ttccgacgat aaatcaccta    5160
agcaggtgag ggtgagaggc catttggtga agtttgatgc agacactctg aacactttct    5220
```

```
tgaagacccc tgtgataatt gaagaggggg aaaagctgcc tgcctactct agatttgcac   5280
tcttgagtcc tgatcctcaa gagttggctg ctaagctctg catcccaggg agggaatttg   5340
agcttaatgt tgacgacttg ccactaaaga tcctcaggaa gaaaatgacc acactcgctc   5400
agactaggag tgttctttct tactccaact tggtccctac ctcccacact tctcacatca   5460
cactggatcg ggccaagttg atttatggca ttatcatgaa gatggacatg aatttgggct   5520
acctcatctc ccaccagatt tctatcattg cccagcatga ctcctctagg cttggattta   5580
caaccttaat catagctttg tgtaaagcta aggagtcac  attagattcc aaatctttgg   5640
agagtcttag ccctgccatt aacatggcat atataaagaa gaactgttgg aatctagatg   5700
atccaacagt gacattcaga gagccaagga aggccagggg taaaagaatc gaggctcccc   5760
ctacttcagc agcaccaggt gcttctgctc cttcttcatc ttctttacca gatccttcag   5820
caccatccac ttcgactcca catcttccat ggttactagc ttcagctccc actcccttac   5880
cagcttcaat tcagctcctt ctacaggacc ctcctcattc acctctaaga cattatttgc   5940
tatgctgcaa agcctgcaca aaggccagat catcatcata cagaggttgt agagctctgg   6000
ccagaaacca accatgagta tagaggagtt ccttgcacaa gtggcttgcc caggagtcga   6060
gccttctcct tctggagggg gtgaggcctt tgcagcccaa gagccttgcc agcagagaag   6120
cctgtgccag aagcagagga tgagcttgtt cttcctgagc catttgttta tgagattgat   6180
ccagtcgctc aggaggaagc agcagctcag gagcttcctg cacctatttc tgaggatacc   6240
ctgccatctg caccagcatt ggagtaagag cagcctagtt cacaggatcc accagctgct   6300
ccaatgctgg atctgaacga gcatgcagaa gatcagcagt aggatgatca tgagttttaa   6360
attctacata gttttaaaa  ttttgcaaat tatgaatagt ttcttttatc aattatttag   6420
ttcatgtcaa ttatttgttt atgctttatt agtctttaaa ttttagtctt ttaaattttt   6480
gttgtttgag tgttgatagc ttgtacaaaa gcatgtttga acagtgaact tattgattat   6540
gatattcagt ggtgtgattt cttatgaatg aagtgtttgt gaatgacttg aatgagaaaa   6600
tgtatgaatt gagtggactg gaatgattag atgtttgttt tgatcaagct tgtagtcatt   6660
agaagaaaaa gaacatgtga ttagaagtat gactgaaaat gttagtcagt tgtcaaatt    6720 gattgtgaag gaatgcattg accgtatccc agtgagagtg tgatccttaa attttgagag   6780
aaatgacttt aatttagcac taattttttgc acgaatcttt gaagtatgga ttgaatgcat   6840
gaattgagga taatgaaggc catgttttga ttgtgatagc tatttagcca aaaagctgac   6900
cttgtgcttg aatgatttat cccttgcacc cagtttgagc tgaatgaatt attgattgat   6960
tgaaccttga gcctatatag tgttttctcc tgcttccttg tcttaggtta taggagagca   7020
taatccacag aaaagcttgg ttcaaggcaa atttgttcca aatttggggg agacactggg   7080
taaagaaata aaatggtcaa aacagagcaa catatacaca ttgttttctg tatgtaaaaa   7140
aaactgtaag tataaataaa aatgtataaa agtgtgtgtg ctgcaaatca atcaatgaa    7200 agctaagtgc ttaataaaag gcaagtatgg ggtaggaatg aataaaaaaa aaagtaaagg   7260
tttatctatg gatgaatgct ctcgtagaat ctaagctttt gaatcctaga aaaccatga    7320 tttgttggca gcctaacctc attacaagcc tagaaagtcc tttggattca ttttgtgtgt   7380
ttatttctgt atggtatgag atgaaatgca aaagttagga cttgtgttag ttgttcatga   7440
tggaatgagc ctaaacactt aagcttgagt gaaacaatga ctgtgaggct ttggttgatg   7500
attttttcct tgatatctgt cattctcact agcttatttt agttgtgact ctaatgcata   7560
tgttcctatc tttgaaaaac tgcatgtttg tgaaaagaaa ttggttgaag cattccatga   7620
```

-continued

```
tattcatttc atatgattga atttctctgt gaggagaaca ccatttggat tgaccactgt    7680
attttgtcac ttgaggacaa gtgaactgtt ctttctttgc ttgaggacaa gcaaaacttt    7740
aaatttgggg gagtatgtta gtcatcttat acgactaact tttgtataga aaaaattttc    7800
caaaacttgt atagtttctc caatttatag ttattttgta gggatttgta aataaatctt    7860
gttttattgt tatagttgtc tctagaatat tttccatttg atttaatgat gaaatctgtt    7920
caatttcagg ttaaaagagg ctaagtcttg aagtgctaaa agtgggattt acgctcagct    7980
caccatttgg cctcaacgcg catccaccgc taagcacagc ttcagcgcac ttagtgtgac    8040
agaagaatct ggcagagcat aaatatcaag gccgcttgct aagcaagatg gttgtcttta    8100
gccagactca gcgcatgact ggcgctaagc tcaaatccac taactcgcgc taagcacagg    8160
ggtggcacta agtgcaacgt cgcggattta aagcctattt aaagcctgtc ttgtgcagaa    8220
ttaggtaata tacacacata gaattttagc aagcaataca aaattccaaa gcaaggacac    8280
cacagtgcta atttcgatat agaagctctg gaggcagcaa gaggagaagc tttgcagaga    8340
agcctaggat tcttcaatta gagagagatt agtgagctgt agagtgattg tgaggtgttg    8400
agaagaggag gagggatccc ccttcttgtg taaggaacaa ttatttggta ctctcaaact    8460
catttgtgtt agggttttc tgtaatggct agctaaacac ccttgttggg gatttctaag     8520
gaacaactga tgtaattact ttaatatcta attaattatg ttttatgtgt tcaatgcttc    8580
tttcaatgct taattactgc atgctcttgg tctgatcacc catttgtgtg tattgttagg    8640
tgactttagc attgggaaat gtaccgttgc cttagaactt gatagaagca ggactaaata    8700
actacattac cagggatgga ttatgggagt ttggttttct aaatatgttg tgatgataat    8760
gctatttaag ttaagcctag tcatacaaga gggatctgcg gacgaagctt aggttaaatt    8820
agtataaact acaagggat cgagatttag tactttaggc tacaacatag aacacaagaa     8880
catgattaat tagagaaata tcctcatatg catcaacttg tttgttagaa agacccaacg    8940 cttttttacct attgttgtca acttttactt acttgcattt ttttttttacc atagaagtag  9000 tttatttctg ttttaaccat caattatcaa tgttgttcca acaatgcctt acttctgaat    9060
aaaactctgt ctaataagca agttccctaa attcgatact tggatcactc tgttttaatt    9120
ttaaatactt gacaactca                                                  9139
```

<210> SEQ ID NO 23
<211> LENGTH: 10482
<212> TYPE: DNA
<213> ORGANISM: Glycine max

<400> SEQUENCE: 23

```
tgttagtcgt cttatatgac taacttttgt atagaaaaac cttttttcaaa acatgtatag    60 tttccccaat ttataattct tttgtaggaa tttgtaaata aatcttgata tgttttgata   120
cctgccatta gagtatcttt agttggagtt aatgagaaaa tttgtacaat ttcaggtcaa   180
aagaggctaa aatcttgaag tgctaaaagg agcagtcgtg ctaaatagag cctgtgggct   240
cagtgcacat ccaccgctaa gtgcagcttc agcatgctta gcgtgacaag ggaacctgaa   300
agagcacaag aatcaaggtc gcgcgctaag cgagacgttt gtcttttgcc aggctcagcg   360
cacgactggc gccaagccca atccactta ctcgcgctaa gcgcgatgtc gcgatttcag    420 agcctatttta agcctgaatt gtcagaatta gggtatgatt ttaagagacc agagctgtat   480 attttttgcac aaacttcgag aatagtgctc tggaggcagc agagaggcag cagctaagca   540
gggaagctag ggttcatcac tttgagagat tagagagtgt tttagtgatt gtgaggtgcc   600
```

-continued

```
aagaagacga ggagggatcc cccttcctgt gtaagcaaca attgctctgt actttctgtc    660
tcatttgtat tagggttcct tgtatggctt ggtaaaaacc ctagttgggg atttctaatg    720
aacagttgat gtaattactt ttcatatcta attaattgtg ttttgtgtgt tcagtgcttc    780
tttcaatact taattactgc atgctcttgg cctgatcacc ctcttgtgtg tactattagg    840
tgactttagc attgggaaat gtagtgctgc atagaacat gatagaagca aggctaaata     900
actgcattac ctaggatgga ttgtggggtt ttagttttct tattatgctg tgatgataat    960
gttgtttaag ttaagcctag tccaacaaga gggatctgag gatgaagctt gggttaaatt   1020
agtctaaact tatgagggat cgaggtttag tactttaggc ttcagcatag aacacaagaa   1080
catgattaat tagagaaata tcttcatatg cattaactcg tttgttagaa agacccaaca   1140
ctttatacct attgctgtca actttttaat tacttgcatt tactgctttt taacatagca   1200
tctagtttac ttttgtttat attctcaatt atcaatgttt gttcacacaa tgccatattt   1260
ctaaataaaa ctttgtctaa taaacaagtt ccctgagttt gatactcgga ttattccgtt   1320
ttaattttaa atgcttgata acctggtgcg ttttccgata tttcatttcc cttgaatata   1380
ctgcttgtaa atttgataga aaggaactgt gttgaagggt aaacaaaaat ttgacacaaa   1440
gcatttatgg cgccgttgtc ggggaactgg attcattaga agagttcagt tcagtttttaa  1500
ggcattgctt tattttgttt tctttaattc attgattctt tttgctaaca ttttagttac   1560
tgcacatttt attgttcttt ggaattggat aattttttgtt ttgtttcttt tgtatgcaaa  1620
ggagatctgt tgtaggtgat ttaattccca tagatttgga gattaatgct acttgcagga   1680
gacaaaatgc agagagaatt agaaattttt tgcaggactt agaagtagca gcaactctag   1740
gagagtgacc ctagaagatt actcaagtta aggccacagt ccaagcagct attagatgct   1800
tctgctgggg gaaaaataaa gttaaagacc cccgaagaag ccatggaact cattgaaaat   1860
atgactgcaa gtgacattac tattttgaga gatagagccc acattccaac aaaaagaagc   1920
ctactagagc tttcatcaca agatgcattg ttggcacaaa acaagttgat gtccaagcaa   1980
ttggaagcat tgaccaaaac actaagtaag tttccagctc aattacattc tgcacaatct   2040
ttaccatcta ctattttgca ggtcacagtg tgtgccatct gtggtggagc tcacgattct   2100
ggttgttgta tccccaatga agaaccaaca actcatgaag tcaattacat gggtaaccaa   2160
cctagaaata atttttaatgc aggtggattt cccgaattcc agcatggaca gtaatacaac   2220
caacaacagg gacaatggag gaccaccctg ggaattaatt caatagagac cagggtggac   2280
cgtccacaag gccgtaacaa caagggccta gtctctatga gcgtacaacg aagttggaag   2340
agactctagc tcaatttatg caggtttcta tgtctaacca aaagagcacg gagtttgcca   2400
taaagaattt ggaagtccaa gtgggacagc ttgcaaaaca gttggtggat aggccgtcaa   2460
agagctttag tgctaacact gagaaaaatt cgaaggggga atgtaaagct gtcatgacaa   2520
gaagcagaat ggcaacccat gttgatgaag gaaaagctta agaaggtg gaggagcata    2580
aacaacagtt ggcagctgag ccggcacttg aacccatttc tgattttgtt gaacttgagg   2640
aagttatgga agatgaagat gaccaaaagg aaaagagaaa gaagaagtag aaaaagaaaa   2700
atattagaaa aatgaaaaag aaaatgaaaa ggttgaggaa agaaagagga gcaagagtga   2760
ggtttcaaga gagaaaaaga gagagattac ttcagctgaa ggcaaggatg taccatatcc   2820
attggtacct tccaagaagg ataaagagc acacttagcc agatttcttg acatcttcaa   2880
gaagtcggag atcacattgc ttttggaga aactctccaa cagatgccac tctatgccaa   2940
attttttaaaa gacatgctga caaagaaaaa ctggtatatc cacagtgaca cgatagctgt   3000
```

```
ggaaggaaat tgtagtgctg tcactcaacg catccttcca ccaaagcata aggatccagg    3060
aagtgtcaca ataccatgtt ctattggtga agttgcagta ggcaaggctc tcattgactt    3120
gggagccagt atcaatttaa tgactctctc catgtgccag caacttggag agttagagat    3180
aatgcccact cgcatgaccc tacagttggc agatcgctcc attgctagac catatggagt    3240
gatcgaggat gtgttgattc aggtcaagca gcttgtattc cctgcaattt tgtggttatg    3300
gatatagagg aggatcctaa cattcccata atcttgggac gtcctttcat gtccacgacc    3360
agctgtgtag tagatatggg gaaaggcaaa ttagaactgg ttgtggagga tcagaaagtc    3420
tcattcgact tatttgaagc aatgaagcat ccaaatgatc aaaaagcttg ctttgatctg    3480
gataaggtag aataggagat agaattagct gctatagcca tggtactgca ctctcatttg    3540
gaaaaagcac gattaatcat gtagaatgtt tgaccaagga ggaggaacat gaagtgtaga    3600
cttgtattaa agagttggat ggtgcaggag aaaattccga gggacatact gcatttgaag    3660
aattgaagaa cagtgggaaa atagaaaaac caaaagtaga attgaagact ttgcctgcac    3720
attcgaagta tgtatcttgg aagacaatga ctccaaacca gtgattatta gcagctcttt    3780
gaagaaaaca gaagaagatc agttggtgca gattttgaag aaacataaag ctacaattgg    3840
atggcacata tctgacttga aaggaattag tccatcttat tgcatgcaca aaattattat    3900
ggaagctgat tacaaaccaa tgagacagcc tcaaagaaga ctgaacccaa tcatgaaaga    3960
ggaggtgcgc aaggaggtgc ttaagttgct agaagcaggc ctcacccat ctcagatagt     4020 gcgtgggtta gcccggtgca ggttgttctc aagaagggag tatgacagt cattaaaaat     4080 gataaagatg aattaatatc cacaaggact gtcaccgggt ggagaatgtg cattgattat    4140
cggaagttga ataatgccac ttggaaagac cattatccac tccctttcat ggaccatatg    4200
cttgagagac tcgcaaggca atcatattat tgttttctgg atggatattc tagttacaat    4260
tagattgcta tagatatcaa agatcaagat gtcgcaacct acccttcagt gggagggcga    4320
cgcgtgactt gcgcgtgcat gttccaagaa aggaatacgc gcggagtcgc caccaacgtt    4380
tatttgagga aaacgtcgga aaaaccggaa aagacgtgat ctacgaactt taagtgaaag    4440
gttcgggagt tgtatttacg cacggggaag gtattagcac cccacacgtc cgtcacaaga    4500
gatgacaacc tctaatcaaa tgtgcaaata tgacttcaat ttatgttatc ttcccccttt    4560
tttcacgttc ttatgttttt tttatgcctt tttatgtttt tatcttttg tggttgacaa     4620 gggcgtttcc ctttgctcct acgtattcct caattgtgat gagaaaatca aacctacgta    4680
gttcttttgt gaacaaagcg ttttggttaa gttatttttt atcctttttt gcaagatatg    4740 tttttattgaa tgaaaggtca tttaaggtgt tggaccatta gacaatcttt cgattctttt    4800
gaaaagtgag aaaacattaa ggcattggac cattaatgat ttctttattt ttgaaagagt    4860
taacaaagtt acatattgat tttaggcttt ttagaaatct acacttaacc aataaaagcg    4920
gaaaagacca tttcaaggcg ttggaccttt gaaaaatggc gttttaggc gatgacaaaa      4980 gtttggttta tgaattgatt ttagccttag tttcactttg gttattagtc gattcgattt    5040
aagaaagaga aatcccaaag aaaaacgtcc gattgatttt tgatttatt ttactaaaag     5100 atatttttga ttattatatt attattttac ctattttttgg ttttcaacgg gttacggcat   5160
gaccgaacag tcggatttca ttttaacaga aattaacgga tgttacaatt taaatgatcg    5220
gtggaaattt attttatttt ttgattaggc gagaaaatga cttaagtaaa tgactaaagc    5280
acgtcaaaag ggggtacgga aagtaaatga atgaaaata aaagcatgtg aaacaaatga    5340
ggaccactaa gggtacatag aatgaattgt ttgatttcgg gaacttaccg gttgaagatc    5400
```

-continued

```
gaagaacgac gaagaacgaa cgaagaacgt cgatgaacgg ttgaaaatct tcgcaaaatc    5460
acccacggaa acgttacgga agcacctcgg cttggatttt cttcacggaa acaattttc     5520 tcactaattt taagtgaatc tcagatacca ggagggtcga acattttgt tcttccctcc     5580 ttcccttatt tataggaaaa ggaaggagat gcttgccacc cagctcgccc aggcgagcta    5640
ggttgcttcc tccagaagca aatcctggaa ggcccaagtg ggcctggttg ctatttgaac    5700
ccccaatttt actaaatata ccccctgcct ttttttggtg attcttttc cgtaaagtta     5760 tggaaactta cgaatttcgt aacgatactt gttttcttc cgtaatgttg tggaaccta      5820 cggattacgt aatcatccct tttttgcctt ccggaacgtt acagaactt acggattgca     5880 cactaacact tccttttaat tttcggcatg tcacgaactt cacggattgt gctaccacgc    5940
ttttcttttg gcttccgaca tgtctcggaa cttcacaaat tgcctaacca tgggtgccaa    6000
atacctcgaa gtggtcaaac gacgtcgca tcccaacaac ggatggttct cggacgaaat     6060
tagggtatga cacaagagaa gacaactttc actttccctt tcggtgtatt tgcatatcga    6120
tgcatgcctt tcggtctatg caatgcccta gctacatttc agaggtgtat gatggcaatt    6180
ttttctgata tggtggaaaa atgcattgaa gttttcatgg acgatttctc tgttttgga     6240 ccatctttga tggttgctta tcaaatctgg aaagagtatt ttagagatgt gaagagtcca    6300
acctggtact taattgggaa aatgtcattt catggttcaa gaaggaatag tgctggggca    6360
taaaatatca gtaagggaa ttgaggtgga taaggtgaag attgatgtca ttgagaaact     6420
tcctcctcca atgaatgtca aacgaatgag aagtttctta ggacatgatg gattctatag    6480
gtgacttata aaagattttt caaaagtcgc caaaccactt agcaatttgt tgaacaaaga    6540
tgttgctttt gtgttcaatg gaaagtgtat tgaagcattt aatgatttga aaaccagact    6600
agtgtctgct ccagtaatta ctacaccaga ttgggggtaa gaatttgagt tgatgtgtga    6660
cgcgagcgat tatgctatag gtgcagtgct tggacaaagg aagggcaaaa tttttcatgc    6720
tatctactac gccagcaaag ttttaaatga tgcacaggtt aactatgcta ccacagaaaa    6780
agaaatgttg gcaattgttt atgcacttga aaagttcaaa tcttatttgg taggctcaaa    6840
agtcatcatc tacattgatc atgcaactat taaatatttt ctcaacaagg ccaattccaa    6900
aaccctgctt aataagatgg attttgctgc tgcaagaatt tgatttggta attcgggata    6960
aaaagggatc ggaaaatgtt gtagctaacc aatttgtcta gattggggaa taaagaagtc    7020
atgtcgaaag aagctgaaat tagagatgaa ttccctaatg agtcattatt cttggtgaat    7080
gagagaccct gatttgctga tatggccaac ttcaaagccg caggaatcat tccaaaagac    7140
ctaacttggc agtagaggaa gcaattcctg catgatgctc gattttatat ctgggatgac    7200
ccgcacttgt tcaagattgg agttgacaat cttctccgaa gatgtgtgac acaagaagaa    7260
gccaagaaca tattatggca ctgtcacaat tctccatgtg gcggccatta tggtggagat    7320
aagacgacga ccaaggtttt gcaatctgga ttcttttggc ccacactttt caaggatgct    7380
catcagaata tgctgcattg tgatcaatgt caaaggatgg ggggcatatc aaaaagaaat    7440
gaaatgcctt tacagaatat tatggaggtt gaggtatttg actgttgggg gattgatttt    7500
gtaggtccct tcccttttgtc ttttggcaat gaatacatac tagtggttgt tgactatgtc    7560
tctaaatggg ttgaagcagt ggctaccctg cataatgatg ctaagattgt ggtaaagttt    7620
ctaaagacga acatttttctc cagatttggg gtgcccagag ttttgattag tgatggaagc    7680
acacatttct gcaataataa gatacagaag gtgttgaagc aatataatgt aacacacaag    7740
gtagcatcag cttatcaccc ccaaaccaat gggcaagcag aagtgtcgaa caaggaattg    7800
```

-continued

```
aaaaagattt tagagaagac tatggcttct actagaaagg actggtccat taaactagat      7860
gatgctttat gggcgtatag gactgcattc aagactccga taggtttatc tccatttcag      7920
atggtgtatg gcaagtcttg tcacttacca gtggagatga aatataaaac atattgggcc      7980
ttgaagttgt tgaactttga tgaagccgaa tccagagaac aaaggaggct acaactttg       8040 gagttggaag agataaaatt aactgctat gaatcttcac agttgtacaa agaaaaaatt       8100
aaaaagtatc atgataaaaa actgctcaag agggattttc aacaaggaca caagtgttg       8160 cttttcacct caagacttaa attgtttcct gggaagctta atcgaaatg gtctagacca       8220 tttaccatca agaaagtccg aacatatgga gcagtggagc tttgtgatcc tcatatgggt     8280
ggtgaacgga caaaggctaa agcaatatca tggtggagct attgagagat tgaacactat     8340
tctacacttc aatccaggat aacaggacga tgcgtcaagc taatgacgtt aaccgagcgc     8400
ttacggggag gcaacccagg tctcttttta tttctatttt tcttgcattt aatttagtta     8460
gtttaattgc ttgtgattgt aaatgatttc taagcttggt tagtattgag aaaagggttt     8520 caaagttta gtaaagagat ggatagaaaa gacttagaga aaaaattttc agttgtccat      8580
ccgctaagcg cagcccttgt gctaagtgcc atgtcttaat gcactaagca tgtgcttgct     8640
tgcgctaagc actttgacct ttcaccagtt ggctagatgg ttcagctaag cgcacatcac     8700
tgcgctaaac ctaagttctt ctctggattt gaacttcatg acttgggctt agaggagttg     8760
atgcgctaag cgcaactcct tctctgttga aaaattattg taatagcatt aagcttaatt     8820
tcctctctgg aattgaactt tcaggaattg ggcttagcag caggatacgc taagcgccaa     8880
tccttcacta ttttgaaata cttggaattg cgctaagcct ggaaccatca ctgtaagtag     8940
agcttgtttt agtgctaagc ctaacatctt aggctaagtg aaaattgcag gaccaatcag     9000
agttgcagac agtgctaagc gcgtgtcctc gcactaagct tgaatacctc tctggaattt     9060
gaaattattg aattaggctt aacgcgagag gtggcgctaa gcgcatgggc cttaaactca     9120
aatgtcatgt tggcatgcta agcgcaacta tgcgctaagt gcgccaaaca aaatgctaa     9180 aataaaatag aactaccaat ggcagttacc atttacactt caaagctttt actcccttat     9240
gcttgtgccc acattcgtgc ttttgtgcat tttgctgcct ttgcttcaag ttattcctgc     9300
tttcttgctc tcatcttgca tttccatcac aatccaagta agttttcatg tttatttca     9360 ttttctttta taagcttaaa ccttagggta gatgatttag tgcttttag tttgcaattt      9420 tttttaggtt tagtgttttt aggttagttg ttagttaagg taggtttagg gtttacaatg     9480
taggttttag gttaggtttt tgagcccctt agggcaatg cctgaaaag gggtgaaaac       9540 ccgtgagtaa tttctagaaa tagcgatgaa cgtgctaagc gcacctgctg tgcttagcca     9600
gttcatcgca acttccttct aatgagtttc aatgatgagc tcgataagcg cgtttgtgcg     9660
ctaagtgaga caagtgtttt agacacttag tattttttc aattttgtt cagcactaaa       9720 gcctggcttc tcaggctaaa gcacaattct gtctttattt tcaattgtt ggaataaggc      9780 taagtgcagc ttgttgtgct aagcccatgt tatgtcttag tgaggttgag ctaagcgtgc     9840
cctactgcgc taagctcaat tcctccactg ttttcaaaag tgtggattta ggataagccc     9900
agcttgttgc gctaagccta gtctatggaa aaacattttc tgagtactca cgctaagcgt     9960
gtggctatcg ggcttagccc atgagtaaat tttcataaag cgcgctaagc ccagccttct    10020
gtgctaagca cccagtccta ctttcagttt tattttttg ttttttgtga ataatcctgt     10080
tttaactctg ttgtttgatc taattctttt cagatggcat ctaggaagag aaaggcccat    10140
gcctcaacat cccaggcccg ctatgataga tccagattca catctcagga ggcctgggat    10200
```

-continued

| | |
|---|---|
| cgttattcta gtgttgtcat tggcaggaaa atattacctg aaagaaatgt catgctctat | 10260 |
| tacacagagt ttgatgaatt cactgaagag ttagagagaa gaaacaggca caaggagtta | 10320 |
| acaaatttta tggatggcaa cattgatgtt gccattatga aggagttcta tgctaacctc | 10380 |
| tatgacccag aggataaatc acctaagcag gtgaggttca gaggtcattt agtgaaattt | 10440 |
| gatgcagatg ctctgaacac tttttttatg acccctgtga tc | 10482 |

<210> SEQ ID NO 24
<211> LENGTH: 1857
<212> TYPE: DNA
<213> ORGANISM: Arabidopsis thaliana

<400> SEQUENCE: 24

| | |
|---|---|
| atgagcaatt acagtggcag ttcttctgtt gatcctgact acaacatgga tgagacagaa | 60 |
| tcgtcatctt caaggccaga gagaacag agagaatacg aaagtttcag aaggaaagct | 120 |
| gagatagccc gaggaaagag agcgatgaga gagaggtatg agcttataga cgaagatctg | 180 |
| gaggacgagt acatgcctga acagactcgc agagctacca aacttctgca caagcccgac | 240 |
| atattgcctg ctgaggaata tgttaggctt ttcaagctga atgagttctg tagcacgagg | 300 |
| tatccttgct cgacctcact tgcacaactc ggattgttgg aagatgttca gcacctgtac | 360 |
| caaagttgtc atctggacac tttgatggct tatccgtatg tagcatatga agatgagaca | 420 |
| atacaattcc tctccacact acaagtagag ctctaccaag gtatgacctc tgatgagttg | 480 |
| gattgtgaag gattgggatt cttgcgattt tctgtgtatg gtcatgagta caggttatca | 540 |
| atcaagcgat tggaaggatt gtttgatttt cccagtggaa cgggatctaa gccaaagtat | 600 |
| gaaagagaag agttgaaaga cttgtggatc accatcggca gctctgtacc gttgaatgct | 660 |
| tccaggtcaa agagcaatca gatacgcagc cctgtcatca ggtacttcca gcgttctgta | 720 |
| gccaacgtac tctactcccg agagattaca gggactgtca ctaactctga tatggagatg | 780 |
| atcgcaatgg ccctcaaagg aactctccgc caaactaaaa atggcatgtc cctccagggt | 840 |
| gaagtcaatg cacacctct ctctatactt cttctgatcc atctgtgtgg atacaaaaac | 900 |
| tgggcggtca gcaataaccg caagagagca cgaggcgctc tgtgcatagg tggcgtggtg | 960 |
| acacctattc tgatagcttg tggagtccca ctcatttctg ctggactcga gccacgagca | 1020 |
| atggatatcg agcacctacg tcactgccaa ttcctggagt ttgcaatggt tgacgatttc | 1080 |
| cacaggttca ggtttgagca ctctacagac aggagagcta acatccttct ccctagccct | 1140 |
| gaggtcacac ggataatcga gggagataac attgatttta ggcctgagat tggacgcctc | 1200 |
| tactatgaga cgctccacc attagatgag gacgatcttc ttgaagaagc tgcttcggat | 1260 |
| gggatggatg aagatggagc agtaaagttc gacactagca tgtatcactt tgctgaacat | 1320 |
| gtacctccag cgaggcagag caagagcttg actgaagctc ataagaatta cagtaaattg | 1380 |
| cagaagtggt gcaagaagca ggacaggctg atcgccaagt gtttcaagct tctgacagac | 1440 |
| aagctgagtt gctcttcctc caccactgct attccacagg tacaacctcc tatggaaatg | 1500 |
| ccatcgagga gaattaatgc acctgcgcac aggcctgagc ttagcgagca gagagtccca | 1560 |
| catgtccagg ctaggcattc gtcattcgaa tcccgggaac acaagagaag aaggaaggct | 1620 |
| acactcactc gatctagcag cagatcacgc ctcattcact cgaggagatc actcgaccgt | 1680 |
| ggtgctggcc gcagcagaag gagagatgtc gagtttcctc agagcggtgc tggccgccac | 1740 |
| agagctgatg aggtcgagta cccatctgct ggagctgata cagaacaagg aggttcgtct | 1800 |
| atggcctggg agcaatcgca ggcagccatt gacgagcaac tacgttcatt cttcgac | 1857 |

<210> SEQ ID NO 25
<211> LENGTH: 1254
<212> TYPE: DNA
<213> ORGANISM: Pisum sativum

<400> SEQUENCE: 25

| | | | | | |
|---|---|---|---|---|---|
| atggaatcca | ggtccggagc | ttcgaaaaag | agaaagggcg | ggaatagttc | ccgtcccgtg | 60 |
| cccatacaat | tcgacaccga | caaatttgtc | gggccaaagc | aagcagtaag | atatgttgct | 120 |
| ttggaaaagc | gaaagatttt | gccggaaaag | agatttataa | tcaaccctga | aggcacgaac | 180 |
| cgtacattcg | ccgggctgat | taacagcaaa | agtgggacc | ggttaatatc | ccccttgaag | 240 |
| cattacgaca | tcgcaacagt | gcgtgagttc | tacgcgaacg | cactgccgaa | cgacgacgag | 300 |
| ccattcacat | ggacgtctag | agtgtccggc | cgtcctgttg | cgttcgatcg | ggatgcaatt | 360 |
| aaccgtgtcc | tgggtgaacc | gctccatctg | ggagccaatg | agagagacac | ttaccaccaa | 420 |
| gatttaaggc | ttcaccggga | taccgattcg | atttctactg | ccctgctttt | ggaagggaaa | 480 |
| tcagttgagc | tgaacccatc | tggggttccg | atgagatacc | ataggagga | catgattccc | 540 |
| ttggctcaac | tgatcctttt | gttggttctt | acaaacatca | acccaagtc | tcacacttct | 600 |
| accgtgccga | tcccagtggc | acacttggta | cacatcatcc | tcacgaatat | ccagattgat | 660 |
| gtggcaagga | ttattgcttt | ggagttgaag | tccgtgattg | aaagcgggct | aaagtcgggg | 720 |
| gaacgagtga | attgtcccct | tgctttccct | tgtctaatca | tggctttgtg | ccaacaagcg | 780 |
| agggtgaggc | taccctccaa | gggtcaagta | aggatcccgc | cggccattga | tgaccgatac | 840 |
| gtggccaagt | actgcaaacc | gaagaatgta | agaagtagtt | cagctgctga | ggttaccggg | 900 |
| gcttctgatg | gtcctggtac | ttttactcta | ggatccgatc | ctttccagca | ggctgtctgc | 960 |
| aactacaact | gggattggat | ggcggcaact | cagcgcgtca | tgctcgatat | gcacgattct | 1020 |
| atgcagctgt | tacagttgca | gatgcgcgac | ccctccggtg | agcattctat | gatgtcacgt | 1080 |
| gagcagtttc | tgcagcacgc | tagctggcct | gtggacaggc | ctgtgtttgg | agaggggcg | 1140 |
| ggtgctggtg | caactggtgc | tggtgctttt | tctggtgctg | ctgatgatga | tgatgatgat | 1200 |
| gaggctaccg | gttctgaagc | cggtagtgat | gagggttatg | agtccttgga | gggc | 1254 |

<210> SEQ ID NO 26
<211> LENGTH: 564
<212> TYPE: DNA
<213> ORGANISM: Arabidopsis thaliana

<400> SEQUENCE: 26

| | | | | | |
|---|---|---|---|---|---|
| tgtgattcat | gccagagaaa | aggcaacatc | aatagaagaa | atgagatgcc | tcagaatcca | 60 |
| atcttggaag | ttgagatctt | tgatgtatgg | gggattgatt | ttatgggtcc | attcccatct | 120 |
| tcatacggta | taaatatat | actggtcgcc | gtagactacg | tatcaaagtg | ggtcgaagct | 180 |
| attgctagtc | ctaccaacga | tgcaaaagtt | gtgctgaagt | tgttcaaaac | cataatcttc | 240 |
| ccaagatttg | gagttcccag | ggtagtaatc | agtgatggcg | gaaagcattt | catcaacaag | 300 |
| gttttttgaga | acctcttgaa | gaagcatggg | gtaaagcagg | ttgagatctc | caataggag | 360 |
| ataaaaacaa | ttctggaaaa | gactgttggg | attacaagga | aagactggtc | tgcaaagcta | 420 |
| gatgatgcat | tatgggctta | caggacagct | ttcaagaccc | ccataggtac | aactcctttc | 480 |
| aatcttctct | atggaaaatt | atgtcatcta | cccgttgagc | tcgagtacaa | agcaatgtgg | 540 |
| gcggtaaaac | ttctgaactt | tgac | | | | 564 |

<210> SEQ ID NO 27
<211> LENGTH: 600
<212> TYPE: DNA
<213> ORGANISM: Arabidopsis thaliana

<400> SEQUENCE: 27

| | | | | | |
|---|---|---|---|---|---|
| cttgatgctg | gtgtcatcta | ccctatctct | gatagtactt | gggtttctcc | agtgcattgc | 60 |
| gtccctaaaa | agggtggaat | gactgttgtc | aaaaatgaaa | aagatgaact | gatccctact | 120 |
| agaactataa | ctggtcatag | aatgtgcata | gattatagga | agttgaacgc | tgcatctagg | 180 |
| aaagatcatt | ttcctttacc | attcattgac | caaatgcttg | aacgtttggc | taatcatcca | 240 |
| tattattgct | tcttgatgg | atacagtggt | ttctttcaaa | taccaattca | ccctaatgat | 300 |
| caagaaaaaa | ccactttcac | gtgtccttat | ggaacttttg | cctataaaag | aatgccattt | 360 |
| ggtttatgca | atgctcctgc | aacatttcag | aggtgtatga | cctctatatt | ttcagactta | 420 |
| atcgaggaga | tggtggaggt | tttcatggac | gattttcgg | tctatggccc | ctctttctcc | 480 |
| tcatgtttgt | tgaatcttgg | cagggtattg | actaggtgcg | aagagacgaa | tcttgttctc | 540 |
| aattgggaaa | agtgtcattt | catggtgaag | gaaggcatag | tattggacca | caagatatca | 600 |

<210> SEQ ID NO 28
<211> LENGTH: 192
<212> TYPE: DNA
<213> ORGANISM: Arabidopsis thaliana

<400> SEQUENCE: 28

| | | | | | |
|---|---|---|---|---|---|
| tttgaaatca | tgtgtgatgc | atcagattac | gcagtaggag | ctgttctagg | ccagaaaata | 60 |
| gacaagaagc | ttcatgtcat | atattacgcc | agccgaacgt | tggatgacgc | tcagggaaga | 120 |
| tatgcaacaa | ctgagaagga | gcttctagct | gttgtattcg | catttgagaa | gttcagaagc | 180 |
| tatttggttg | ga | | | | | 192 |

<210> SEQ ID NO 29
<211> LENGTH: 597
<212> TYPE: DNA
<213> ORGANISM: Pisum sativum

<400> SEQUENCE: 29

| | | | | | |
|---|---|---|---|---|---|
| ttggatgcga | gaatgattta | cccgatctcg | gatagtccat | gggtcagtcc | cgtgcatgtg | 60 |
| gttccgaaga | aggtggaaa | taccgtcatc | cggaatgaca | aggatgaatt | gatccctacc | 120 |
| aaagttgcaa | cggggtggag | aatgtgtatt | gaatataggc | ggttgaatac | cgcaactcga | 180 |
| aaggaccatt | ttccactccc | gttcatggat | caaatgctgg | aaagactctc | cgggcaacaa | 240 |
| tactattgtt | tcttggatgg | ctattccggg | tataaccaaa | ttgccgttga | cccggccgat | 300 |
| cattaaaaga | cggctttcac | atgtccgttt | ggagtgttcg | cataccgaaa | aatgtccttt | 360 |
| gggttgtgca | atgcaccgac | gactttccaa | cgatgtgtgc | aagccatttt | tgccgacctt | 420 |
| aatgagaaaa | caatggaagt | cttcatggat | gacttctcgg | tatttggtgt | atcctttagt | 480 |
| ttatgcttgg | caaacttgaa | aacggtgctt | gaaagatgtg | tgaagaccaa | tcttgtgctt | 540 |
| aattggtaga | agtgccactt | catggtgacc | gaggggatag | tgcttggcca | taaagtc | 597 |

<210> SEQ ID NO 30
<211> LENGTH: 192
<212> TYPE: DNA
<213> ORGANISM: Pisum sativum

```
<400> SEQUENCE: 30
tttgagctaa tgtgtgatgc gagcaactat gcaatcggag cggtattagg ccaaagaaaa      60
gagaaaaaat ttcatgcgat acattacgca agtaaagttc ttaatgaggc tcaaattaac    120
tatgccacca ctgaaaaaga attacttgcg atagtgtatg cacttgaaaa gtttaggtct    180
tatcttatag gg                                                        192

<210> SEQ ID NO 31
<211> LENGTH: 581
<212> TYPE: DNA
<213> ORGANISM: Pisum sativum

<400> SEQUENCE: 31
tgtgatagtt gccagagaag cggtgggatt ggtaagagag acgagatgtc tctccaaaac     60
atccaagagg tcgaagtatt tgattgttgg ggcatcgatt ttgtaggacc attccccct    120 cttatggtaa cgagtatatg cttgtcgcag ttgaggcgat tgcctcacct cgggcggatg   180
cgaaaacggt aataattttt ttgaagaaaa acatattttc ccgtttcgga accccccgag   240
tgttgataag tgacggaggg tcacactttt gtaatgcacc gttggaaagc attttaaaac   300
attacggtgt atcacacaga gtggcaactc cgtatcaccc acaggctaat ggacaagccg   360
aggtctctaa tcgtgagatt aagagaattc tcgaaaaaac tgtgtcaaat tcgaaaaaag   420
agtggtcaca aaaattggat gaagcgttat gggcataccg taccgccttt aaagctccaa   480
ttgggctcac tccttttcaa ttggtgtttg gtaaaacttg ccatttgccg gtcgaattgg   540
agcacaaagc cttgtgggct ttgaaaatta ataattttga a                       581

<210> SEQ ID NO 32
<211> LENGTH: 1362
<212> TYPE: DNA
<213> ORGANISM: Glycine max

<400> SEQUENCE: 32
atggcctcct gtaaacaccg agctgtgccc acacccgggg aagcgtccaa ctgggactct     60
tcacgtttca ctttcgagat tgcttggcac agataccagg atagcattca gctccggaac    120
atccttccag agaggaatgt agagcttgga ccagggatgt tgatgagtt cctgcaggaa    180 ctccagaggc tcagatggga ccaggttctg acccgacttc agagaagtg gattgatgtt    240 gctctggtga aggagtttta ctccaaccta tatgatccag aggaccacag tccgaagttt    300
tggagtgttc gaggacaggt tgtgagattt gatgctgaga cgattaatga tttcctcgac    360
accccggtca tcttggcaga gggagaggat tatccagcct actctcagta cctcagcact    420
cctccagacc atgatgccat ccttttccgct ctgtgtactc caggggggacg atttgttctg    480 aatgttgata gtgccccctg gaagctgctg cggaaggatc tgatgacgct cgcgcagaca    540
tggagtgtgc tctcttattt taaccttgca ctgacttttc acacttctga tattaatgtt    600
gacagggccc gactcaatta tggcttggtg atgaagatgg acctggacgt gggcagcctc    660
atttctcttt agatcagtca gatcgcccag tccatcactt ccaggcttgg gttcccagcg    720
ttgatcacaa cactgtgtga gattcagggg gttgtctctg ataccctgat ttttgagtca    780
ctcagtcctg tgatcaacct tgcctacatt aagaagaact gctggaaccc tgccgatcca    840
tctatcacat ttcaggggac ccgccgcacg cgcaccagag cttcggcgtc ggcatctgag    900
gctcctcttc catcccagca tccttctcag cctttttccc agtgaccacg gcctccactt    960
ctatccacct cagcacctcc atacatgcat ggacagatgc tcaggtcctt gtaccagggt   1020
```

-continued

```
cagcagatca tcattcagaa cctgtatcga ttgtccctac atttgcagat ggatctgcca    1080
ctcatgactc cggaggccta tcgtcagcag gtcgcctagc taggagacca gccctccact    1140
gacagggggg aagagccttc tggagccgct gctactgagg atcctgccgt tgatgaagac    1200
ctcatagctg acttggctgg cgctgattgg agcccatggg cagacttggg cagaggcagc    1260
tgatcttatg ctttaatgtt ttcttttata ttatgtttgt gttctctttt atgttttatg    1320
ttatgttttt atgtagtctg tttggtaatt aaaaagaggt ag                       1362

<210> SEQ ID NO 33
<211> LENGTH: 192
<212> TYPE: DNA
<213> ORGANISM: Glycine max

<400> SEQUENCE: 33
tttgagttga tgtgtgacgc gagcgattat gctataggtg cagtgcttgg acaaaggaag      60
ggcaaaattt ttcatgctat ctactacgcc agcaaagttt aaatgatgc acaggttaac     120 tatgctacca cagaaaaaga aatgttggca attgtttatg cacttgaaaa gttcaaatct    180
tatttggtag gc                                                         192

<210> SEQ ID NO 34
<211> LENGTH: 597
<212> TYPE: DNA
<213> ORGANISM: Glycine max

<400> SEQUENCE: 34
ttggaggttg ggctcatata ccccatctct gacaacgctt gggtaagccc agtacaggtg      60
gttcccaaga aggtggaat gacagtggta caaaatgaga ggaatgactt gataccaaca     120
cgaacagtca ctggctggcg aatgtgtatt gactatcaca agctgaatga agctacacgg    180
aaggaccatt tccccttacc tttcatggat cagatgctgg agagacttgc agggcaggca    240
tactactgtt tcttggatgg atactcggga tacaaccaga tcgcggtaga ccccatagat    300
caggagaaga cggtctttac atgcccctttt ggcgtctttg cttacagaag gatgtcattc    360
gggttatgta atgtaccagc cacatttcag aggtgcatgc tgaccatttt ttcagacatg    420
gtggagaaaa gcatcgaggt atttatggac gacttctcgg tttttggacc ctcatttgac    480
agctgtttga ggaacctaga atggtacttc agaggtgcg tagagactaa cttggtactg    540
aattgggaaa agtgtcattt tatggttcga gagggcatag tcctaggcca caagatc      597

<210> SEQ ID NO 35
<211> LENGTH: 603
<212> TYPE: DNA
<213> ORGANISM: Glycine max

<400> SEQUENCE: 35
tgtgataaat gtcagagaac aaggggata tctcgaagaa atgagatgcc tttgcagaat      60
atcatggagg tagagatctt tgatagttgg ggcatagact tcatgggcc tcttccttca    120 tcatacagga atgtctacat cttggtagct gtggattacg tctccaaatg ggtggaagcc    180
atagccacgc tgaaggacga tgccaggta gtgatcaaat ttctgaagaa gaacattttt    240
tcccatttcg gagtcccacg agccttgatt agtgatgggg aacgcactt ctgcaacaat    300 cagttgaaga aagtccctgga gcactataat gtccgacaca aggtggccac accttatcac    360
actcagacga atgccaagc agaaattct aacagggagc tcaagcgaat cctggaaaag    420
acagttgcat catcaagaaa ggattgggcc ttgaagctcg atgatactct ctgggcctat    480
```

-continued

```
aggacagcgt tcaagactcc catcggctta tcaccatttc agctagtata tgggaaggca      540
tgtcatttac cagtagagct ggagcacaag gcatattggg ctctcaagtt gctcaacttt      600
gac                                                                   603

<210> SEQ ID NO 36
<211> LENGTH: 150
<212> TYPE: DNA
<213> ORGANISM: Glycine max

<400> SEQUENCE: 36
cctaaaatac tacaacgaca tgattggtgt tttaggataa ttgactgaaa aacctattat      60
caatttggcg ccgttgccaa ttgggtgttt gtttgttaca tttgagattt cagacttgct    120
tagatcaagt tcttttttcaa ttttcttttt                                     150

<210> SEQ ID NO 37
<211> LENGTH: 11
<212> TYPE: DNA
<213> ORGANISM: Glycine max

<400> SEQUENCE: 37
tggcgccgtt g                                                           11

<210> SEQ ID NO 38
<211> LENGTH: 15
<212> TYPE: DNA
<213> ORGANISM: Glycine max

<400> SEQUENCE: 38
tggcgccgtt gccgg                                                       15

<210> SEQ ID NO 39
<211> LENGTH: 27
<212> TYPE: DNA
<213> ORGANISM: Glycine max

<400> SEQUENCE: 39
tttttggcgc cgttgtcggg gattttg                                          27

<210> SEQ ID NO 40
<211> LENGTH: 9
<212> TYPE: DNA
<213> ORGANISM: Glycine max

<400> SEQUENCE: 40 tttggggga                                                               9

<210> SEQ ID NO 41
<211> LENGTH: 16
<212> TYPE: DNA
<213> ORGANISM: Glycine max

<400> SEQUENCE: 41
tttaatttgg gggatt                                                      16
```